United States Patent
Maeda et al.

(10) Patent No.: US 6,303,727 B1
(45) Date of Patent: Oct. 16, 2001

(54) LINEAR TRIENE COMPOUND AND COPOLYMER

(75) Inventors: Ken Maeda, Kuga-Gun; Masaaki Yasuda, Iwakuni; Terunori Fujita, Ohtake; Keiji Okada, Hatsukaichi; Makoto Kamimura, Yokohama; Kazuyuki Takimoto, Iwakuni; Hidetatsu Murakami, Kuga-Gun; Masaaki Kawasaki; Keiji Watanabe, both of Ichihara, all of (JP)

(73) Assignee: Mitsui Chemicals Inc., Tokyo (JP)

( * ) Notice: Subject to any disclaimer, the term of this patent is extended or adjusted under 35 U.S.C. 154(b) by 0 days.

(21) Appl. No.: 09/320,838

(22) Filed: May 26, 1999

(30) Foreign Application Priority Data

| May 28, 1998 | (JP) | 10-147942 |
| May 28, 1998 | (JP) | 10-147943 |
| Nov. 13, 1998 | (JP) | 10-323222 |
| Feb. 9, 1999 | (JP) | 11-031947 |

(51) Int. Cl.[7] .................................................. C08F 136/00
(52) U.S. Cl. ................................. 526/335; 336/339
(58) Field of Search ..................... 526/335, 336, 526/339

(56) References Cited

U.S. PATENT DOCUMENTS 3,887,531    6/1975    Schneider et al.
5,418,308  * 5/1995    Harvie ........................... 526/336
5,744,566  * 4/1998    Tsutsui et al. ................... 526/336

FOREIGN PATENT DOCUMENTS 0691319    1/1996   (EP) .

* cited by examiner

Primary Examiner—Bernard Lipman

(57) ABSTRACT

A novel and useful linear triene compound represented by the following formula (1) is co-polymerized with an α-olefin to obtain an ethylenically unsaturated copolymer which is superior in weather-ability, heat resistance and fastness to ozone, together with superior scorch stability and vulcanizability at high velocity (1)

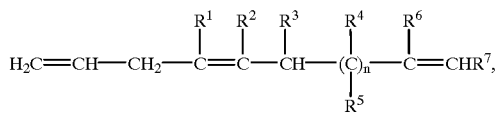

in which $R^1$, $R^2$, $R^3$, $R^4$, $R^5$ and $R^6$ stand each, independently of each other, for hydrogen atom or an alkyl having 1–3 carbon atoms, $R^7$ represents an alkyl having 1–3 carbon atoms and n is an integer of 0–5, with the proviso that each of $R^4$s or of $R^5$s may be identical with or different from each other, respectively, when n is 2 or greater.

9 Claims, No Drawings

LINEAR TRIENE COMPOUND AND COPOLYMER

FIELD OF THE TECHNIQUE

The present invention relates to a novel and useful linear triene compound and to a process for producing the same.

The present invention also relates to a novel an d useful ethylene/α-olefin/triene copolymer, to a composition containing such copolymer and to a formed article made of such composition.

BACKGROUND OF THE INVENTION

In general, hydrocarbo n compounds having in the molecule two or more carbon-carbon double bonds are called polyenes, a variety of which have been known, including, for example, 1,3-butadiene, 1,3-pentadiene, 1,4-hexadiene, ethylidene-2-norbornene (ENB), dicyclopentadiene and so on. By co-polymerizing such a diene with an α-olefin, such as ethylene, propylene or so on, an unsaturated copolymer having unsaturation bonds permitting vulcanization can be obtained. Due to its superior properties, such as weatharability, heat resistance and ozone-proof stability, such ethylenically unsaturated copolymer finds a wide variety of applications for, for example, automobile parts, industrial rubber products, electric insulator, articles for constructional and architectural uses and rubber products, such as rubber-lined cloth etc., and also for a material for polymer blends with, such as for example, polypropylene, polystyrene and others. Among these ethylene/α-olefin/diene copolymers, ethylene/propylene/5-ethylidene-2-norbornene copolymer exhibits, in particular, higher vulcanization velocity as compared with other ethylenically unsaturated copolymers and, hence, has especially widely been brought into practical uses.

Even this ethylene/propylene/5-ethylidene-2-norbornene copolymer, however, does exhibit inferior vulcanization velocity as compared with those commonly used diene-rubbers, such as natural rubber, styrene/butadiene rubber, isoprene rubber, butadiene rubber and nitrile rubber, and is inferior in the ability for co-vulcanizing with diene-rubbers.

Conventional ethylene/α-olefin/diene copolymers exhibit lower vulcanization velocity and, thus, are difficult to achieve an efficient productivity in producing vulcanized rubber products when reducing the vulcanization time or lowering the vulcanization temperature for the purpose of attaining a reduced energy consumption.

Therefore, it should be of great value in the industry, when such a polyene compound would be realized, that can afford to obtain, by co-polymerizing with an α-olefin, such as ethylene, an ethylenically unsaturated copolymer capable of being vulcanized at a high velocity and at the same time superior in the weatherability, heat resistance and fastness to ozone.

On the other hand, it has widely been recognized that, as a general property, a vulcanizable polymer exhibiting higher vulcanization velocity tends to have inferior scorch stability. This is believed due to that a polymer exhibiting higher vulcanization velocity may cause cross linking more easily during process steps other than the vulcanization, such as the compounded rubber storage step and rubber processing step before the vulcanization, as compared with polymers exhibiting lower vulcanization velocity, resulting in, thus, a premature vulcanization. Thus, a prompt vulcanizability is a reverse feature to the scorch stability, so that a polymer exhibiting both these properties may difficultly be obtainable. Thus, when it is attemped to increase the iodine value by increasing the proportion of ENB in the production of an ethylene/propylene/ENB copolymer, the vulcanization velocity may be increased, with a sacrifice in the scorch stability, resulting in a decrease in the workability on processing the rubber blend. Namely, troubles in the practical operation due to elevation in the rate of viscosity increase may apt to occur, by, for example, decrease in the extrusion output, increase in the motor load, stuffing of the cylinder or the die and so on. On the contrary, when a decrease in the iodine value is attempted, a decrease in the productivity of the vulcanized rubber due to retarded vulcanization may not be evaded, though an improvement in the scorch stability for the copolymer as a whole and, thus, in the workability thereof may be recognizable.

SUMMARY OF THE INVENTION

An object of the present invention is to provide a novel and useful linear triene compound capable of forming an ethylenically unsaturated copolymer which can be vulcanized at high velocity and which is superior in the scorch stability together with superiorities in weatherability, heat resistance and fastness to ozone.

Another object of the present invention is to provide a process for producing such a compound as above in an efficient manner.

A further object of the present invention is to provide a novel and useful α-olefin/triene copolymer exhibiting high vulcanization velocity and superior scorch stability.

A still furter object of the present invention is to provide a composition containg such copolymer.

A still further object of the present invention is to provide a formed article made of such composition.

The linear triene compound according to the present invention is represented by the following formula (1),

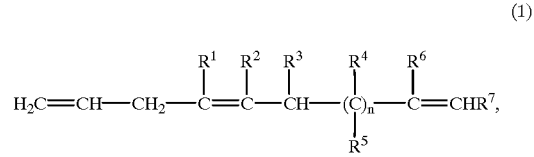

(1)

in which $R^1$, $R^2$, $R^3$, $R^4$, $R^5$ and $R^6$ stand each, independently of each other, for hydrogen atom or an alkyl having 1–3 carbon atoms, $R^7$ represents an alkyl having 1–3 carbon atoms and n is an integer of 0–5, with the proviso that each of $R^4$s or of R 5s may be identical with or different from each other, respectively, when n is 2 or greater.

The process for producing the linear triene compound according to the present invention represented by the formula (1) comprises reacting a triene compound having a conjugated diene structure represented by the following formula (3),

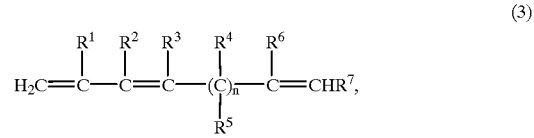

(3)

in which $R^1$, $R^2$, $R^3$, $R^4$, $R^5$ and $R^6$ stand each, independently of each other, for hydrogen atom or an alkyl having 1–3 carbon atoms, $R^7$ represents an alkyl having 1–3 carbon atoms and n is an integer of 0–5, with the proviso that each of $R^4$s or of $R^5$s may be identical with or different from each other, respectively, when n is 2 or greater, with ethylene.

The first copolymer {α-olefin/triene random copolymer (I-1)} according to the present invention comprises
   a structural unit ($U_A$) derived from an α-olefin (A) having 2–20 carbon atoms and
   a structural unit ($U_{B-1}$) derived from a linear triene compound (B-1) represented by the above formula (1), wherein the proportion of the structural unit ($U_{B-1}$) in the total of the structural unit ($U_A$) plus the structural unit ($U_{B-1}$) is in the range of 0.1–30 mole % and
   the intrinsic viscosity [η] determined in decalin at 135° C. is in the range of 0.1–10 dl/g.

The first composition according to the present invention (composition containing the α-olefin/triene random copolymer) comprises the α-olefin/triene random copolymer (I-1) as above, a vulcanizing agent (II) and/or a filler (III).

DETAILED DESCRIPTION OF THE INVENTION

The formed article according to the present invention comprises an extrusion-molded article, injection-molded article or transfer-molded article or a foamed product made of the above first composition.

<<The Linear Triene Compound>>

Concrete examples of the alkyl groups having 1–3 carbon atoms denoted by $R^1$ to $R^6$ and $R^7$ in the above formula (1) include methyl, ethyl, n-propyl and isopropyl. The numeral n stands for an integer of 0 to 5, preferably 1 to 4.

For the linear triene compound represented by the formula (1) according to the present invention {referred to hereinafter as the linear triene compound (B-1)}, a compound in which n equals 1 and both the groups $R^4$ and $R^5$ stand for hydrogen atom is preferred, wherein a particular preference is given to a compound in which both $R^4$ and $R^5$ are hydrogen atom and $R^6$ and $R^7$ denote each, independently of each other, methyl or ethyl. When such a linear triene compound (B-1) is used as a comonomer for copolymerizing with an α-olefin, in particular for synthesizing the second or the third copolymer as described afterwards, a copolymer exhibiting a superior balance between the vulcanization velocity and the scorching profile can be obtained.

Among the linear triene compounds (B-1) according to the present invention, those which are represented by the following formula (2){denoted hereinafter as the linear triene compound (B-2)},

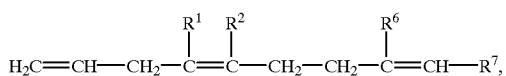

(2)

corresponding to those in which, in the formula (1), n equals 1 and $R^3$, $R^4$ and $R^5$ stand each for hydrogen atom, are preferred. Among the linear triene compounds (B-2), those in which $R^6$ and $R^7$ represent each, independently of each other, methyl or ethyl are preferred. When such a linear triene compound (B-2) is used as a comonomer for synthesizing the second or the third copolymer as described afterwards, a copolymer exhibiting a superior balance between the vulcanization velocity and the scorching profile can be obtained.

Concrete examples of the linear triene compound (B-1) represented by the formula (1) according to the present invention include the followings:

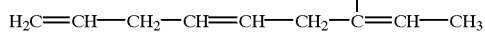
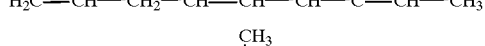
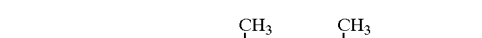
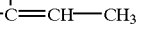
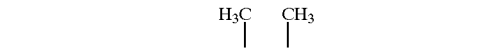
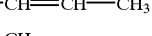
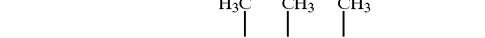
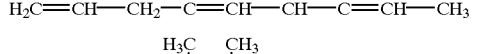
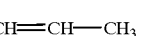
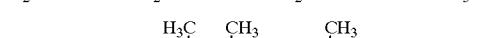
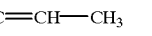
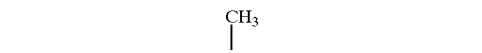
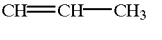
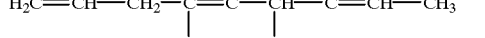
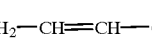
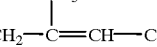
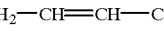
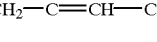
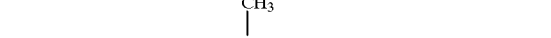
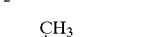

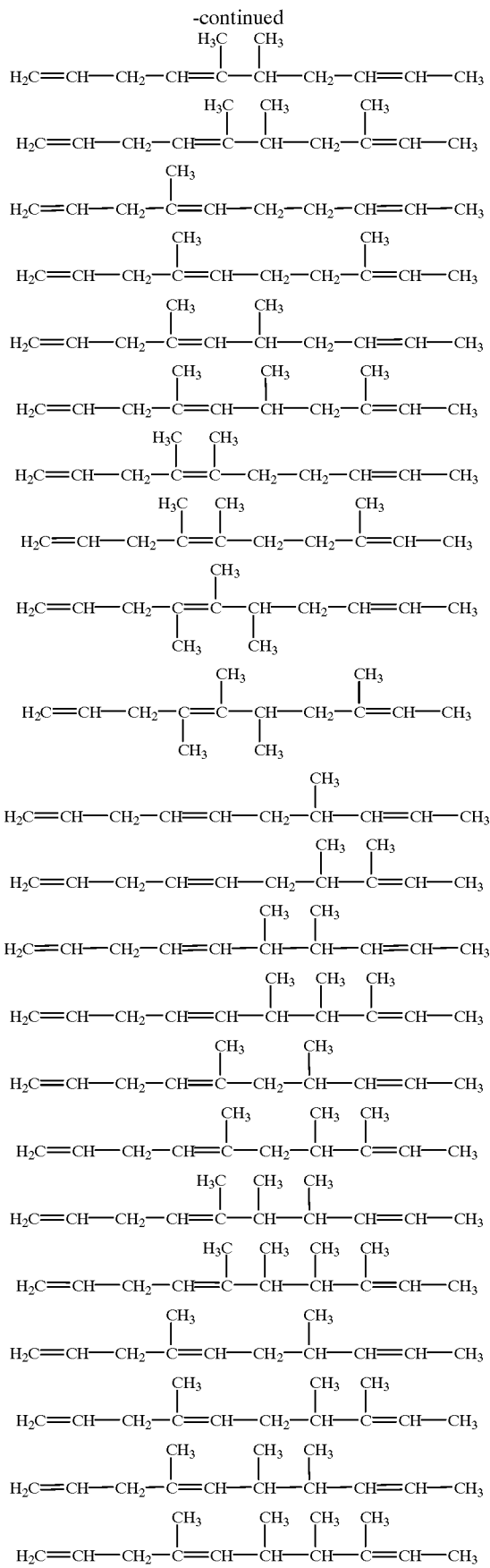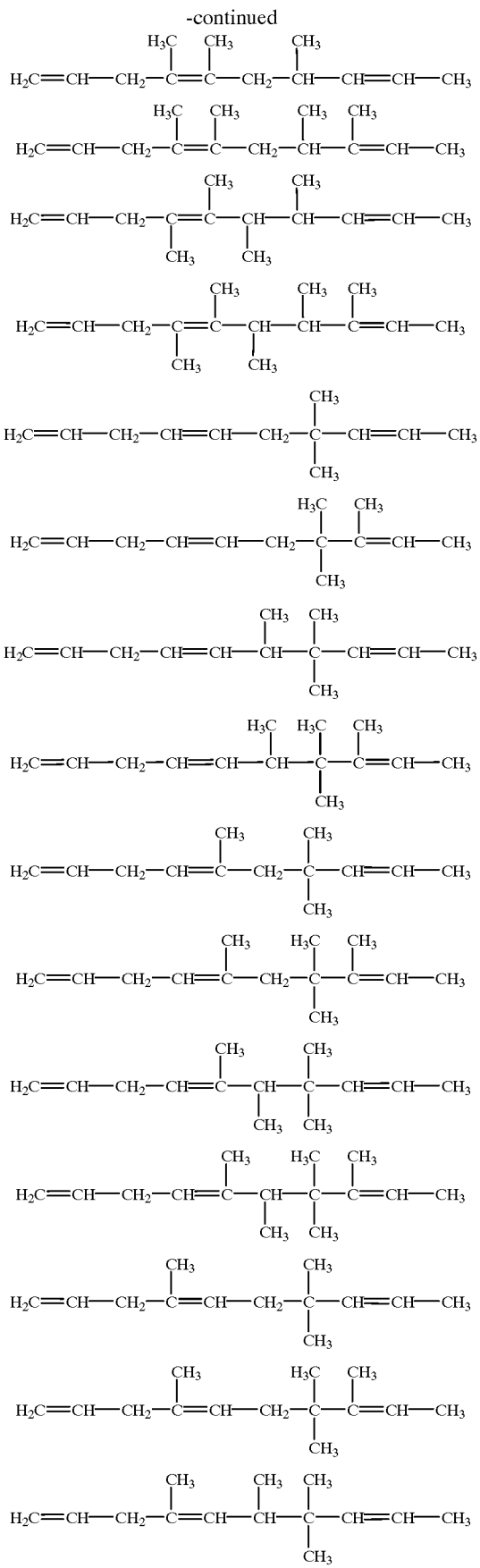

-continued

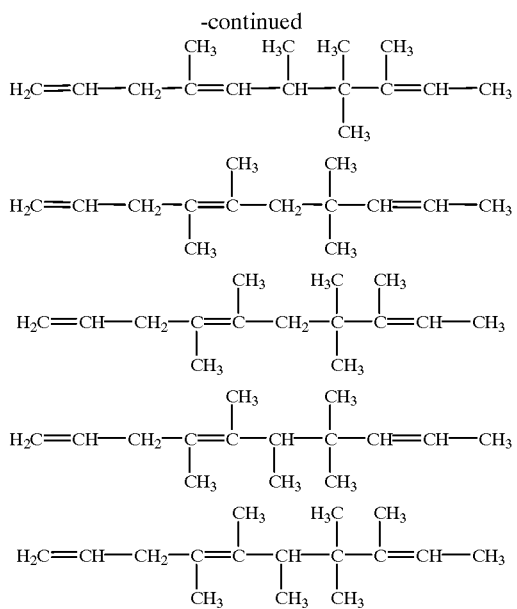

As the linear triene compound (B-2) represented by the formula (2), there may concretely be exemplified the following compounds:

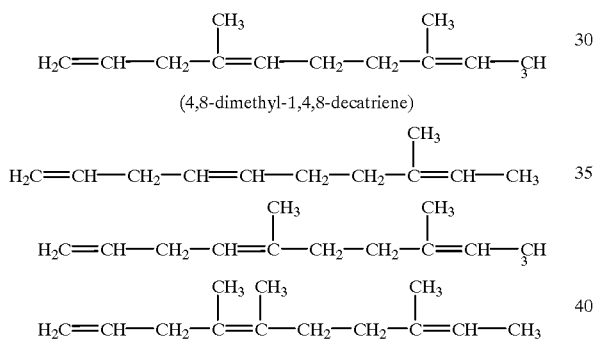
(4,8-dimethyl-1,4,8-decatriene)

The molecular structure of the linear triene compound (B-1) according to the present invention can be determined by techniques, such as mass spectrometry, IR absorption spectrometry and $^1$H-NMR spectrometry.

The linear triene compound (B-1) according to the present invention includes ordinarily stereoisomers (trans- and cis-isomers) which fall under the scope of the present invention.

When the linear triene compound (B-1) according to the present invention is co-polymerized with an α-olefin, such as ethylene or propylene, an ethylenically unsaturated copolymer capable of being vulcanized at high speed can be obtained. This copolymer exhibits also superiorities in the weatherability, in the heat resistance and in the ozone-proof stability.

In the case of using the linear triene compound (B-1) represented by the formula (1) according to the present invention for producing an ethylenically unsaturated copolymer, the linear triene compound (B-1) may either be present as a mixture of its trans- and cis-isomers or as an isolate compound of the trans- or cis-isomer. Also in such case of using the linear triene compound (B-1) for producing an ethylenically unsaturated copolymer, it is preferably that the number of hydrogen atoms situated at the allyl site with respect to the double bond attached to the carbon atom to which the groups $R^6$ and $R^7$ are coupled is at least three, more preferably at least 6.

<<The Process for Producing the Linear Triene Compound>>

The linear triene compound (B-1) represented by the formula (1) can be produced by reacting the triene compound having a conjugated diene structure represented by the formula (3) with ethylene.

The alkyl groups denoted by $R^1$ to $R^6$ and $R^7$ in the formula (3) are identical with those denoted by $R^1$ to $R^6$ and $R^7$ in the formula (1), wherein concrete examples thereof include methyl, ethyl, n-propyl and isopropyl.

Concrete examples of the triene compounds having an conjugated diene structure represented by the formula (3) include the followings:

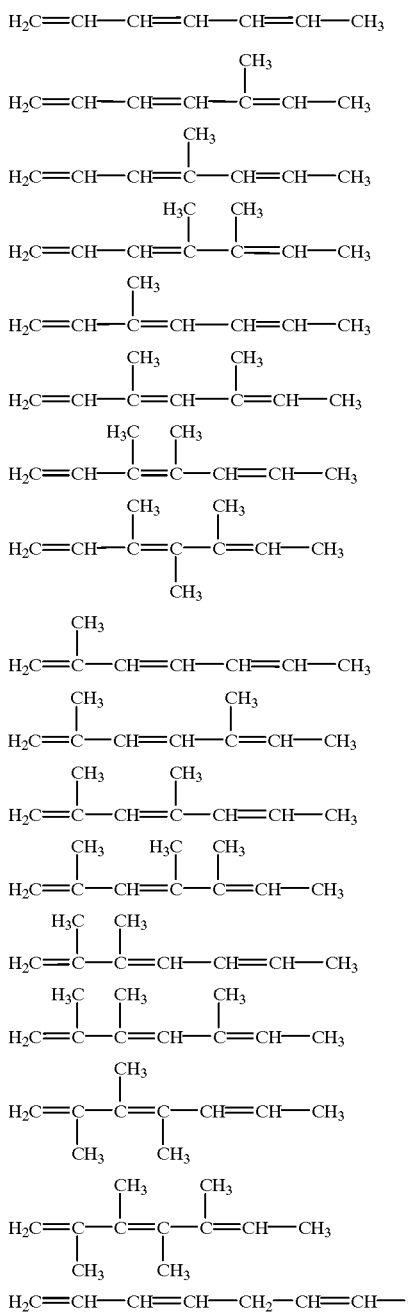

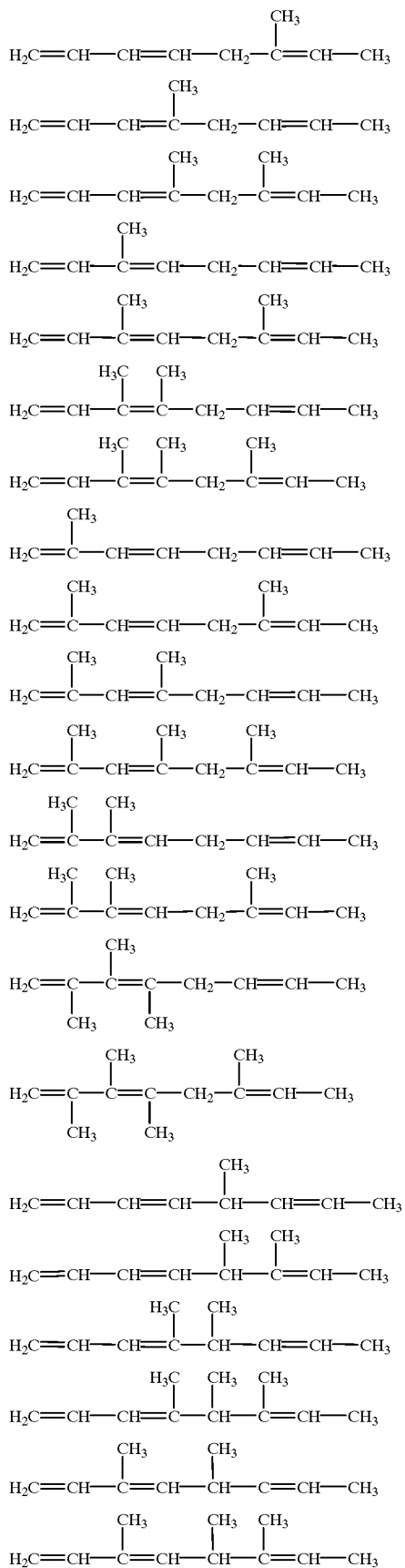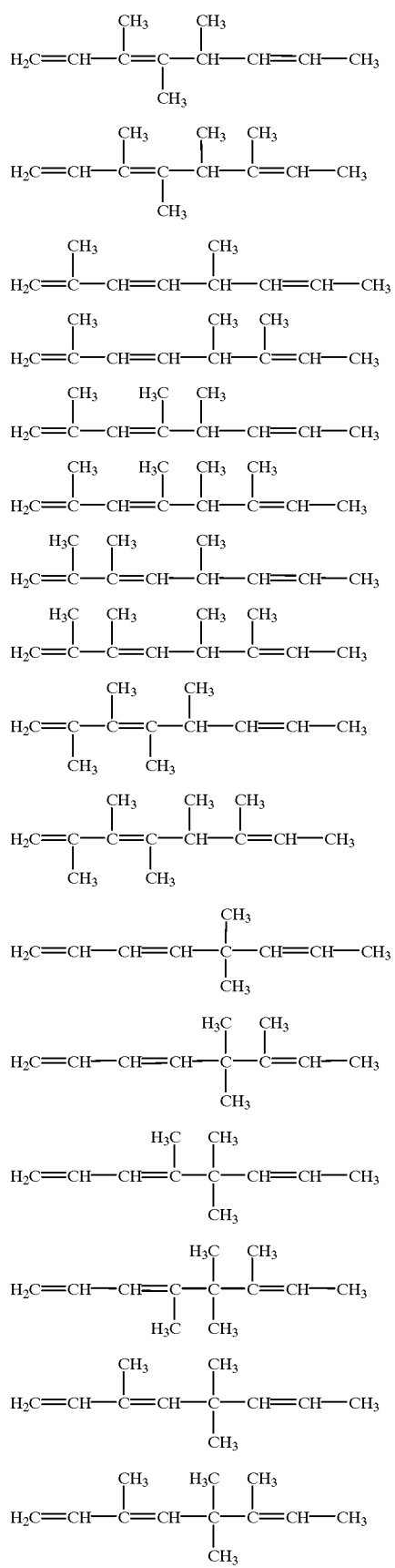

-continued

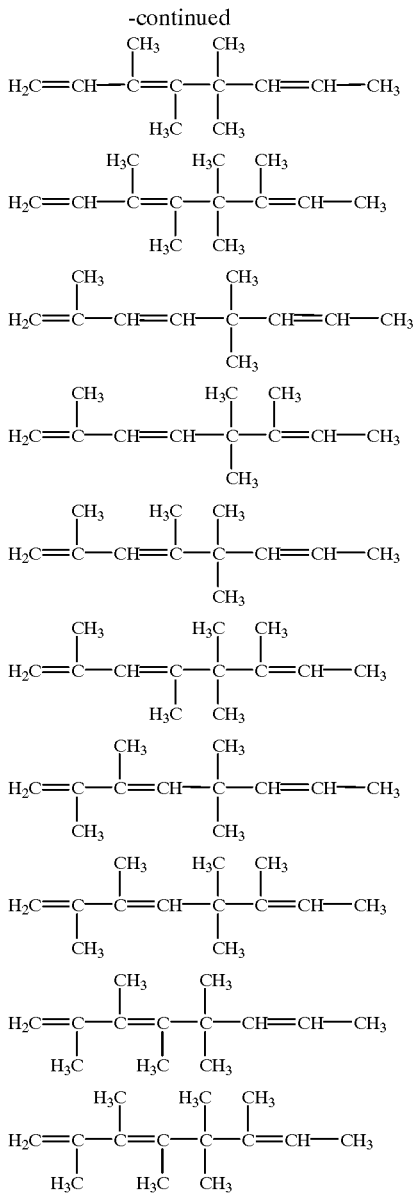

The linear triene compound (B-2) represented by the formula (2) can be produced by reacting a triene compound having a conjugated diene structure represented by the following formula (4),

(4)

in which $R^1$, $R^2$, $R^6$ and $R^7$ have the same meanings as those given for the formula (2), with ethylene.

The triene compound having a conjugated diene structure represented by the formula (4) may concretely be exemplified by the following compounds:

-continued

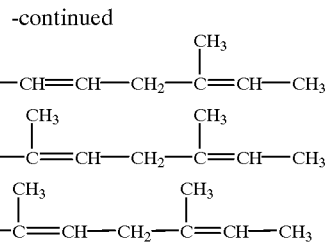

The reaction of the triene compound having a conjugated diene structure represented by the formula (3) with ethylene may be shown by the following reaction scheme (5):

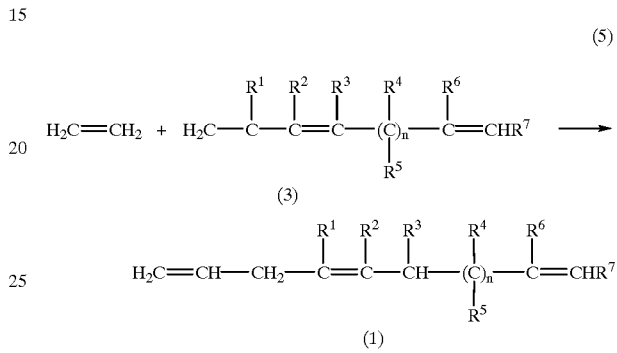
(5)

In the above reaction scheme (5), $R^1$ to $R^7$ and n are the same as those given in the formula (1) or (3).

According to the above reaction (5), the linear triene compound (B-1) according to the present invention is obtained usually as a mixture of trans- and cis-isomers. The trans- and cis-isomers can be separated by distillation, in accordance with the molecular structure of the linear triene compound (B-1).

In the reaction of a triene compound having a conjugated diene structure represented by the formula (3) with ethylene, there may, in some cases, be by-produced, together with the contemplated linear triene compound (B-1) of the present invention, branched chain triene compounds represented by the formula (6),

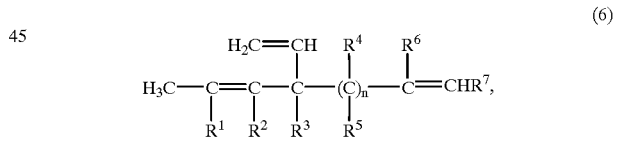
(6)

in which $R^1$, $R^2$, $R^3$, $R^4$, $R^5$ and $R^6$ represent each, independently of each other, hydrogen atom or an alkyl having 1–3 carbon atoms, $R^7$ denotes an alkyl having 1–3 carbon atoms and n is an integer of 0 to 5, with the proviso that each of $R^4$s or of $R^5$s may be identical with or different from each other, respectively, when n equals 2 or greater. These by-products can, if necessary, be separated from the contemplated linear triene compound (B-1) according to the present invention by a known technique, such as distillation.

In the production process according to the present invention, the reaction of the triene compound having a conjugated diene structure with ethylene may favorably be carried out under such a condition that the temperature is chosen usually in the range from 30 to 200° C., preferably from 50 to 150° C., and the ethylene partial pressure is selected usually within the range from 0.05 to 9.8 MPa (0.5 to 100 kgf/cm², gauge), preferably from 0.2 to 6.9 MPa (2–70 kgf/cm$^2$, gauge), though such condition may be variable in accordance with each specific triene compound having a conjugated diene structure employed. The reaction duration may, though not specifically limited, favorably be chosen usually in the range from 0.5 to 30 hours. For the reaction atmosphere, it is permissible to use ethylene therefor, while it is possible to use therefor an inert gas, such as argon and nitrogen, together with ethylene.

In the above reaction, it is not specifically necessary to use any reaction solvent, though permissible to use. Here, a hydrocarbon solvent, such as hexane, heptane, octane, nonane, decane, undecane tridecane toluene and xylene, may favorably be employed, while not restricted thereto.

The reaction of the triene compound having a conjugated diene structure represented by the formula (3) with ethylene is carried out usually in the presence of a catalyst. As the catalyst, there may usually be employed, for example, a catalyst which comprises a transition metal compound (a) or a transition metal complex (b) and an organoaluminum compound (c).

As the transition metal compound (a) there may be enumerated those which comprise a transition metal selected among those of Group 8 of the periodic table, such as iron and ruthenium, of Group 9 of the periodic table, such as cobalt, rhodium and iridium, and of Group 10 of the periodic table, such as nickel and palladium, for example, thiocyanates, cyanides, chlorides, bromides, iodides, carbonates, sulfates, nitrates, phosphates, acetates and acetylacetonates of the above-mentioned transition metals. For the transition metal compound (a), thiocyanats (a-1) and cyanides (a-2) of these transition metals are preferred.

As the thiocyanate (a-1) of the above-mentioned transition metal, there may concretely be enumerated, for example, thiocyanates of transition metals selected among those of Group 8 in the periodic table, such as iron and ruthenium, of Group 9 in the periodic table, such as cobalt, rhodium and iridium, and of Group 10 in the periodic table, such as nickel and palladium. For such thiocyanates (a-1) of transition metals, cobalt(II) thiocyanate and iron(II) thiocyanate are preferred.

As the cyanide of the above-mentioned transition metal, there may concretely be enumerated, for example, cyanides of transition metals selected among those of Group 8 in the periodic table, such as iron and ruthenium, of Group 9 in the periodic table, such as cobalt, rhodium and iridium, and of Group 10 in the periodic table, such as nickel and palladium. For such cyanides (a-2) of transition metals, cobalt(II) cyanide and iron(II) cyanide are preferred, wherein a particular preference is given to cobalt(II) cyanide.

As the catalyst, it is also possible to use a catalyst comprising a transition metal compound (a), which comprises a transition metal selected among those of Group 8 in the periodic table, such as iron and ruthenium, of Group 9 in the periodic table, such as cobalt, rhodium and iridium, and of Group 10 in the periodic table, such as nickel and palladium, a thiocyanato compound (d) and an organoaluminum compound (c). As the transition metal compound (a) to be used here, it is preferable to use compounds other than transition metal thiocyanates and transition metal cyanides.

As the catalyst, it is also possible to use a catalyst comprising a transition metal compound (a), which comprises a transition metal selected among those of Group 8 in the periodic table, such as iron and ruthenium, of Group 9 in the periodic table, such as cobalt, rhodium and iridium, and of Group 10 in the periodic table, such as nickel and palladium, a cyano compound (e) and an organoaluminum compound (c). As the transition metal compound (a) to be used here, it is preferable to use compounds other than transition metal thiocyanates and transition metal cyanides.

As the transition metal compound (a) to be used in combination with the thiocyanato compound (d) or the cyano compound (e), there may be enumerated concretely, for example, chlorides, bromides, iodides, carbonates, sulfates, nitrates, phosphates, acetates and acetylacetonates of transition metals selected among those of Group 8 of the periodic table, such as iron and ruthenium, of Group 9 of the periodic table, such as cobalt, rhodium and iridium, and of Group 10 of the periodic table, such as nickel and palladium. Among them, cobalt(II) acetylacetonate, iron(III) acetylacetonate, cobalt(II) nitrate, cobalt(II) chloride, cobalt (II) acetate and the like are preferred, wherein a special preference is given to cobalt(II) acetylacetonate, cobalt(II) nitrate, cobalt(II) chloride and cobalt(II) acetate.

As the thiocyanato compound (d) to be used in combination with the transition metal compound (a) according to the present invention, there may be enumerated, for example, thiocyanic acid salts, such as sodium thiocyanate, potassium thiocyanate and ammonium thiocyanate; thiocyanic acid esters, such as methyl thiocyanate, ethyl thiocyanate and phenyl thiocyanate. Among them, thiocyanic acid salts are preferred, wherein a special preference is given to potassium thiocyanate.

As the cyano compound (e) to be employed in combination with the transition metal compound (a) according to the present invention, there may be enumerated, for example, ionic cyano compounds, such as sodium cyanide, potassium cyanide and ammonium cyanide; and nitriles (e-1), such as acetonitrile, acrylonitrile, benzonitrile, phthalonitrile and adiponitrile. Among them, nitriles (e-1) are preferred, wherein special preference is given to acetonitrile and benzonitrile.

The transition metal compound (a) can be used as such for the preparation of the catalyst. According to the present invention, however, it is advantageous to incorporate the transition metal compound (a) in the preparation of the catalyst in a form of transition metal complex (b) in which organic ligands are coordinated to the transition metal. Thus, it is preferable to prepare the catalyst via formation of a transition metal complex (b) either in the course of the catalyst preparation from the transition metal compound (a) by introducing a coordinating compound (f), namely, an organic compound capable of being served as a ligand to the transition metal, into the reaction system to let it co-exist therewith or via a separate procedure of preparing the transition metal complex (b) beforehand from the transition metal compound (a) and a coordinating compound.

As the coordinating compound (f), namely, the organic comound capable of being served as a ligand to the transition metal, there may be enumerated, for example, oxygen-containing compounds, such as dimethyl ether, diethyl ether, dipropyl ether, tetrahydrofuran and acetylacetone; nitrogen-containing compounds, such as methylamine, dimethylamine, trimethylamine, ethylamine, diethylamine, triethylamine, cyclohexylamine, dicyclohexylamine, aniline, diphenylamine, pyridine, picoline, 2,2'-bipyridine and 1,10-phenanthroline; and phosphorus-containing compounds, such as triethylphosphine, tripropylphosphine, tributyiphosphine, triphenylphosphine, tri-o-tolylphosphine, bis (diphenylphosphino) methane, 1,2-bis(diphenylphosphino) ethane, 1,3-bis(di-phenylphosphino)propane, 1,4-bis (diphenylphosphino)butane, triphenylphosphite, triphenyiphosphine oxide and triphenyl phosphate.

Among them, phosphorus-containing compounds are preferred, wherein special preference is given to tri-o-tolylphosphine.

As the organoaluminum compound (c) to be incorporated as a catalyst component, there may be employed, for example, trimethylaluminum, triethylaluminum, triisobutylaluminum, chlorodimethylaluminum, chlorodiethylaluminum, dichioroethylaluminum and diethylaluminum ethoxide. Among them, triethylaluminum is preferred. The organoaluminum compound (c) can be incorporated as such or as a solution in toluene or hexane.

It is preferable according to the present invention, to carry out the reaction of the triene compound having a conjugated diene structure represented by the formula (3) with ethylene in the presence of any one of the catalysts given below, since thereby an efficient production of the linear triene compound represented by the formula (1) or (2) given previously can be attained.
1) A catalyst composed of the transition metal thiocyanate (a-1) and the organoaluminum compound (c)
2) A catalyst composed of the transition metal compound (a), the thiocyano compound (d) and the organoaluminum compound (c)
3) A catalyst composed of the transition metal cyanide (a-2) and the organoaluminum compound (c)
4) A catalyst composed of the transition metal compound (a), the cyano compound (e) and the organoaluminum compound (c)
5) A catalyst composed of the transition metal compound (a), the nitrile compound (e-1) and the organoaluminum compound (c)
6) A catalyst composed of the transition metal compound (a), acetonitrile or benzonitrile and the organoaluminum compound (c)
7) A catalyst, in which the transition metal compound (a), the transition metal thiocyanate (a-1) or the transition metal cyanide (a-2) in a catalyst of either one of the above 1) to 6) is replaced by a transition metal complex (b) to which one or more ligand compounds (f) are coordinating.

The amount of catalyst to be used in the production process according to the present invention is, in general, such that the transition metal compound (a) will be in the range of 0.001–10 mole %, preferably in the range of 0.01–1 mole %, with respect to the amount of the triene compound having a conjugated diene structure. The organic compound (f), namely, the coordinating compound to be served as a ligand to the transition metal, may be used usually in an amount of 20 molar times or less, preferably in the range of 0.1–10 molar times the transition metal compound (a). The organoaluminum compound (c) may be used in an amount in the range of 1–200 molar times, preferably in the range of 3–100 molar times the transition metal compound (a).

The product, namely, the linear triene compound (B-1) represented by the formula (1) can be isolated after the reaction of the triene compound having a conjugated diene structure with ethylene from the reaction mixture by an ordinary technique, for example, by having recourse to distillation etc. to remove the reaction solvent, by-products and so on. When a catalyst is employed in the reaction, it is preferable to incorporate a de-metallation treatment by, for example, washing the reaction mixture with water.

<<The First Copolymer (I-1): α-Olefin/Triene Random Copolymer>>

Now, the first copolymer (I-1) according to the present invention, namely, the α-olefin/triene random copolymer, is described.

As the α-olefin (A) having 2–20 carbon atoms constituting the first copolymer (I-1), namely, the α-olefin/triene random copolymer, according to the present invention, there may be enumerated concretely, for example, ethylene, propylene, 1-butene, 1-pentene, 1-hexene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 1-octene, 1-decene, 1-dodecene, 1-tetradecene, 1-hexadecene, 1-octadecene and 1-eicosene. They may be used either each solely or in a combination of two or more of them. Among these α-olefins (A), those having 2–8 carbon atoms, such as ethylene, propylene, 1-butene, 1-hexene and 1-octene, are preferred.

Among the linear triene compounds (B-1) represented by the formula (1), those in which n equals 1 and the groups $R^4$ and $R^5$ stand each for hydrogen atom are preferred. Still among these linear triene compounds (B-1), further preference is given to those in which $R^6$ and $R^7$ denote each, independently of each other, methyl or ethyl. The first copolymer according to the present invention (I-1), namely, the α-olefin/triene random copolymer, obtained using the linear triene compound (B-1) as the starting material exhibits superior balance between the vulcanization velocity and the scorching profile.

The linear triene compound (B-1) represented by the formula (1) has usually a stereoisomerism (such as trans- or cis-isomer). The linear triene compound (B-1) used as the starting monomer may either be a mixture of trans- and cis-isomers or a sole trans- or cis-isomer.

In the first copolymer according to the present invention (I-1), namely, the α-olefin/triene random copolymer, structural units derived from the α-olefin having 2–20 carbon atoms (A) and structural units derived from the linear triene compound (B-1) represented by the formula (1) are bound with each other in a random distribution. The first copolymer (I-1) has unsaturation bonds inherited from the linear triene compound (B-1) represented by the formula (1). The main chain of the first copolymer (I-1) according to the present invention, the α-olefin/triene random copolymer, has a substantially linear structure. The assumption that this copolymer is substantially linear and does not substantially contain a cross-linked gelled molecular structure can be ascertained by the fact that this copolymer dissolves in an organic solvent without exhibiting any insoluble residue. For example, this can be ascertained by the fact that this copolymer dissolves completely in decalin (decahydronaphthalene) at 135° C. on the determination of its intrinsic viscosity [η]. The first copolymer (I-1) according to the present invention, i.e. the α-olefin/triene random copolymer, can be utilized for applications including starting material for various rubber products and modifiers for resins and can be used favorably for the starting material of rubbers for extrusion molded articles, such as glass run channel, wiper blade and weather strip sponge; for injection molded articles, such as in-mold foamed sponge; and for transfer-molded articles.

The first copolymer (I-1) according to the present invention, i.e. the α-olefin/triene random copolymer, has a content of the structural unit ($U_{B-1}$) derived from the linear triene compound (B-1) represented by the formula (1) in the range from 0.1 to 30 mole %, preferably from 0.5 to 10 mole %. When the content of the structural unit ($U_{B-1}$) derived from the linear triene compound (B-1) represented by the formula (1) is in the above-mentioned range, the first copolymer (I-1) according to the present invention, i.e. the α-olefin/triene random copolymer, exhibits a high vulcanization velocity and a superior scorch stability.

The first copolymer (I-1) according to the present invention, i.e. the α-olefin/triene random copolymer, has an intrinsic viscosity [η] determined in decalin at 135° C. in the range from 0.1 to 10 dl/g, preferably from 0.5 to 5 dl/g, more preferably from 1.0 to 4.5 dl/g. When the intrisic viscosity is in the above-mentioned range, the first copolymer (I-1) according to the present invention, i.e. the α-olefin/triene random copolymer, exhibits a high vulcanization velocity and a superior scorch stability.

The structural unit ($U_{B-1}$) derived from the linear triene compound (B-1) in the first copolymer (I-1) according to the present invention, i.e. the α-olefin/triene random copolymer, has a molecular structure which is represented substantially by the following formula (1-a):

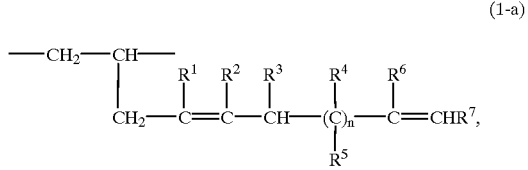

(1-a)

in which $R^1$ and $R^2$ represent each, independently of each other, hydrogen atom, methyl or ethyl and $R^3$ and $R^4$ denote each, independently of each other, methyl or ethyl.

The fact that the structural unit ($U_{B-1}$) derived from the linear triene compound (B-1) represented by the formula (1) has the molecular structure represented by the above formula (1-a) can be confirmed by inspecting the first copolymer (I-1) according to the present invention, i.e. the α-olefin/triene random copolymer, by $^{13}$C-NMR spectrum.

It is preferable that the α-olefin (A) for the first copolymer (I-1) according to the present invention, i.e. the α-olefin/triene random copolymer, comprises ethylene (A-1) and another α-olefin (A-2) having 3–20 carbon atoms and that the mole ratio of the structural unit ($U_{A-1}$) derived from ethylene (A-1) relative to the structural unit ($U_{A-2}$) derived from the above-mentioned α-olefin (A-2), namely, ($U_{A-1}$)/($U_{A-2}$), is in the range from 99/1 to 30/70, preferably from 90/10 to 50/50. When the mole ratio ($U_{A-1}$)/($U_{A-2}$) is in the above-mentioned range, the first copolymer (I-1) according to the present invention, i.e. the α-olefin/triene random copolymer, exhibits favorable rubbery material properties.

It is preferable that the α-olefin (A) for the first copolymer (I-1) according to the present invention, i.e. the α-olefin/triene random copolymer, comprises an α-olefin (A-2) having 3–20 carbon atoms and, if necessary, an α-olefin (A-3) having 2–20 carbon atoms which is different from the α-olefin (A-2) and that the content of the structural unit ($U_{A-2}$) derived from said α-olefin (A-2) having 3–20 carbon atoms is in the range from 70 to 99.9 mole %, preferably from 75 to 95 mole %, and the content of the structural unit ($U_{A-3}$) derived from the above-mentioned another α-olefin (A-3) having 2–20 carbon atoms is in the range from 0 to 29.9 mole %, preferably from 1 to 25 mole %, wherein the content of the structural unit ($U_{B-1}$) derived from the linear triene compound (B-1) is in the range from 0.1 to 30 mole %, preferably from 0.2 to 10 mole %, provided that the total sum of the contents of ($U_{A-2}$)+($U_{A-3}$)+($U_{B-1}$) amounts to 100 mole %. When the content of each structural unit is in the above-mentioned respective range, the first copolymer (I-1) according to the present invention, i.e. the α-olefin/triene random copolymer, exhibits favorable rubbery material properties.

The first copolymer (I-1) according to the present invention, i.e. the α-olefin/triene random copolymer, may have, co-polymerized therein, other compound(s) as comonomer(s) in addition to the α-olefin (A) having 2–20 carbon atoms and the linear triene compound (B-1) represented by the formula (1). For such other comonomer(s), there may be exemplified non-conjugated dienes and cyclic olefins. The content of the structural unit derived from such other comonomer(s) may favorably be 30 mole % or less, preferably in the range from 0.5 to 10 mole %, based on the total moles of the entire structural units derived from all comonomers. For such other comonomer(s), there may be employed those which are exemplified for the second copolymer according to the present invention described afterwards.

The first copolymer (I-1) according to the present invention, i.e. the α-olefin/triene random copolymer, can be vulcanized at high velocity and has a superior scorch stability together with superiorities in the weatherability, heat resistance and fastness to ozone.

The first copolymer (I-1) according to the present invention, i.e. the α-olefin/triene random copolymer, can be brought into practical use not only in the unvulcanized state as such but also in the vulcanized form by subjecting it to vulcanization by the technique described afterwards, wherein the characteristic features thereof may be developed more effectively by vulcanization. When the copolymer is vulcanized, a high vulcanization velocity is attained, though the term till scorching is not reduced.

The first copolymer (I-1) according to the present invention, i.e. the α-olefin/triene random copolymer, can be used especially favorably for the starting material for various rubber products and as a resin modifier as well.

As the rubber products, there may be exemplified automobile parts, industrial rubber products, electric insulator, articles for constructional uses and rubber-lined cloth. Concrete examples include glass run channel, wiper blade, weather strip, sponge, hoses, grommet, side wall of tire, sheath for electric cable and gasket.

When the first copolymer (I-1) according to the present invention, i.e. the α-olefin/triene random copolymer, is added as a resin modifier to resins, such as polypropylene, polyethylene, polybutene and polystyrene, the shock resistance and the resistance to stress cracking of the resin can be elevated greatly.

The first copolymer (I-1) according to the present invention, i.e. the α-olefin/triene random copolymer, may be vulcanized solely or co-vulcanized together with other rubber material.

The first copolymer (I-1) according to the present invention, i.e. the α-olefin/triene random copolymer, can, due to its high vulcanization velocity, be vulcanized within a more short vulcanization time or at a lower vulcanization temperature without using a large amount of vulcanizing agent, as compared with conventional unsaturated copolymers based on olefin. The first copolymer (I-1) according to the present invention, i.e. the α-olefin/triene random copolymer, has a superior scorch stability, so that it can be processed by foaming molding with a stable expansion ratio and, thus, an increased productivity of foamed article can be attained. Thus, the foaming expansion ratio is determined by a delicate balance between the initial viscosity of the raw resin material, the rate of elevation of the viscosity during the molding and the rate of decomposition of the foaming agent, so that control of the expansion ratio is difficult, since the higher the viscosity elevation rate, the greater will be the variation in the viscosity change rate. However, the scorch stability is superior and, thus, the viscosity elevation is lower in the first copolymer (I-1) according to the present invention, i.e. the α-olefin/triene random copolymer, so that it permits to produce a foamed molded article at a stable expansion ratio efficiently. The first copolymer (I-1) according to the present invention, i.e. the α-olefin/triene random copolymer, is superior also in the processing stability during working on an extruder due to its superior scorch stability and, therefore, any troublesome phenomenon caused from viscosity increase upon working by, for example, an extruder, such as reduction in the extrusion output, increase in the motor load and stuffing or clogging of the cylinder and/or die due to elevation of the viscosity by the progress of vulcanization within the extruder, can be prevented.

It is a further advantageous feature of the first copolymer (I-1) according to the present invention, i.e. the α-olefin/triene random copolymer, that it excells in the fastness to thermal debasement while maintaining the superior characteristic features mentioned above.

<<Production of the First Copolymer (I-1), i.e. the α-Olefin/Triene Random Copolymer>>

The first copolymer (I-1) according to the present invention, i.e. the α-olefin/triene random copolymer, can be produced by the same procedures as in the production of the second copolymer according to the present invention as described afterwards. Thus, it can be produced by co-polymerizing the α-olefin having 2–20 carbon atoms, the linear triene compound (B-1) represented by the formula (1) and, if necessary, other comonomer(s) to be incorporated optionally in the presence of the same catalyst as that exemplified in the production of the second copolymer described later under the same condition.

The first copolymer (I-1) according to the present invention, i.e. the α-olefin/triene random copolymer, obtained in this way is capable of being vulcanized at higher velocity and superior in the scorch stability together with superiorities in the weatherability, heat resistance and fastness to ozone, so that it can be utilized for applications, such as the starting material for various rubber products and as modifier for resins. Vulcanized rubber products obtained by vulcanization of the first copolymer (I-1) according to the present invention, i.e. the α-olefin/triene random copolymer, are superior not only in the weatherability, heat resistance and fastness to ozone but also in the rubbery elasticity. On producing vulcanized rubber products using the first copolymer (I-1) according to the present invention, i.e. the α-olefin/triene random copolymer, it can be subjected to a high velocity vulcanization and, therefore, a high productivity can be attained.

The first composition according to the present invention comprises the first copolymer (I-1) according to the present invention, i.e. the α-olefin/triene random copolymer, the vulcanizing agent (II) and/or the filler (III). The first composition according to the present invention consists of a vulcanizable rubber composition, which can be brought into practical use in the unvulcanized state as such, though it can develop more advantageous features when used in a vulcanized form.

The vulcanized rubber products obtained by vulcanization of the first composition according to the present invention are superior not only in the weatherability, heat resistance, fastness to ozone and fastness to dynamic fatigue but also in the rubbery elasticity and low temperature flexibility. On producing vulcanized rubber products using the first composition according to the present invention, a high productivity can be attained, since the first copolymer (I-1) according to the present invention, i.e. the α-olefin/triene random copolymer, can be vulcanized at high velocity. It is also possible to reduce the amount of the vulcanizing agent (II) and that of vulcanization accelerator to be incorporated, so that vulcanized rubber product exhibiting superior appearance with lower degree of blooming can be obtained.

The first composition according to the present invention can be vulcanized in the same way as in the case of the second composition as described later. Thus, it can be vulcanized by blending it with compounds constituting the vulcanization system, such as the vulcanizing agent (II), a vulcanization accelerator, a vulcanization assistant and so on, and effecting the vulcanization of the blend under the same condition as in the case of the second composition described later.

As the filler (III) to be incorporated in the first composition according to the present invention, the same reinforcing agent and softener as in the case of the second composition described later may be enumerated. The amount of these reinforcing agent and softener to be incorporated in the composition may also be the same as in the second composition described later.

There may be blended with the first composition according to the present invention, in addition to the above-mentioned components, other ingredients and chemicals, including compounds constituting the foaming system, such as foaming agent and foaming assistant, antioxidant (stabilizer), processing assistant, plasticizer, colorant and other rubber components. The kinds and amounts of these other ingredients may be selected so as to cope with each requirement.

The first composition according to the present invention may be processed by foaming molding when it contains compounds constituting a foaming system, such as foaming agent and foaming assistant. The foaming molding can also be carried out in the same manner as in the case of the second composition described later. Thus, the foaming agent and foaming assistant identical with those in the case of the second composition described later are used in also the same amount.

The first composition according to the present invention may contain other known rubber component(s) than the first copolymer (I-1), i.e. the α-olefin/triene random copolymer, within an extent not obstructing the purpose of the present invention. Such other rubber component(s) may be the same as that in the case of the second composition described later and the amount thereof is also the same, whereby better material properties as a composite rubber can be developed.

The first composition according to the present invention may preferably contain the first copolymer (I-1), i.e. the α-olefin/triene random copolymer, in an amount of at least 20%, preferably at least 25%, based on the entire weight of the composition. When the content of the first copolymer (I-1), i.e. the α-olefin/triene random copolymer, is in the above range, better material properties as a composite rubber can be developed.

The first composition according to the present invention can be utilized as the raw material for rubber products, such as automobile parts, automobile shock-damping rubber, industrial rubber products, electric insulator, articles for constructional uses and rubber-lined cloth, in particular, as the starting rubber material for extrusion molded articles, such as sealant, glass run channel, wiper blade and sponge rubber weather strip; injection-molded articles, such as in-mold foamed sponge rubber article and sponge rubber seal for automobile door; and starting rubber material for transfer-molding. Concrete examples of the sealant rubber include those which are enumerated in the case of the second composition described later.

When the first composition according to the present invention is used for starting material for sealant, glass run channel, wiper blade, sponge rubber weather strip and in-mold foamed article as mentioned above, they can be produced at a high productivity by high velocity vulcanization and are superior in the rubbery elasticity, weatherability, heat resistance, fastness to ozone and low-temperature flexibility. For example, sponge rubber weather strip can be produced at a high productivity by vulcanization of the extruded green product within a short period of time. Here, the vulcanization proceeds sufficiently within a short time to provide the end product having superior rubbery elasticity.

The first composition according to the present invention can be prepared in the same manner as in the case of the second composition according to the present invention described later except that the first copolymer (I-1), i.e. the α-olefin/triene random copolymer, is incorporated.

The vulcanized product (vulcanized rubber product) of the first composition according to the present invention can be obtained by preforming the unvulcanized composition into a desired shape by means of various forming techniques usually using a forming apparatus, such as extrusion molding machine, calendering rolls, press, injection molding machine or transfermolding machine and heating the preformed green product at the same time with the preforming or after the green product is guided in a vulcanization vessel or irradiating the preformed green product with electron beam to attain vulcanization. For foamed article, the unvulcanized composition which contains a foaming agent is subjected to vulcanization in the same manner as above, whereby foaming is caused simultaneously with the vulcanization and, thus, foamed product is obtained. The process herein is also the same as in the case of the second composition described later.

The vulcanized rubber product formed and vulcanized in this manner can be used for the same application as in the case of the second composition described later.

In case the formed product made from the first composition according to the present invention is a sheet or a film, it may be a laminate in which another layer made of other rubber or resin is laminated on a layer made of the first composition according to the present invention to build up a composite sheet or film. As the material for such another layer, there may be employed, for example, a rubber based on conjugated diene, a copolymer rubber based on ethylene/α-olefin, polyethylene, polypropylene or polybutene.

The first copolymer (I-1) according to the present invention, i.e. the α-olefin/triene random copolymer, can be used in a form of a resin composition by blending it with resin(s), for example, polyolefin resins, such as polyethylene, polypropylene and polybutene; resins, such as AES and ABS. Here, the conditions of blending proportion, other additives, such as softening ingredients and so on, to be employed may be the same as in the case of the second composition according to the present invention described later. Also, the cross linking agent and the cross linking method to be employed may be the same as in the case of the second composition described later.

Among the first copolymers according to the present invention, the second copolymer {ethylene/α-olefin/triene random copolymer (I-2)} and the third copolymer {α-olefin/triene random copolymer (I-3)}, as given below, are preferred.

Among the first compositions according to the present invention, the second composition (composition with ethylene/α-olefin/triene random copolymer) and the third composition (composition with α-olefin/triene random copolymer),as given below, are preferred.

The second copolymer (I-2) according to the present invention is an ethylene/α-olefin/triene random copolymer which comprises a structural unit ($U_{A-1}$) derived from ethylene (A-1),
a structural unit ($U_{A-2}$) derived from an α-olefin having 3–20 carbon atoms (A-2) and a structural unit ($U_{B-2}$) derived from the linear triene compound (B-2) represented by the formula (2), wherein the mole ratio of the structural unit ($U_{A-1}$) derived from ethylene (A-1) relative to the structural unit ($U_{A-2}$) derived from the α-olefin having 3–20 carbon atoms (A-2), namely ($U_{A-1}$)/($U_{A-2}$), is in the range from 99/1 to 30/70 and the intrinsic viscosity [η] determined in decalin at 135° C. is in the range from 0.1 to 10 dl/g, wherein the content of the structural unit ($U_{B-2}$) derived from the linear triene compound (B-2) represented by the formula (2) is in the range from 0.1 to 30 mole %.

The second composition according to the present invention (composition with ethylene/α-olefin/triene random copolymer), comprises the ethylene/α-olefin/triene random copolymer (I-2) mentioned above, a vulcanizing agent (II) and/or a filler (III).

The third copolymer (I-3) according to the present invention, i.e. an α-olefin/triene random copolymer, has a content of the structural unit ($U_{A-2}$) derived from the α-olefin having 3–20 carbon atoms (A-2) in the range from 70–99.9 mole %, a content of the structural unit derived from the α-olefin having 2–20 carbon atoms (A-3) in the range from 0 to 30 mole % and a content of the structural unit ($U_{B-2}$) derived from the linear triene compound (B-2) represented by the formula (2) in the range from 0.1 to 30 mole %, provided that the total sum of the contents of these structural units ($U_{A-2}$)+($U_{A-3}$)+($U_{B-2}$) amounts to 100 mole %, wherein the intrinsic viscosity [η] thereof determined in decalin at 135° C. is in the range from 0.1 to 10 dl/g.

The third composition according to the present invention (composition with α-olefin/triene random copolymer) comprises the α-olefin/triene random copolymer (I-3) mentioned above, a vulcanizing agent (II) and/or a filler (III).

Now, the description is directed to the second copolymer which is a preferable copolymer among the copolymers according to the present invention.

As the α-olefins having 3–20 carbon atoms (A-2) constituting the second copolymer (I-2), i.e. an ethylene/α-olefin/triene random copolymer, there may concretely be exemplified propylene, 1-butene, 1-pentene, 1-hexene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 1-octene, 1-decene, 1-dodecene, 1-tetradecene, 1-hexadecene, 1-octadecene and 1-eicosene. Among them, those α-olefins having 3–8 carbon atoms, such as propylene, 1-butene, 1-hexene and 1-octene are preferred.

Among the linear triene compounds (B-2) represented by the formula (2), those in which both $R^3$ and $R^4$ represent methyl are preferred. The second copolymer (I-2) according to the present invention, i.e. the ethylene/α-olefin/triene random copolymer, obtained using such linear triene compound (B-2) as the starting monomer, is particularly superior in the balance between the vulcanization velocity and the scorching profile.

As the linear triene compound (B-2) represented by the formula (2), 4,8-dimethyl-1,4,8-decatriene (in the following, sometimes abbreviated as DMDT) is preferred.

The linear triene compound (B-2) represented by the formula (2) has usually a stereoisomerism (trans- and cis-isomers). The linear triene compound (B-2) to be used as a comonomer may be either a mixture of trans- and cis-isomers or each sole isomer of trans- or cis-structure.

In the second copolymer (I-2) according to the present invention, i.e. an ethylene/α-olefin/triene random copolymer, the structural units derived from ethylene (A-1), from the α-olefin having 3–20 carbon atoms (A-2) and from the linear triene compound (B-2) are present in a random distribution and therein are present unsaturation bonds inherited from the linear triene compound (B-2) represented by the formula (2). The main chain of the second polymer (I-2) according to the present invention, i.e. the ethylene/α-olefin/triene random copolymer, has substantially a linear structure. The assumption that the second copolymer (I-2), i.e. the ethylene/α-olefin/triene random copolymer, has substantially a linear structure and does not substantially contain a cross-linked gelled molecular structure can be ascertained by the fact that this copolymer dissolves in an organic solvent without exhibiting any insoluble residue. For example, this can be ascertained by the fact that the copolymer (I-2) dissolves completely in decalin at 135° C. on the determination of its intrinsic viscosity [η].

In the second copolymer (I-2) according to the present invention, i.e. the ethylene/α-olefin/triene random copolymer, the mole ratio of the structural unit $(U_{A-1})$ derived from ethylene (A-1) relative to the structural unit $(U_{A-2})$ derived from the α-olefin (A-2), namely, $(U_{A-1})/(U_{A-2})$, which may be denoted sometimes in the following as the "lethylene/α-olefin", is in the range from 99/1 to 30/70, preferably from 90/10 to 50/50. When this mole ratio is in the above range, the second copolymer (I-2) according to the present invention, i.e. the ethylene/α-olefin/triene random copolymer, exhibits a favorable rubbery material properties.

The second copolymer (I-2) according to the present invention, i.e. the ethylene/α-olefin/triene random copolymer, can be utilized for applications including starting material for various rubber products and resin modifiers and can be used favorably for the starting material of rubbers for extrusion molded articles, such as glass run channel, wiper blade and weather strip sponge; for injection molded articles, such as in-mold foamed sponge articles; and for transfer-molded articles.

For using the second copolymer (I-2) according to the present invention, i.e. the ethylene/α-olefin/triene random copolymer, as the starting rubber for the production of glass run channel, the mole ratio of ethylene/α-olefin may especially favorably be in a range from 85/15 to 50/50, in particular, from 80/20 to 65/35. When this mole ratio is in the above range, a glass run channel especially superior in the rubbery elasticity and in the low-temperature flexibility can be obtained.

For using the second copolymer (I-2) according to the present invention, i.e. the ethylene/α-olefin/triene random copolymer, as the starting rubber for the production of wiper blade, the mole ratio of ethylene/α-olefin may especially favorably be in a range from 80/20 to 60/40, in particular, from 80/20 to 70/30. When this mole ratio is in the above range, a wiper blade especially superior in the rubbery elasticity and in the low-temperature flexibility can be obtained.

For using the second copolymer (I-2) according to the present invention, i.e. the ethylene/α-olefin/triene random copolymer, as the starting rubber for the production of sponge rubber weather strip, the mole ratio of ethylene/α-olefin may especially favorably be in a range from 85/15 to 60/40, in particular, from 80/20 to 65/35. When this mole ratio is in the above range, a weather strip especially superior in the rubbery elasticity and in the low-temperature flexibility can be obtained.

For using the second copolymer (I-2) according to the present invention, i.e. the ethylene/α-olefin/triene random copolymer, as the starting rubber for the production of sponge rubber in-mold foaming-molded articles using an injection molding machine or transfer molding machine, the mole ratio of ethylene/α-olefin may especially favorably be in a range from 80/20 to 60/40, in particular, from 80/20 to 70/30. When this mole ratio is in the above range, sponge rubber articles especially superior in the rubbery elasticity and in the low-temperature flexibility can be obtained.

The second copolymer (I-2) according to the present invention, i.e. the ethylene/α-olefin/triene random copolymer, has a content of the structural unit $(U_{B-2})$ derived from the linear triene compound (B-2) represented by the formula (2) in a range from 0.1 to 30 mole %, preferably from 0.5 to 10 mole %. When the content of the structural unit $(U_{B-2})$ derived from the linear triene compound (B-2) is in the above range, the second copolymer (I-2) according to the present invention, i.e. the ethylene/α-olefin/triene random copolymer, exhibits a high vulcanization velocity and a superior scorch stability.

For using the second copolymer (I-2) according to the present invention, i.e. the ethylene/α-olefin/triene random copolymer, as the starting rubber for the production of glass run channel, the content of the structural unit $(U_{B-2})$ derived from the linear triene compound (B-2) may especially favorably be in a range from 0.5 to 3.7 mole %, in particular, from 1.3 to 3.3 mole %. When the content of the structural unit $(U_{B-2})$ derived from the linear triene compound (B-2) is in the above range, a glass run channel especially superior in the rubbery elasticity and in the low-temperature flexibility can be obtained. When the content of the structural unit $(U_{B-2})$ derived from the linear triene compound (B-2) is in the above-mentioned range, the iodine value may usually be in the range from 10 to 50, preferably from 20 to 45.

For using the second copolymer (I-2) according to the present invention, i.e. the ethylene/α-olefin/triene random copolymer, as the starting rubber for the production of wiper blade, the content of the structural unit $(U_{B-2})$ derived from the linear triene compound (B-2) may especially favorably be in a range from 0.3 to 2.8 mole %, in particular, from 0.5 to 2.8 mole %. When the content of the structural unit $(U_{B-2})$ derived from the linear triene compound (B-2) is in the above-mentioned range, a wiper blade especially superior in the rubbery elasticity and in the low-temperature flexibility can be obtained. When the content of the structural unit $(U_{B-2})$ derived from the linear triene compound (B-2) is in the above-mentioned range, the iodine value may usually be in the range from 5 to 40, preferably from 10 to 40.

For using the second copolymer (I-2) according to the present invention, i.e. the ethylene/α-olefin/triene random copolymer, as the starting rubber for the production of sponge rubber weather strip, the content of the structural unit $(U_{B-2})$ derived from the linear triene compound (B-2) may especially favorably be in a range from 0.5 to 3.7 mole %, in particular, from 1.3 to 3.3 mole %. When the content of the structural unit $(U_{B-2})$ derived from the linear triene compound (B-2) is in the above-mentioned range, a weather strip especially superior in the rubbery elasticity and in the low-temperature flexibility can be obtained. When the content of the structural unit $(U_{B-2})$ derived from the linear triene compound (B-2) is in the above-mentioned range, the iodine value may usually be in the range from 10 to 50, preferably from 20 to 45.

For using the second copolymer (I-2) according to the present invention, i.e. the ethylene/α-olefin/triene random copolymer, as the starting rubber for the production of sponge rubber in-mold foaming-molded articles using an injection molding machine or transfer molding machine, the content of the structural unit $(U_{B-2})$ derived from the linear triene compound (B-2) may especially favorably be in a range from 0.5 to 3.7 mole %, in particular, from 1.3 to 3.3 mole %. When the content of the structural unit ($U_{B-2}$) derived from the linear triene compound (B-2) is in the above-mentioned range, a sponge rubber in-mold foamed articles especially superior in the rubbery elasticity and in the low-temperature flexibility can be obtained. When the content of the structural unit ($U_{B-2}$) derived from the linear triene compound (B-2) is in the above-mentioned range, the iodine value may usually be in the range from 10 to 50, preferably from 20 to 45.

The second copolymer (I-2) according to the present invention, i.e. the ethylene/α-olefin/triene random copolymer, has an intrinsic viscosity [η] determined in decalin at 135° C. in the range of 0.1–10 dl/g, preferably from 0.5 to 5 dl/g. When the intrinsic viscosity [η] is in the above range, the second copolymer (I-2) according to the present invention, i.e. the ethylene/α-olefin/triene random copolymer, exhibits a high vulcanization velocity and a superior scorch stability.

For using the second copolymer (I-2) according to the present invention, i.e. the ethylene/α-olefin/triene random copolymer, as the starting rubber for the production of glass run channel, the intrinsic viscosity [η] may especially favorably be in a range from 1.2 to 4.5 dl/g, in particular, from 2.0 to 3.5 dl/g. When the intrinsic viscosity [η] is in the above range, a glass run channel especially superior in the balance between the processibility and the strength can be obtained.

For using the second copolymer (I-2) according to the present invention, i.e. the ethylene/α-olefin/triene random copolymer, as the starting rubber for the production of wiper blade, the intrinsic viscosity [η] may especially favorably be in a range from 0.7 to 4.5 dl/g, in particular, from 1.5 to 3.3 dl/g. When the intrinsic viscosity [η] is in the above range, a wiper blade especially superior in the balance between the processibility and the strength can be obtained.

For using the second copolymer (I-2) according to the present invention, i.e. the ethylene/α-olefin/triene random copolymer, as the starting rubber for the production of sponge rubber weather strip, the intrinsic viscosity [η] may especially favorably be in a range from 1.2 to 5.0 dl/g, in particular, from 2.0 to 4.5 dl/g. When the intrinsic viscosity [η] is in the above range, a weather strip especially superior in the balance between the high packing degree and the strength can be obtained.

For using the second copolymer (I-2) according to the present invention, i.e. the ethylene/α-olefin/triene random copolymer, as the starting rubber for the production of sponge rubber in-mold foaming-molded articles using an injection molding machine or transfer molding machine, the intrinsic viscosity [η] may especially favorably be in a range from 0.5 to 2.0 dl/g, in particular, from 0.7 to 1.4 dl/g. When the intrinsic viscosity [η] is in the above range, in-mold foaming-molded articles especially superior in the flowability in the mold can be obtained.

In the second copolymer (I-2) according to the present invention, i.e. the ethylene/α-olefin/triene random copolymer, the structural unit ($U_{B-2}$) derived from the linear triene compound (B-2) has a structure represented substantially by the following formula (2-a), (2-a)

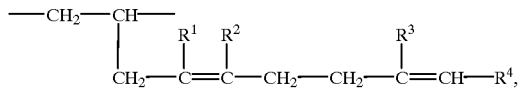

in which $R^1$ and $R^2$ represent each, independently of each other, hydrogen atom, methyl or ethyl and $R^3$ and $R^4$ stand each, independently of each other, methyl or ethyl.

The fact that the structural unit ($U_{B-2}$) derived from the linear triene compound (B-2) has the molecular structure represented by the above formula (2-a) can be confirmed by inspecting the second copolymer (I-2) by $^{13}$C-NMR spectrometry.

The second copolymer (I-2) according to the present invention, i.e. the ethylene/α-olefin/triene random copolymer, may have a structural unit derived from other compound(s) as comonomer(s), capable of being co-polymerized with ethylene (A-1), the α-olefin having 3–20 carbon atoms (A-2) and the linear triene compound (B-2). For such other comonomers, there may be exemplified non-conjugated dienes and cyclic olefins. The content of the structural units derived from such other comonomer(s) may be 30 mole % or less, preferably 0.5–10 mole %, with respect to the total structural units for all the comonomers.

As the non-conjugated dienes for such other comonomer, there may be enumerated those in which two polymerizable carbon-to-carbon double bonds (C=C) among the entire carbon-to-carbon double bonds are present in the molecule or those in which only one polymerizable carbon-to-carbon double bond among the entire carbon-to-carbon double bonds is present in the molecule. Here, the "polymerizable carbon-to-carbon double bond" does mean the carbon-to-carbon double bond which can serve for the polymerization in the presence of the catalyst to be employed in the production of the second copolymer (I-2) according to the present invention, i.e. the ethylene/α-olefin/triene random copolymer.

By co-polymerizing a non-conjugated diene, control of the vulcanization velocity can be attained. When a non-conjugated diene having two polymerizable carbon-to-carbon double bonds in the molecule is co-polymerized, a long chain branching is introduced, whereby the moldability is increased.

Concrete examples of the non-conjugated diene to be used as other comonomer which has two polymerizable carbon-to-carbon double bonds in the molecule include 5-alkenyl-2-norbornenes, such as 5-vinyl-2-norbornene and 5-allyl-2-norbornene; cycloaliphatic dienes, such as 2,5-norbornadiene, dicyclopentadiene and tetracyclo[4.4.0.1$^{2,}$ $^5$.1$^{7,10}$]deca-3,8-diene; and a, ω-dienes, such as 1,7-octadiene and 1,9-decadiene. Among them, 5-alkenyl-2-norbornenes, 2,5-norbornadiene, dicyclopentadiene and 1,7-octadiene are preferred, wherein special preference is given to 5-alkenyl-2-norbornenes and 2,5-norbornadiene.

As the non-conjugated dienes having only one polymerizable carbon-to-carbon double bond in the molecule to be used as other comonomer, those in which only one carbon-to-carbon double bond is present at one end of the molecule as a vinyl group ($CH_2=CH-$) and other carbon-to-carbon double bonds are present in the molecular chain (inclusive of the main chain and side chain) in a form of internal olefin structure are preferred. As the non-conjugated dienes having only one polymerizable carbon-to-carbon double bond, there may be enumerated aliphatic dienes and alicyclic dienes having an alicyclic moiety in which one carbon-to-carbon double bond is present and a linear chain moiety in which internal olefinic carbon-to-carbon double bond(s) are present. Among them, alicyclic dienes are preferred.

Concrete examples of the aliphatic dienes having in the molecule only one polymerizable carbon-to-carbon double bond to be used as other comonomer include 1,4-hexadiene, 1,6-octadiene, 3-methyl-1,4-hexadiene, 4-methyl-1,4-hexadiene, 5-methyl-1,4-hexadiene, 4-ethyl-1,4-hexadiene, 3-methyl-1,5-hexadiene, 3,3-dimethyl-1,4-hexadiene, 5-methyl-1,4-heptadiene, 5-ethyl-1,4-hepta-diene, 5-methyl-1,5-heptadiene, 6-methyl-1,5-heptadiene, 5-ethyl-1,5-heptadiene, 4-methyl-1,4-octadiene, 5-methyl-1,4-octadiene, 4-ethyl-1,4-octadiene, 5-ethyl-1,4-octadiene, 5-methyl-1,5-octadiene, 6-methyl-1,5-octadiene, 5-ethyl-1,5-octadiene, 6-ethyl-1,5-octadiene, 6-methyl-1,6-octadiene, 7-methyl-1,6-octadiene, 6-ethyl-1,6-octadiene, 6-propyl-1,6-octadiene, 6-butyl-1,6-octa-diene, 4-methyl-1,4-nonadiene, 5-methyl-1,4-nonadiene, 4-ethyl-1,4-nonadiene, 5-ethyl-1,4-nonadiene, 5-methyl-1,5-nonadiene, 6-methyl-1,5-nonadiene, 5-ethyl-1,5-nona-diene, 6-ethyl-1,5-nonadiene, 6-methyl-1,6-nonadiene, 7-methyl-1,6-nonadiene, 6-ethyl-1,6-nonadiene, 7-ethyl-1,6-nonadiene, 7-methyl-1,7-nonadiene, 8-methyl-1,7-nonadiene, 7-ethyl-1,7-nonadiene, 5-methyl-1,4-deca-diene, 5-ethyl-1,4-decadiene, 5-methyl-1,5-decadiene, 6-methyl-1,5-decadiene, 5-ethyl-1,5-decadiene, 6-ethyl-1,5-decadiene, 6-methyl-1,6-decadiene, 6-ethyl-1,6-deca-diene, 7-methyl-1,6-decadiene, 7-ethyl-1,6-decadiene, 7-methyl-1,7-decadiene, 8-methyl-1,7-decadiene, 7-ethyl-1,7-decadiene, 8-ethyl-1,7-decadiene, 8-methyl-1,8-deca-diene, 9-methyl-1,8-decadiene, 8-ethyl-1,8-decadiene, 6-methyl-1,6-undecadiene and 9-methyl-1,8-undecadiene.

Concrete examples of the alicyclic dienes having in the molecule only one polymerizable carbon-to-carbon double bond to be used as other comonomer include norbornene derivatives, such as 5-ethylidene-2-norbornene, 5-propylidene-2-norbornene and 5-butylidene-2-norbornene; and norbornadiene derivatives, such as 2-methyl-2,5-norbornadiene and 2-ethyl-2,5-norbornadiene. Among them, 5-ethylidene-2-norbornene is preferred.

There may be incorporated only one or a plurality of such non-conjugated dienes as other comonomer.

As the cyclic olefin to be used as other comonomer, there may be enumerated those which are represented by the following formulae (7-1) and (7-2), (7-1)

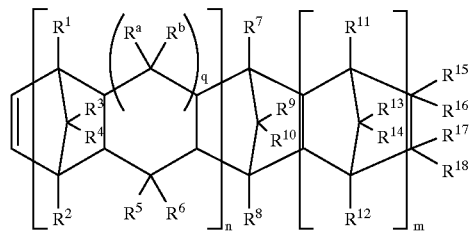

(7-2)

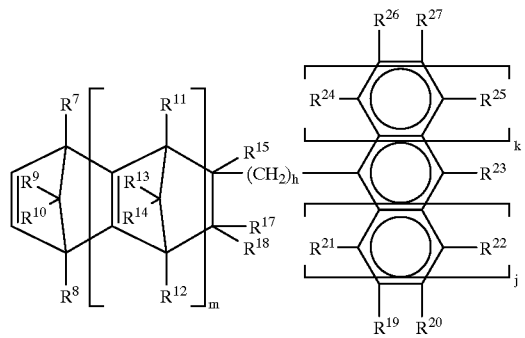

In the above formula (7-1), n is 0 or 1, m is zero or a positive integer, q is zero or 1, $R^1$–$R^{18}$ as well as $R^a$ and $R^b$ represent each, independently of each other, an atom or a radical selected from the group consisting of hydrogen atom, halogen atoms and hydrocarbon groups, wherein $R^{15}$ and $R^{16}$ may couple together to form a monocyclic or polycyclic ring which may have double bond(s) or the groups $R^{15}$ and $R^{16}$ or the groups $R^{17}$ and $R^{18}$ may form an alkylidene. In case q equals to zero, the bonds may fuse together to form a 5 membered ring.

In the above formula (7-2), m is zero or a positive integer, h is zero or a positive integer, j and k are each zero, 1 or 2, $R^7$–$R^{15}$ and $R^{18}$ and $R^{18}$ represent each, independently of each other, an atom or a radical selected from the group consisting of hydrogen atom, halogen atoms and hydrocarbon groups, wherein $R^{19}$ to $R^{27}$ represent each, independently of each other, an atom or a radical selected from hydrogen atom, halogen atoms, hydrocarbon groups and alkoxyl groups.

In the above formula (7-1), $R^1$–$R^{18}$ as well as $R^a$ and $R^b$ represent each, independently of each other, an atom or a radical selected from the group consisting of hydrogen atom, halogen atoms and hydrocarbon groups.

Here, the halogen atom is fluorine, chlorine, bromine or iodine.

As the hydrocarbon groups, there may be enumerated, for example, alkyl groups having 1–20 carbon atoms, halogenated alkyl groups having 1–20 carbon atoms, cycloalkyl groups having 3–15 carbon atoms and aromatic hydrocarbon groups havig 6–20 carbon atoms. More concretely, the alkyl groups may be, for example, methyl, ethyl, propyl, isopropyl, amyl, hexyl, octyl, decyl, dodecyl and octadecyl.

The halogenated alkyl groups may be those in which the hydrogen atoms in the aklyl group are substituted at least partly by fluorine atom, chlorine atom, bromine atom or iodine atom.

The cycloalkyl groups may include, for example, cyclohexyl and the like. The aromatic hydrocarbon groups may include, for example, phenyl, naphthyl and so on.

It is permissible also that a monocyclic ring or a polycyclic ring may be formed by the combination (with each other) of each of the pairs consisting of $R^{15}$ with $R^{16}$, $R^{17}$ with $R^{18}$, $R^{15}$ with $R^{17}$, $R^{16}$ with $R^{18}$, $R^{15}$ with $R^{18}$ and $R^{16}$ with $R^{17}$ in the formula (7-1), respectively, wherein the monocyclic or polycyclic ring formed in this manner may have double bond(s). As the monocyclic or polycyclic ring thus formed, concretely the followings may be exemplified:

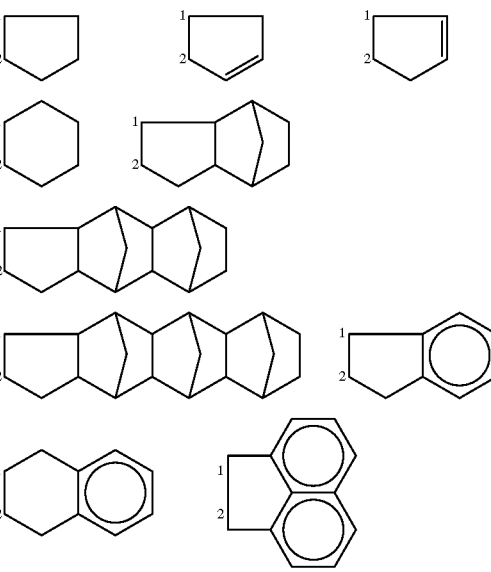

In the above exemplifications, the carbon atom marked with a numeral 1 or 2 indicates that carbon atom to which either $R^{15}(R^{16})$ or $R^{17}(R^{18})$ of the formula (7-1) is combined.

Further, it is also possible that an alkylidene group may be formed under the combination of either $R^{15}$ with $R^{16}$ or $R^{17}$ with $R^{18}$. Such alkylidene groups may, in general, have 2–20 carbon atoms and concrete examples therefor include ethylidene, propylidene and isopropylidene.

As preferred cycloolefin among those represented by the formula (7-1), those expressed by the following formula (7-3) may be enumerated:

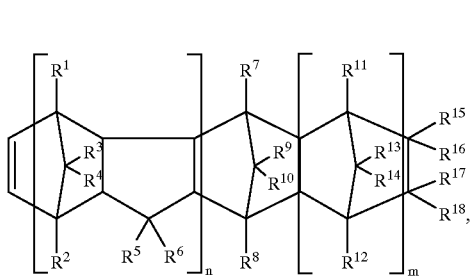

(7-3)

wherein n, m and $R^1$–$R^{18}$ are the same as those of the formula (7-1).

In the formula (7-2), m and h are each 0 or a positive integer, j and k are each 0, 1 or 2, $R^7$–$R^{15}$ as well as $R^{17}$–$R^{18}$ are the same as those of the formula (7-1) and $R^{19}$–$R^{27}$ denote each, independently of each other, an atom or a radical selected from the group consisting of hydrogen atom, halogen atoms, hydrocarbon groups and alkoxy groups.

The halogen atoms herein are the same as those of the formula (7-1).

As the hydrocarbon groups of $R^{19}$–$R^{27}$ of the general formula (7-2), there may be enumerated alkyl groups having 1–20 carbon atoms, halogenated alkyl groups having 1–20 carbon atoms, cycloalkyl groups having 3–15 carbon atoms and aromatic hydrocarbon groups having 6–20 carbon atoms. Concrete examples include, for the alkyl group, methyl, ethyl, propyl, isopropyl, amyl, hexyl, octyl, decyl, dodecyl and octadecyl; and for the halogenated alkylgroup, those in which at least a part of hydrogen atoms in the above-exemplified alkyl groups is replaced by fluorine atom, chlorine atom, bromine atom or iodine atom.

For the cycloalkyl group, cyclohexyl and the like are exemplified. The aromatic hydrocarbon group may comprise aryl groups, aralkyl groups and so on, concrete examples of which include phenyl, tolyl, naphthyl, benzyl and phenyl ethyl. For the alkoxy group, there may be enumerated methoxy, ethoxy and propoxy. It is permissible here, that the carbon atom to which $R^{17}$ and $R^{18}$ are combined is bound directly or under intermediation by an alkylene group having 1–3 carbon atoms to the carbon atom to which $R^{21}$ is combined or to the carbon atom to which $R^{19}$ is combined. Thus, in case the two carbon atoms mentioned above are bound under intermediation by an alkylene group, the radicals represented by $R^{17}$ and $R^{21}$, respectively, or the radicals represented by $R^{18}$ and $R^{19}$, respectively, will form together an alkylene group selected among methylene (—$CH_2$—), ethylene (—$CH_2CH_2$—) and trimethylene (—$CH_2CH_2CH_2$—).

Moreover, in the case of j=k=0, the radical pair $R^{23}$ with $R^{20}$ or $R^{23}$ with $R^{27}$ may form a monocyclic or polycyclic aromatic ring by combining with each other. Examples of the monocyclic or polycyclic aromatic ring in case the radical pair $R^{23}$ with $R^{20}$ forms an aromatic ring, when j=k=0, include the groups given below.

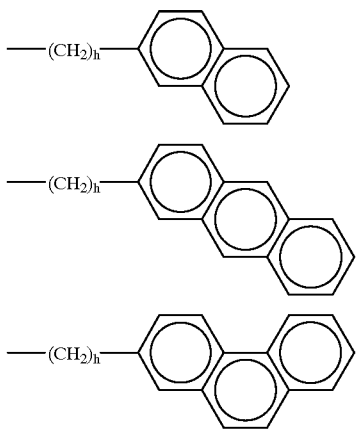

In the above exemplified formulae, the symbol h is the same as that in the formula (7-2).

Concrete examples of the cycloolefin represented by the formulae (7-1) and (7-2) are:

bicyclo[2.2.1]hept-2-ene or its derivative,
tetracyclo[4.4.0.$1^{2,5}$.$1^{7,10}$]-3-dodecene or its derivative,
hexacyclo[6.6.1.$1^{3,6}$.$1^{10,13}$.$0^{2,7}$.$0^{9,14}$]-4-heptadecene or its derivative,
octacyclo[8.8.0.$1^{2,9}$.$1^{4,7}$.$1^{11,18}$.$1^{13,16}$.$0^{3,6}$.$0^{12,17}$]-5-docosene or its derivative,
pentacyclo[6.6.1.$1^{3,6}$.$0^{2,7}$.$0^{9,14}$]-4-hexadecene or its derivative,
heptacyclo-5-eicosene or its derivative,
heptacyclo-5-heneicosene or its derivative,
tricyclo[4.3.0.$1^{2,5}$]-3-decene or its derivative,
tricyclo[1.4.0.$1^{2,5}$]-3-undecene or its derivative,
pentacyclo[6.5.1.$1^{3,5}$.$0^{2,7}$.$0^{3,13}$]-4-pentadecene or its derivative,
pentacyclopentadecadiene or its derivative,
pentacyclo[7.4.0.$1^{2,5}$.$1^{9,12}$.$0^{8,13}$]-3-pentadecene or its derivative,
heptacyclo[8.7.0.$1^{3,6}$.$1^{10,17}$.$1^{12,15}$.$0^{2,7}$.$0^{11,16}$]-4-eicosene or its derivative,
nonacyclo[10.9.1.$1^{4,7}$.$1^{13,20}$.$1^{15,18}$.$0^{3,8}$.$0^{2,10}$.$0^{12,21}$.$0^{14,19}$]-5-pentacosene or its derivative,
pentacyclo[8.4.0.$1^{2,5}$.$1^{9,12}$.$0^{8,13}$]-3-hexadecene or its derivative,
heptacyclo[8.8.0.$1^{4,7}$.$1^{11,18}$.$1^{13,16}$.$0^{3,8}$.$0^{12,17}$]-5-heneicosene or its derivative,
nonacyclo[10.10.1.$1^{5,8}$.$1^{14,21}$.$1^{16,19}$.$0^{2,11}$.$0^{4,9}$.$0^{13,22}$.$0^{15,20}$]-5-hexacosene or its derivative,
1,4-methano-1,4,4a,9a-tetrahydrofluorene or its derivative,
1,4-methano-1,4,4a,5,10,10a-hexahydroanthracene or its derivative and
cyclopentadiene-acenaphthylene adducts.

The cycloolefins represented by the general formulae (7-1) and (7-2) can be produced by subjecting cyclopentadiene and an olefin compound of corresponding molecular structure to Diels-Alder reaction.

These cycloolefins can be employed solely or in combination of two or more of them.

The second copolymer (I-2) according to the present invention, i.e. the ethylene/α-olefin/triene random copolymer, can be vulcanized at high velocity and is superior in the scorch stability, together with supriority in weatherability, heat resistance and fastness to ozone.

The second copolymer (I-2) according to the present invention, i.e. the ethylene/α-olefin/triene random copolymer, may be brought into practical use not only in the unvulcanized state as such but also in the vulcanized form by subjecting it to vulcanization by the technique described afterwards, wherein development of the advantageous characteristic features thereof is facilitated by vulcanization. On vulcanization, a high vulcanization velocity is attained, though the term till scorching is not reduced.

The second copolymer (I-2) according to the present invention, i.e. the ethylene/α-olefin/triene random copolymer, can be used especially favorably for the starting material for various rubber products and as a resin modifier.

As the rubber products, there may be exemplified automobile parts, industrial rubber products, electric insulator, articles for constructional uses and rubber-lined cloth. Concrete examples include glass run channel, wiper blade, weather strip, sponge, hoses, grommet, side wall of tire, sheath for electric cable and gasket.

When the second copolymer (I-2) according to the present invention, i.e. the ethylene/α-olefin/triene random copolymer, is added as a resin modifier to resins, such as polypropylene, polyethylene, polybutene and polystyrene, the shock resistance and the resistance to stress cracking of the resin can be increased greatly.

The second copolymer (I-2) according to the present invention, i.e. the ethylene/α-olefin/triene random copolymer, may be vulcanized solely or co-vulcanized together with other rubber material.

The second copolymer (I-2) according to the present invention, i.e. the ethylene/α-olefin/triene random copolymer, can, due to its high vulcanization velocity, be vulcanized within a more short vulcanization time or at a lower vulcanization temperature without using a large amount of vulcanizing agent, as compared with conventional unsaturated copolymers based on olefin. The second copolymer (I-2) according to the present invention, i.e. the ethylene/α-olefin/triene random copolymer, has a superior scorch stability, so that it can be processed by foaming molding with a stable foaming expansion ratio and, thus, an increased productivity of foamed article can be attained. Thus, the foaming expansion ratio is determined by a delicate balance between the initial viscosity of the raw resin material, the rate of elevation of the viscosity during the molding and the rate of decomposition of the foaming agent, so that control of the expansion ratio is difficult, since the higher the viscosity elevation rate, the greater will be the variation in the viscosity change rate. However, the scorch stability is superior and, thus, the viscosity elevation is lower in the second copolymer (I-2) according to the present invention, i.e. the ethylene/α-olefin/triene random copolymer, so that it permits to produce a foamed molded article efficiently at a stable foaming expansion ratio. The second copolymer (I-2) according to the present invention, i.e. the ethylene/α-olefin/triene random copolymer, is superior also in the processing stability during working on an extruder due to its superior scorch stability and, therefore, any troublesome phenomenon caused from viscosity increase upon working, for example, on an extruder, such as reduction in the extrusion output, increase in the motor load and stuffing or clogging of the cylinder and/or die due to elevation of the viscosity by the progress of vulcanization within the extruder, can be prevented.

It is a further advantageous feature of the second copolymer (I-2) according to the present invention, i.e. the ethylene/α-olefin/triene random copolymer, that it excells in the fastness to thermal debasement while maintaining the superior characteristic features mentioned above.

<<Production of the Second Copolymer (I-2), i.e. the Ethylene/α-Olefin/Triene Random Copolymer>>

The second copolymer (I-2) according to the present invention, i.e. the ethylene/α-olefin/triene random copolymer, can be produced by co-polymerizing ethylene (A-1), the α-olefin having 3–20 carbon atoms (A-2), the linear triene compound (B-2) represented by the formula (2) and, if necessary, other comonomer(s) to be incorporated optionally, in the presence of a catalyst. As the catalyst, that comprising a transition metal compound (G) of, such as vanadium (V), zirconium (Zr) or titanium (Ti), and an organoaluminum or organoaluminum oxy-compound (H) and/or ionizing ionic compound (J) may be employed.

Concrete examples of the catalyst include
(1) a titanium catalyst composed of a solid titaniferous catalyst component (g-1) and an organoaluminum compound (h-1),
(2) a vanadium catalyst composed of a soluble vanadium compound (g-2) and an organoaluminum compound (h-1) and
(3) a metallocene catalyst composed of a metallocene of a transition metal selected from Group 4 of the periodic table and an organic aluminumoxy compound (h-2) and/or an ionizing ionic compound Among them, t he metallocene catalyst is preferred. The metallocene catalyst has a high catalytic activity and can produce the second copolymer (I-2) of the present invention, i.e. the ethylene/α-olefin/triene random copolymer, having narrow distributions for the molecular weight an d for the structural distribution with high conversion proportion of the linear triene compound (B-2) represented by the formula (2).

The solid titanium catalyst component (g-1) is prepared by bringing a titanium compound, a magnesium compound and an electron donor as given below into contact with each other.

As the titanium compound, a compound of trivalent or tetravalent titanium is employed, wherein tetravalent titanium compound is preferred. As the tetravalent titanium compound, for example, tetravalent titanium compounds represented by $Ti(OR)_jX_{4-j}$ (in which R is a hydrocarbon group, X is a halogen atom and $0 \leq j \leq 4$) may be enumerated. Among them, halogen-containing titanium compounds are preferred, wherein preference is given to titanium tetrahalides, especially titanium tetrachloride.

The magnesium compound to be used for preparing the solid titaniferous component (g-1) may be a magnesium compound which may or may not exhibit a reducing property. As the magnesium compound exhibiting a reducing property, those which have magnesium-to-carbon bond(s) and magnesium-to-hydrogen bond(s) may be enumerated. As the magnesium compound which does not exhibit reducing property, those which are derived from the above-mentioned reducible magnesium compounds or those which are derived upon the preparation of the catalyst component may be employed. It is also possible to use a complex, composite compound or a mixture composed of such a magnesium compound and other metal or metal compound. A mixture of two or more of such a magnesium compound may also be employed. As the magnesium compound, those which do not exhibit reducing property are preferred, with preference to halogen-containing ones, especially to magnesium chloride, an alkoxy magnesium chloride and an aryloxy magnesium chloride.

As the electron doner to be employed for preparing the solid titaniferous catalyst component (g-1), esters of organic carboxylic acids and esters of polybasic carboxylic acids may be enumerated.

The solid titaniferous catalyst component (g-1) can be prepared by bringing a titanium compound, a magnesium compound (or metallic magnesium) and an electron donor, as described above, into contact with each other. For preparing the solid titaniferous catalyst component (g-1), a known method for preparing a highly active titaniferous catalyst component from a titanium compound, a magnesium compound and an electron donor may be employed. On contacting the above three components, they can be brought into contact with each other in the presence of other reaction reagent, such as a compound of silicium, phosphorus or aluminum.

As the organoaluminum compound (h-1) for building up the catalyst based on titanium, compounds containing at least one Al-to-carbon bond in the molecule may be employed.

Examples of such compounds include organo-aluminum compounds represented by the formula (8-1), $$(R^1)_m Al(OR^2)_n H_p X_q \qquad (8\text{-}1),$$

in which $R^1$ and $R^2$ denote each a hydrocarbon group containing usually 1–15 carbon atoms, preferably 1–4 carbon atoms, which may be identical with or different from each other, X is a halogen atom, $0<m\leq 3$, $0\leq n<3$, $0\leq p<3$ and $0\leq q<3$, with $m+n+p+q=3$; and alkylated complexes of aluminum with a metal of Group 1 of the periodic table represented by the formula (8-2), $$(M^1)Al(R^1)_4 \qquad (8\text{-}2),$$

in which $M^1$ is Li, Na or K and $R^1$ has the same meaning as that in the formula (8-1).

For preparing the catalyst based on titanium, an electron donor may be incorporated on requirement. For such an electron donor, an organosilicic compound as represented by the formula (9) or (10) may be employed:

$$R_n Si(OR^1)_{4-n} \qquad (9)$$

$$SiR^1 R^2{}_m (OR^3)_{3-m} \qquad (10)$$

In the formula (9), R and $R^1$ denote each a hydrocarbon group and n is a number sufficing the condition $0<n<4$.

In the formula (10), $R^1$ denotes cyclopentyl or an alkyl-containing cyclopentyl, $R^2$ is an alkyl, a cyclopentyl or an alkyl-containing cyclopentyl, $R^3$ is a hydrocarbon group and m is a number sufficing the condition $0\leq m\leq 2$.

As the alkyl-containing cyclopentyl $R^1$ in the formula (10), for example, 2-methylcyclopentyl, 3-methylcyclopentyl, 2-ethylcyclopentyl and 2,3-dimethylcyclopentyl may be enumerated.

In the catalyst components for building up the catalyst based on titanium according to the present invention, an α-olefin may be incorporated under a prepolymerization. The prepolymerization may desirably be realized by using the α-olefin in an amount of 0.1–500 g, preferably 0.3–300 g, most preferably 1–100 g per 1 g of the olefin-polymerizing catalyst. The prepolymerization may preferably be effected by mixing the α-olefin and the catalyst component in an inert hydrocarbon solvent to cause the prepolymerization under a mild condition. The α-olefin to be employed in the prepolymerization may or may not be identical with that used for preparing the second copolymer (I-2), i.e. the ethylene/α-olefin/triene random copolymer.

As the soluble vanadium compound (g-2) for building up the catalyst based on vanadium to be employed according to the present invention, such compounds as represented by the following formulae (11) and (12) may be enumerated:

$$VO(OR)_a X_b \qquad (11)$$

$$V(OR)_c X_d \qquad (12)$$

In the formulae (11) and (12), R is a hydrocarbon group, X is a halogen atom and the symbols a, b, c and d represent each a number sufficing the conditions $0\leq a\leq 3$, $0\leq b\leq 3$, $2\leq a+b\leq 3$, $0\leq c\leq 4$, $0\leq d\leq 4$ and $3\leq c+d\leq 4$, respectively.

As the soluble vanadium compound (g-2), an electron donor adduct of a soluble vanadium compound obtained by contacting an electron donor with the soluble vanadium compound may be employed.

As the organoaluminum compound (h-1) for building up the catalyst based on vanadium, those which are the same as the organoaluminum compound (h-1) for building up the catalyst based on titanium mentioned above may be used.

The metallocene (g-3) to be employed for building up the catalyst based on metallocene according to the present invention is that of a transition metal selected from the elements of Group 4 of the periodic table. Concrete examples thereof include those represented by the following formula (13), $$ML_x \qquad (13),$$

in which M is a transition metal selected from the elements of Group 4 of the periodic table, x is the valency of the transition metal M and L represents a ligand.

Concrete examples of the transition metal represented by M in the formula (13) include zirconium, titanium and hafnium.

L in the formula (13) denotes a ligand to be coordinated to the transition metal. Among these ligands, at least one ligand L has a skeleton of cyclopentadienyl, which may have substituent group(s).

For the ligand L having a skeleton of cyclopentadienyl, there may be enumerated, for example, cyclopentadienyl group; alkyl- or cycloalkyl-substituted cyclopentadienyl group, such as, methylcyclopentadienyl group, ethylcyclopentadienyl group, n- or i-propylcyclopentadienyl group, n-, i-, sec- or t-butylcyclopentadienyl group, dimethylcyclopentadienyl group, methylpropylcyclopentadienyl group, methylbutylcyclopentadienyl group and methylbenzylcyclopentadienyl group; indenyl group; 4,5,6,7-tetrahydroindenyl group; and fluorenyl group.

The group having the cyclopentadienyl-skeleton mentioned above may have substituent(s) of, for example, a halogen atom or a trialkylsilyl group.

If the compound represented by the formula (13) has two or more groups having the skeleton of cyclopentadienyl as the ligand L, two of such groups having the skeleton of cyclopentadienyl may be bound together through a bridging group, for example, an alkylene, such as ethylene or propylene, a substituted alkylene, such as isopropylidene or diphenylmethylene, a silylene or a substituted silylene, such as dimethylsilylene, diphenylsilylene or methylphenylsilylene.

For the ligands L other than those having the skeleton of cyclopentadienyl, namely, those which do not possess the skeleton of cyclopentadienyl, there may be enumerated, for example, hydrocarbon groups having 1–12 carbon atoms, alkoxy groups, aryloxy groups, sulfo-containing groups ($-SO_3 R^a$ in which $R^a$ denotes an alkyl, a halogen-substituted alkyl, aryl or a halogen- or alkyl-substituted aryl), halogen atoms and hydrogen atom.

For the hydrocarbon groups containing 1–12 carbon atoms of the ligand L, for example, alkyl, cycloalkyl, aryl and aralkyl are enumerated. More concretely, they include alkyl groups, such as, methyl, ethyl, n-propyl, i-propyl, n-butyl, i-butyl, sec-butyl, t-butyl, pentyl, hexyl, octyl, decyl and dodecyl; cycloalkyl groups, such as, cyclopentyl and cyclohexyl; aryl groups, such as, phenyl and tolyl; and aralkyl groups, such as, benzyl and neophyl.

As the alkoxy groups for the ligand L, for example, methoxy, ethoxy and n-propoxy, are enumerated. As the aryloxy groups, for example, phenoxy etc., may be enumerated. As the sulfo-containing groups ($-SO_3R^a$), for example, methanesulfonato, p-toluenesulfonato, triflo-romethanesulfonato and p-chlorobenzenesulfonato are enumerated. As the halogen atom, for example, fluorine, chlorine, bromine and iodine are enumerated.

More concretely, the metallocene represented by the formula (13) in which the valency of the transition metal is four is represented by the following formula (14), $$R^2{}_k R^3{}_l R^4{}_m R^5{}_n M \qquad (14),$$

in which M is a transition metal defined in the formula (13), $R^2$ is a group (ligand) having the skeleton of cyclopentadienyl, $R^3$, $R^4$ and $R^5$ represent each, independently of each other, a group (ligand) which may or may not have the skeleton of cyclopentadienyl and k is an integer of at least 1, with k+l +m+n=4.

Below, examples of the metallocene (g-3) in which M is zirconium and which has at least two ligands having a cyclopentadienyl skeleton are recited:

Bis(cyclopentadienyl)zirconium monochloride monohydride

Bis(cyclopentadienyl)zirconium dichloride

Bis(1-methyl-3-butylcyclopentadienyl)zirconium bis-(trifluoromethanesulfonate)

Bis(1,3-dimethylcyclopentadienyl)zirconium dichloride

It is permissible according to the present invention to use a compound in which the above-mentioned 1,3-disubstituted cyclopentadienyl group is replaced by a 1,2-disubstituted cyclopentadienyl group.

Also, it is possible to use, for the metallocene (g-3), a bridged metallocene in which at least two of $R^2$, $R^3$, $R^4$ and $R^5$ in the formula (14), for example, $R^2$ and $R^3$, are a group (ligand) having a skeleton of cyclopentadienyl, wherein said at least two groups are bound together through a bridging group, such as an alkylene, substituted alkylene, silylene or substituted silylene. In such a case, the groups $R^4$ and $R^5$ are the same, independently of each other, as the ligands L other than that having cyclopentadienyl skeleton as mentioned previously for the formula (13).

Concrete examples of such bridged metallocenes (g-3) include ethylene bis(indenyl)dimethylzirconium, ethylene bis(indenyl)zirconium dichloride, isopropylidene(cyclopentadienyl-fluorenyl)zirconium dichloride, diphenylsilylene bis(indenyl)zirconium dichloride and methylphenylsilylene bis(indenyl)zirconium dichloride.

Also, as the metallocene (g-3), metallocenes disclosed in Japanese Patent Kokai Hei 4-268307 (corresponding to U.S. Pat. No. 5,243,001) represented by the following formula (15) may also be enumerated.

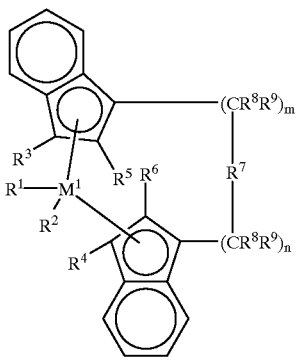

(15)

In the above formula (15), $M^1$ denotes a metal of Group 4 of the periodic table and may concretely be, for example, titanium, zirconium or hafnium.

In the formula (15), $R^1$ and $R^2$ may each be hydrogen atom, an alkyl having 1–10 carbon atoms, preferably 1–3 carbon atoms, an alkoxy having 1–10 carbon atoms, preferably 1–3 carbon atoms, an aryl group having 6–10 carbon atoms, preferably 6–8 carbon atoms, an aryloxy group having 6–10 carbon atoms, preferably 6–8 carbon atoms, an alkenyl group having 2–10 carbon atoms, preferably 2–4 carbon atoms, an aralkyl group having 7–40 carbon atoms, preferably 7–10 carbon atoms, an alkaryl group having 7–40 carbon atoms, preferably 7–12 carbon atoms, or an aralkenyl group having 8–40 carbon atoms, preferably 8–12 carbon atoms, or, further, a halogen atom, preferably chlorine atom. Here, $R^1$ and $R^2$ may or may not be identical with each other.

In the formula (15), $R^3$ and $R^4$ may each stand for hydrogen atom, a halogen atom, preferably fluorine atom, chlorine atom or bromine atom, an alkyl group which may be halogenated and which has 1–10 carbon atoms, preferably 1–4 carbon atoms, an aryl group having 6–10, preferably 6–8 carbon atoms, a group of $-N(R^{10})_2$, $-SR^{10}$, $-OSi(R^{10})_3$, $-Si(R^{10})_3$, or $-P(R^{10})_2$. Here, $R^{10}$ is a halogen atom, preferably chlorine atom, an alkyl group having 1–10 carbon atoms, preferably 1–3 carbon atoms, or an aryl group having 6–10 carbon atoms, preferably 6–8 carbon atoms. $R^3$ and $R^4$ may or may not be identical with each other. It is especially preferable that both $R^3$ and $R^4$ are hydrogen atom.

In the formula (15), $R^5$ and $R^6$ may be the same as $R^3$ and $R^4$ except hydrogen atom. $R^5$ and $R^6$ may or may not be identical with each other, while it is preferable that both are the same. $R^5$ and $R^6$ may each preferably be an alkyl group having 1–4 carbon atoms which may preferably be halogenated, of which concrete examples are methyl, ethyl, propyl, isopropyl, butyl, isobutyl and trifluoromethyl, wherein a particular preference is given to methyl.

In the general formula (15), $R^7$ may stand for:

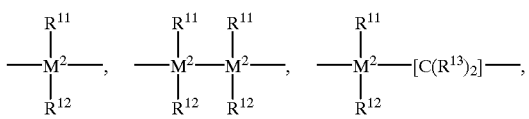

-continued

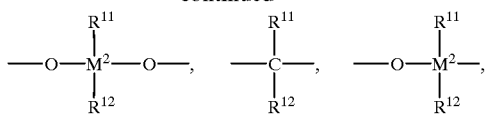

as well as =BR$^{11}$, =AlR$^{11}$, —Ge—, —Sn—, —O—, =SO, =SO$_2$, =NR$^{11}$, =CO, =PR$^{11}$ or =P(O)R$^{11}$. In the above, R$^{11}$, R$^{12}$ and R$^{13}$ may each stand for hydrogen atom; a halogen atom; an alkyl group having 1–10 carbon atoms, preferably 1–4 carbon atoms, and more preferably methyl; a fluoroalkyl group having 1–10 carbon atoms, preferably —CF$_3$; an aryl group having 6–10 carbon atoms, preferably 6–8 carbon atoms; a fluoroaryl group having 6–10 carbon atoms, preferably pentafluorophenyl; an alkoxy group having 1–10 carbon atoms, preferably 1–4 carbon atoms, in particular methoxy; an alkenyl group having 2–10 carbon atoms, preferably 2–4 carbon atoms; an aralkyl group having 7–40 carbon atoms, preferably 7–10 carbon atoms; an aralkenyl group having 8–40 carbon atoms, preferably 8–12 carbon atoms; or an alkaryl group having 7–40 carbon atoms, preferably 7–12 carbon atoms. The pair "R$^{11}$ with R$^{12}$" or "R$^{11}$ with R$^{13}$" may form a ring together with the atoms bound thereto. R$^{11}$, R$^{12}$ and R$^{13}$ may or may not be identical with each other.

M$^2$ may stand for silicium, germanium or tin, preferably silicium or germanium.

In the formula (15), R$^7$ may preferably stand for =CR$^{11}$R$^{12}$, =SiR$^{11}$R$^{12}$, =GeR$^{11}$R$^{12}$, —O—, —S—, =SO, =PR$^{11}$ or =P(O)R$^{11}$.

In the formula (15), R$^8$ and R$^9$ may each be the same as R$^{11}$, wherein R$^8$ and R$^9$ may or may not be identical with each other.

In the formula (15), m and n represent each 0, 1 or 2, preferably 0 or 1, with m+n being 0, 1 or 2, preferably 0 or 1. m and n may or may not be identical with each other.

As the metallocene (g-3) represented by the formula (15), the following compounds may be exemplified:

rac-ethylene(2-methyl-1-indenyl)-2-zirconium dichloride
rac-dimethylsilylene(2-methy-1-indenyl)-2-zirconium dichloride The metallocene (g-3) represented by the formula (15) can be produced by known methods (for example, Japanese Patent Kokai Hei 4-268307).

As the metallocene (g-3), one represented by the following formula (16) may also be used.

(16)

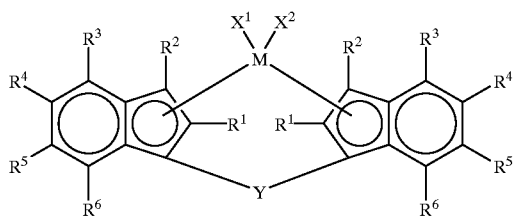

In the above formula (16), M denotes a transition metal atom of Group 4 of the periodic table, which may concretely be titanium, zirconium or hafnium.

In the formula (16), R$^1$ and R$^2$ stand, independently of each other, for hydrogen atom, a halogen atom, a hydrocarbon group having 1–20 carbon atoms, a halogenated hydrocarbon group having 1–20 carbon atoms, a silicium-containing group, a oxygen-containing group, a sulfur-containing group, a nitrogen-containing group or a phosphorus-containing group. Concrete examples of the group for R$^1$ and R$^2$ include:

a halogen atom, such as, fluorine, chlorine, bromine or iodine;

a hydrocarbon group having 1–20 carbon atoms, for example, an alkyl group, such as, methyl, ethyl, propyl, butyl, hexyl, cyclohexyl, octyl, nonyl, dodecyl, eicosyl, norbornyl or adamantyl, an alkenyl group, such as, vinyl, propenyl or cyclohexenyl, an aralkyl group, such as, benzyl, phenylethyl or phenylpropyl, or an aryl group, such as, phenyl, tolyl, dimethylphenyl, trimethylphenyl, ethylphenyl, propylphenyl, biphenyl, naphthyl, methylnaphthyl, anthracenyl or phenanthryl;

a halogenated hydrocarbon group having 1–20 carbon atoms of those in which the above-recited hydrocarbon groups are halogen-substituted;

a silicium-containing group, for example, a monohydrocarbon-substituted silyl, such as, methylsilyl or phenylsilyl, di-hydrocarbon-substituted silyl, such as, dimethylsilyl or diphenylsilyl, trihydrocarbon-substituted silyl, such as, trimethylsilyl, triethylsilyl, tripropylsilyl, tricyclohexylsilyl, triphenylsilyl, dimethylphenylsilyl, methyldiphenylsilyl, tritolylsilyl or trinaphthylsilyl, a silyl ether group of a hydrocarbon-substituted silyl, such as, trimethylsilyl ether group; a silicium-substituted hydrocarbon group, for example, a silicium-substituted alkyl, such as, trimethylsilylmethyl, or a silicium-substituted aryl, such as, trimethylsilylphenyl;

an oxygen-containing group, for example, hydroxy, an alkoxy group, such as, methoxy, ethoxy, propoxy or butoxy, an aryloxy group, such as, phenoxy, methylphenoxy, dimethylphenoxy or naphthoxy, or an aralkoxy group, such as, phenylmethoxy or phenylethoxy;

a sulfur-containing group, for example, a group of those in which the oxygen atom in the above-recited oxygen-containing groups is replaced by sulfur;

a nitrogen-containing group, for example, amino, an alkylamino, such as, methylamino, dimethylamino, diethylamino, dipropylamino, dibutylamino or dicyclohexylamino, an aryl- or alkylarylamino, such as, phenylamino, diphenylamino, ditolylamino, dinaphthylamino or methylphenylamino; and a phosphorus-containing group, for example, a phosphino, such as, dimethylphosphino or diphenylphosphino.

Among the above-recited groups for R$^1$, hydrocarbon groups are preferred, with particular preference being given to an alkyl group having 1–3 carbon atoms, such as, methyl, ethyl or propyl. R$^2$ may preferably stand for hydrogen atom or a hydrocarbon group, wherein a particular preference is given to hydrogen atom and alkyl groups having 1–3 carbon atoms, such as, methyl, ethyl and propyl.

In the formula (16), R$^3$, R$^4$, R$^5$ and R$^6$ denote, independently of each other, hydrogen atom, a halogen atom, a hydrocarbon group having 1–20 carbon atoms or a halogenated hydrocarbon group having 1–20 carbon atoms. Among them, hydrogen atom, hydrocarbon groups and halogenated hydrocarbon groups are preferred. Among the pairs R$^3$ with R$^4$, R$^4$ with R$^5$ and R$^5$ with R$^6$, at least one pair may form a monocyclic aromatic ring together with the carbon atoms bound thereto. If two or more hydrocarbon groups or halogenated hydrocarbon groups are present in the other pairs than that forming the aromatic ring, they may form a ring by combining together. It is preferable that $R^6$ is hydrogen atom, so long as it is not an aromatic substituent group.

For $R^3$, $R^4$, $R^5$ and $R^6$ in the formula (16), as the halogen atom, hydrocarbon group having 1–20 carbon atoms and halogenated hydrocarbon group having 1–20 carbon atoms, the same as those recited for $R^1$ and $R^2$ may be exemplified.

In the formula (16), $X^1$ and $X^2$ denote each, independently of each other, hydrogen atom, a halogen atom, a hydrocarbon group having 1–20 carbon atoms or a halogenated hydrocarbon group, oxygen-containing group or sulfur-containing group having 1–20 carbon atoms.

As the concrete examples of the halogen atom, the hydrocarbon groups having 1–20 carbon atoms and the halogenated hydrocarbon groups and oxygen-containing and sulfur-containing groups having 1–20 carbon atoms, those which are exemplified for $R^1$ and $R^2$ may be enumerated.

As the sulfur-containing groups, there may be exemplified those which are exemplified above for the groups $R^1$ and $R^2$; as well as sulfonates; such as methylsulfonate, trifluoromethanesufonate, phenylsulfonate, benzylsulfonate, p-toluenesulfonate, trimethylbenzenesulfonate triisobutylbenzenesulfonate, p-chlorobenzenesulfonate and pentafluorobenzenesulfonate; and sulfinates, such as methylsulfinate, phenylsulfinate, benzenesulfinate, p-toluenesulfinate, trimethylbenzenesulfinate and pentafluorobenzenesulfinate.

In the formula (16), Y denotes a divalent hydrocarbon group having 1–20 carbon atoms, a divalent halogenated hydrocarbon group having 1–20 carbon atoms, a divalent silicium-containing group, a divalent germanium-containing group, a divalent tin-containing group, the group —O—, —CO—, —S—, —SO—, —SO$_2$—, —NR$^7$—, —P(R$^7$)—, —P(O)(R$^7$)—, —BR$^7$— or —AlR$^7$—, with $R^7$ being hydrogen atom, a halogen atom, a hydrocarbyl having 1–20 carbon atoms or a halogenated hydrocarbyl having 1–20 carbon atoms.

Concrete examples of Y in the formula (16) include divalent hydrocarbon groups having 1–20 carbon atoms, for example, alkylenes, such as methylene, dimethylmethylene, 1,2-ethylene, dimethyl-1,2-ethylene, 1,3-trimethylene, 1,4-tetramethylene, 1,2-cyclohexylene and 1,4-cyclohexylene; and aralkylenes, such as diphenylmethylene and diphenyl-1,2-ethylene;

divalent halogenated hydrocarbon groups derived from divalent hydrocarbyls having 1–20 carbon atoms which are halogenated, such as chloromethylene and the like;

silicium-containing divalent groups, for example, alkylsilylenes, alkarylsilylenes and arylsilylenes, such as methylsilylene, dimethylsilylene, diethylsilylene, di(n-propyl)silylene, di(i-propyl)silylene, di(cyclohexyl)silylene, methylphenylsilylene, diphenylsilylene, di(p-tolyl)silylene and di(p-chlorophenyl)silylene; alkyldisilylenes, aralkyldisilylenes and aryldisilylenes, such as tetrametyl-1,2-disilylene, tetraphenyl-1,2-disilylene and so on;

germanium-containing divalent groups, in which the silicium in the above silicium-containing divalent groups is replaced by germanium; and tin-containing divalent groups, in which the silicium in the above silicium-containing divalent groups is replaced by tin.

In the above-recited formulae for the divalent groups, $R^7$ stands for a halogen atom, a hydrocarbyl having 1–20 carbon atoms and a halogenated hydrocarbyl having 1–20 carbon atoms.

Among the above-exemplified groups for Y, the silicium-containing divalent groups, the germanium-containing divalent groups and tin-containing divalent groups are preferred, wherein preference is given to the silicium-containing divalent groups, with special preference being given to alkylsilylenes, aralkylsilylenes and arylsilylenes.

In the formula (16), as the ligands coordinating to the metal M, which contain the monocyclic aromatic ring formed by at least one pair among the pairs of $R^3$ with $R^4$, $R^4$ with $R^5$ and $R^5$ with $R^6$, those which are represented by the following formulae (17) to (19) may be exemplified:

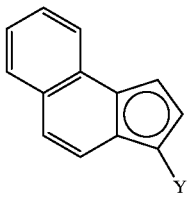

(17)

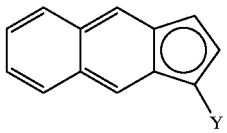

(18)

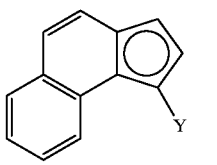

(19)

in which Y has the same meaning as that in the formula (16).

According to the present invention, transition metal compounds represented by the following formula (20) may also be used as the metallocene (g-3),

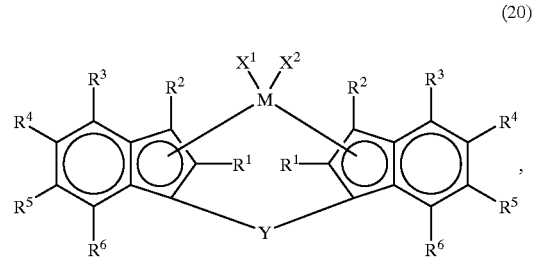

(20)

in which M, $R_1$, $R^2$, $R^3$, $R^4$, $R^5$ and $R^6$ are the same as those in the formula (16).

In the formula (20), it is preferable that, among $R^3$, $R^4$, $R^5$ and $R^6$, two groups including $R^3$ are each an alkyl group, wherein preference is given to that $R^3$ and $R^5$ or $R^3$ and $R^6$ stand each for an alkyl group. These alkyl groups may preferably be secondary or tertiary alkyl groups. Further, these alkyl groups may be substituted by halogen atom(s) or silicium-containing group(s), wherein, as the halogen atom and as the silicium-containing group, those which are exemplified previously for $R^1$ and $R^2$ may be enumerated.

It is preferable, that the groups for $R^3$, $R^4$, $R^5$ and $R^6$ in the formula (20) other than the alkyl groups as mentioned above are hydrogen atom. As the hydrocarbon group having 1–20 carbon atoms, a chainformed alkyl group or a cyclic alkyl group, such as, methyl, ethyl, n-propyl, i-propyl, n-butyl, i-butyl, sec-butyl, tert-butyl, pentyl, hexyl, cyclohexyl, heptyl, octyl, nonyl, dodecyl, eicosyl, norbornyl or adamantyl; or an aralkyl group, such as, benzyl, phenylethyl, phenylpropyl or tolylmethyl, wherein they may include double bond(s) and/or triple bond(s).

It is permissible that two groups selected among $R^3$, $R^4$, $R^5$ and $R^6$ in the formula (20) may form a monocyclic or polycyclic ring other than aromatic ring, by combining together.

As the halogen atom, those enumerated for $R^1$ and $R^2$ are enumerated.

As the groups for $X^1$, $X^2$ and Y, the same ones as in the case of the formula (16) are enumerated.

Concrete examples of the metallocenes (g-3) represented by the formula (20) are given below.

rac-dimethylsilylene-bis(4,7-dimethyl-1-indenyl) zirconium dichloride
  rac-dimethylsilylene-bis(2,4,7-trimethyl-1-indenyl) zirconium dichloride
  rac-dimethylsilylene-bis(2,4,6-trimethyl-1-indenyl) zirconium dichloride According to the present invention, it is also possible to employ transition metal compounds in which the zirconium in the compounds given above is replaced by titanium or hafnium.

The transition metal compounds as given above may usually be employed as a racemate, while it is possible to use R- or S-compound.

For the metallocenes (g-3) represented by the formula (20), such compounds as given below may also be employed.

$R^1$ may preferably be a hydrocarbon group, wherein a particular preferance is given to an alkyl group having 1–4 carbon atoms, such as, methyl, ethyl, propyl or butyl.

$X^1$ and $X^2$ may each preferably be a halogen atom or a hydrocarbon group having 1–20 carbon atoms.

$R^3$ denotes an aryl group having 6–16 carbon atoms, wherein concrete examples therefor include phenyl, α-naphthyl, β-naphthyl, anthracenyl, phenanthryl, pyrenyl, acenaphthyl, phenalenyl (perinaphthenyl) and aceanthrylenyl. Among them, phenyl and naphthyl are preferred. These aryl groups may be substituted by halogen atom(s), hydrocarbon group(s) having 1–20 carbon atoms or halogenated hydrocarbon group(s) having 1–20 carbon atoms, as those defined for $R^1$.

Concrete examples of the transition metal compounds (metallocenes) are given below:

rac-dimethylsilylene-bis(4-phenyl-1-indenyl)-zirconium dichloride
  rac-dimethylsilylene-bis(2-methyl-4-phenyl-1-indenyl)-zirconium dichloride
  rac-dimethylsilylene-bis{2-methyl-4-(α-naphthyl)-1-indenyl}zirconium dichloride
  rac-dimethylsilylene-bis{2-methyl-4-(β-naphthyl)-1-indenyl}zirconium dichloride
  rac-dimethylsilylene-bis{2-methyl-4-(1-anthracenyl)-1-indenyl}zirconium dichloride It is also possible to use transition metal compounds in which the zirconium in the compounds given above is replaced by titanium or hafnium.

According to the present invention, the compounds represented by the following formula (21) may also be used as the metallocenes (g-3):

$$L^a MX_2 \tag{21}$$

In which M is a metal of Group 4 or of the Lantanide series in the periodic table, $L^a$ denotes a derivative from a non-localized π-bound group which imparts a restrictive geometrical configuration to the active sites of the metal M and X denotes, independently of one another, hydrogen atom, a halogen atom, a hydrocarbon group having 20 or less carbon atoms, a silyl group having 20 or less silicium atoms or a germyl group having 20 or less germanium atoms.

Among the compounds represented by the formula (21), those which are represented by the following general formula (22) are preferred:

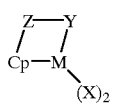

(22)

in which M denotes titanium, zirconium or hafnium, X has the same meaning as that defined for the formula (21), Cp represents a substituted cyclopentadienyl group bound to the metal M by π-bond and having a substituent group Z, Z stands for oxygen, sulfur, boron or an element in Group 14 of the periodic table (for example, silicium, germanium or tin), Y denotes a ligand containing nitrogen, phosphorus, oxygen or sulfur, wherein Z and Y together may form a condensed ring.

For the compounds represented by the formula (22), there may be exemplified {dimethyl(t-butylamido)-(tetramethyl-$\eta^5$-cyclopentadienyl)silane}titanium dichloride and {(t-butylamido)(tetramethyl-$\eta^5$-cyclopentadienyl)-1,2-ethanediyl}titanium dichloride.

Those compounds in which the titanium in the metallocenes given above is replaced by zirconium or hafnium may also be employed.

As the metallocenes (g-3) represented by the formula (21) or (22), zirconocenes in which the central metal atom is zirconium and at least two ligands having cyclopentadienyl skeleton are included may preferably be employed.

As the metallocene (g-3), a transition metal compound of a metal of Group 4 of the periodic table represented by the following formula (23) may also be employed:

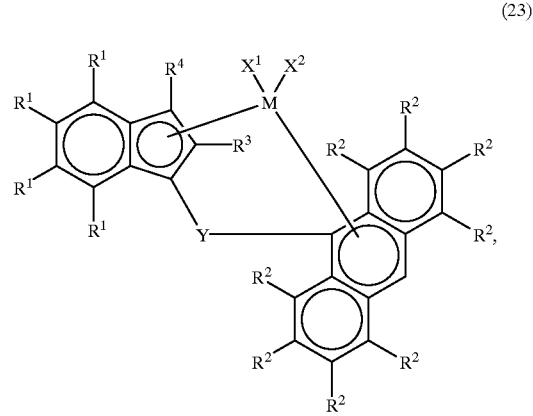

(23)

in which M is a transition metal of Group 4 of the periodic table and may concretely be titanium, zirconium or hafnium, with preference to zirconium.

$R^1$s in the formula (23) may be or may not be identical with each other, wherein at least one of them may be an aryl group having 11–20 carbon atoms, an aralkyl group having 12–40 carbon atoms, an aralkenyl group having 13–40 carbon atoms, an alkaryl group having 12–40 carbon atoms or a silicium-containing group or at least two adjacent $R^1$s among these R¹s may form a monocyclic or polycyclic aromatic or aliphatic ring together with the carbon atom to which they are bound. Here, the total number of carbon atoms of the so-formed ring inclusive of the carbon atoms to which R¹s are bound are 4–20.

Examples in which at least two adjacent R¹s in the formula (23) build up, together with the carbon atoms to which such R¹s are bound, one or more aromatic or aliphatic rings include condensed phenyl group, condensed cyclohexyl group, condensed cyclopentadienyl group, condensed dihydrocyclopentadienyl group, condensed indenyl group, condensed tetrahydroindenyl group, condensed fluorenyl group, condensed tetrahydrofluorenyl group and condensed octahydrofluorenyl group. These groups may be substituted by linear alkyl, cycloalkyl, halogen, halogen-substituted alkyl aryl, silicium-containing group, oxygen-containing group, nitrogen-containing group and/or phosphorus-containing group.

The R¹s other than those which form an aryl, aralkyl, aralkenyl, alkaryl or aromatic or aliphatic ring may stand for hydrogen atom, a halogen atom, an alkyl having 1–10 carbon atoms or a silicium-containing group.

As the aryl group having 11–20 carbon atoms, there may be exemplified biphenyl, anthryl and phenanthryl. As the aralkyl group having 12–40 carbon atoms, there may be exemplified phenanthrylmethyl, phenanthrylethyl and phenanthrylpropyl. As the aralkenyl group having 13–40 carbon atoms, there may be exemplified vinylphenanthryl and so on. As the alkaryl group having 12–40 carbon atoms, there may be exemplified methylphenanthryl, ethylphenanthryl and propylphenanthryl. As the halogen atom, fluorine, chlorine, bromine and iodine are exemplified. As the alkyl group having 1–10 carbon atoms, there may be exemplified methyl, ethyl, propyl, butyl, hexyl, cyclohexyl, octyl and nonyl. As the silicium-containing group, there may be exemplified methylsilyl, phenylsilyl, dimethylsilyl, diethylsilyl, diphenylsilyl, trimethylsilyl, triethylsilyl, tripropylsilyl, tricyclohexylsilyl, triphenylsilyl, dimethylphenylsilyl, methyldiphenylsilyl, tritolylsilyl and trinaphthylsilyl.

These alkyl, aryl, aralkyl, aralkenyl and alkaryl may be halogen-substituted.

In the formula (23), R²s may or may not be identical with each other and may stand each for hydrogen atom, a halogen atom, an alkyl group having 1–10 carbon atoms, an aryl group having 6–20 carbon atoms, an alkenyl group having 2–10 carbon atoms, an aralkyl group having 7–40 carbon atoms, an aralkenyl group having 8–40 carbon atoms, an alkaryl group having 7–40 carbon atoms, a silicium-containing group, an oxygen-containing group, a sulfur-containing group, a nitrogen-containing group or a phosphorus-containing group. At least two adjacent groups among the groups represented by R² in the formula (23) may form, together with the carbon atoms to which these two R²s are bound, one or more aromatic or aliphatic rings. Here, the total number of carbon atoms of the so-formed ring(s) inclusive of the carbon atoms to which these R²s are bound may be 4–20 and the R²s other than those which form the aromatic or aliphatic ring may each stand for hydrogen atom, a halogen atom, an alkyl group having 1–10 carbon atoms or a silicium-containing group.

To the group which is constituted from two R²s in the formula (23) by being formed into one or more aromatic or aliphatic rings, such a group formed from fluorenyl as represented by the following formula (24) may also belong.

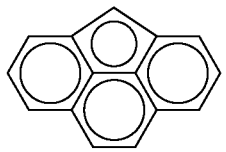

(24)

As the alkyl group having 1–10 carbon atoms and as the halogen atom, the same ones as given above may be exemplified.

As the aryl group having 6–20 carbon atoms, there may be exemplified phenyl, biphenyl, α- and β-naphthyls, anthryl and phenanthryl. As the aralkyl group having 7–40 carbon atoms, there may be exemplified benzyl, phenylethyl, phenylpropyl, phenanthrylmethyl, phenanthrylethyl and phenanthrylpropyl. As the aralkenyl group having 8–40 carbon atoms, there may be exemplified styryl and vinylphenanthryl.

As the alkaryl group having 7–40 carbon atoms, there may be exemplified tolyl, dimethylphenyl, trimethylphenyl, ethylphenyl, propylphenyl, methylnaphthyl, methylphenanthryl, ethylphenanthryl and propylphenanthryl. As the alkenyl group having 2–10 carbon atoms, there may be exemplified vinyl, propenyl and cyclohexenyl. As the silicium-containing group, there may be exemplified the same ones as given previously. As the oxygen-containing group, there may be exemplified hydroxyl, alkoxy groups, such as methoxy, ethoxy, propoxy and butoxy; aryloxy groups, such as phenoxy, methylphenoxy, dimethylphenoxy and naphthoxy; and aralkoxy groups, such as phenylmethoxy and phenylethoxy.

As the sulfur-containing group, there may be exemplified those in which the oxygen atom in the above-mentioned oxygen-containing group is replaced by sulfur atom as well as sulfonates, such as methylsulfonate, trifluoromethanesulfonate, phenylsulfonate, benzylsulfonate, p-toluenesulfonate, trimethylbenzenesulfonate, triisobutylbenzenesulfonate, p-chlorobenzenesulfonate and pentafluorobenzenesulfonate; and sulfinates, such as methylsulfinate, phenylsulfinate, benzenesulfinate, p-toluenesulfinate, trimethylbenzenesulfinate and pentafluorobenzenesulfinate.

As the nitrogen-containing group, there may be exemplified, amino; alkylamino groups, such as methylamino, dimethylamino, diethylamino, dipropylamino, dibutylamino and dicyclohexylamino; arylamino groups, such as phenylamino, diphenylamino, ditolylamino, dinaphthylamino and methylphenylamino; and alkarylamino groups.

As the phosphorus-containing group, there may be exemplified dimethylphosphino and diphenylphosphino.

The groups R² may preferably be hydrogen atom or an alkyl group, wherein special preferance is given to hydrogen atom or a hydrocarbyl having 1 to 3 carbon atoms, such as methyl, ethyl or propyl.

As the fluorenyl group having such substituent groups R², there may be enumerated, as a favorable example, 2,7-dialkylfluorenyl with preferable alkyl groups having 1–5 carbon atoms.

The above-mentioned R¹ and R² may or may not be identical with each other.

R³ and R⁴ in the formula (23) may be identical with or different from each other, wherein they may each stand, similarly as above, for hydrogen atom, a halogen atom, an alkyl group having 1–10 carbon atoms, an aryl group having 6–20 carbon atoms, an alkenyl group having 2–10 carbon atoms, an aralkyl group having 7–40 carbon atoms, an aralkenyl group having 8–40 carbon atoms, an alkaryl group having 7–40 carbon atoms, a silicium-containing group, an oxygen-containing group, a sulfur-containing group, a nitrogen-containing group or a phosphorus-containing group.

Among them, $R^3$ and $R^4$ may favorably be such that at least one of them is an alkyl group having 1–3 carbon atoms.

$X^1$ and $X^2$ in the formula (23) may be identical with or different from each other and may each be hydrogen atom, a halogen atom, a hydrocarbyl having 1–20 carbon atoms, a halogenated hydrocarbyl having 1–20 carbon atoms, an oxygen-containing group, a sulfur-containing group or a nitrogen-containing group, or they may form together a conjugate diene radical, wherein concrete examples of halogen atom, oxygen-containing group, sulfur-containing group and nitrogen-containing group include those which are exemplified as above.

As the hydrocarbyl having 1–20 carbon atoms, there may be exemplified an alkyl group, such as methyl, ethyl, propyl, butyl, hexyl, cyclohexyl, octyl, nonyl, dodecyl, eicosyl, norbornyl or adamantyl; an alkenyl group, such as, vinyl, propenyl or cyclohexenyl; an aralkyl group, such as, benzyl, phenylethyl or phenylpropyl; or an aryl group, such as phenyl, tolyl, dimethylphenyl, trimethylphenyl, ethylphenyl, propylphenyl, α- or β-naphthyl, methylnaphthyl, anthryl, phenanthryl, benzylphenyl, pyrenylacenaphthyl, phenalenyl, aceanthrenyl, tetrahydronaphthyl, indanyl and biphenylyl. As the halogenated hydrocarbyl having 1–20 carbon atoms, there may be exemplified those in which the above-mentioned hydrocarbyls having 1–20 carbonatoms have halogen substituent(s).

As the conjugated diene radial formed from $X^1$ and $X^2$, there may be exemplified $\eta^4$-1,4-diphenyl-1,3-butadiene, $\eta^4$-1,3-butadiene, $\eta^4$-1,4-dibenzyl-1,3-butadiene, $\eta^4$-1-phenyl-1,3-pentadiene, $\eta^4$-3-methyl-1,3-pentadiene, $\eta^4$-1,4-bis(trimethylsilyl)-1,3-butadiene 2,3-dimethylbutadiene, $\eta^4$-2,4-hexadiene and isoprene. As the conjugated diene radical formed from $X^1$ and $X^2$, preference is given to those of 1,3-butadiene, 2,4-hexadiene, 1-phenyl-1,3-pentadiene and 1,4-diphenylbutadiene, wherein these radicals may further be substituted by a hydrocarbyl having 1–10 carbon atoms.

Among them, preference is given to those in which $X^1$ and $X^2$ are each a halogen atom, a hydrocarbyl having 1–20 carbon atoms or a sulfur-containing group.

In the formula (23), Y denotes a divalent hydrocarbon group having 1–20 carbon atoms, a divalent halogenated hydrocarbon group having 1–20 carbon atoms, a divalent silicium-containing group, a divalent germanium-containing group, a divalent tin-containing group, the group —O—, —CO—, —S—, —SO—, —SO$_2$—, —NR$^5$—, —P(R$^5$)—, —P(O)(R$^5$)—, —BR$^5$— or —AlR$^5$—, with $R^5$ being hydrogen atom, a halogen atom, a hydrocarbyl having 1–20 carbon atoms, a halogenated hydrocarbyl having 1–20 carbon atoms.

Concrete examples of Y in the formula (23) include
divalent hydrocarbon groups having 1–20 carbon atoms, for example, alkylenes, such as methylene, dimethylmethylene, 1,2-ethylene, dimethyl-1,2-ethylene, 1,3-trimethylene, 1,4-tetramethylene, 1,2-cyclohexylene and 1,4-cyclohexylene; and aralkylenes, such as diphenylmethylene and diphenyl-1,2-ethylene;
halogenated hydrocarbon groups derived from divalent hydrocarbon groups having 1–20 carbon atoms which are halogenated, such as chloromethylene;

silicium-containing divalent groups, for example, alkylsilylenes, alkarylsilylenes and arylsilylenes, such as methylsilylene, dimethylsilylene, diethylsilylene, di(n-propyl)silylene, di(i-propyl)silylene, di(cyclohexyl)silylene, methylphenylsilylene, diphenylsilylene, di(p-tolyl)silylene and di(p-chlorophenyl)silylene;
alkyldisilylenes, alkaryldisilylenes and aryldisilylenes, such as tetrametyl-1,2-disilylene, tetraphenyl-1,2-disilylene and so on;
germanium-containing divalent groups, in which the silicium in the above silicium-containing divalent groups is replaced by germanium; and
tin-containing divalent groups, in which the silicium in the above silicium-containing divalent groups is replaced by tin.

Among them, those in which the shortest bond of —Y— bridge as shown by the formula (23) is constituted of one or two atoms are preferreed.

In the above-recited formulae for the divalent groups, $R^5$ stands, the same as the above, for a halogen atom, a hydrocarbyl having 1–20 carbon atoms and a halogenated hydrocarbyl having 1–20 carbon atoms.

Among the above-exemplified groups for Y, the divalent $C_1$–$C_5$ hydrocarbyl groups, the silicium-containing divalent groups, the germanium-containing divalent groups are preferred, wherein preference is given to the siliciumcontaining divalent groups, with special preference to alkylsilylenes, aralkylsilylenes and arylsilylenes.

As the metallocene (g-3), a transition metal compound represented by the following formula (25) may also be used.

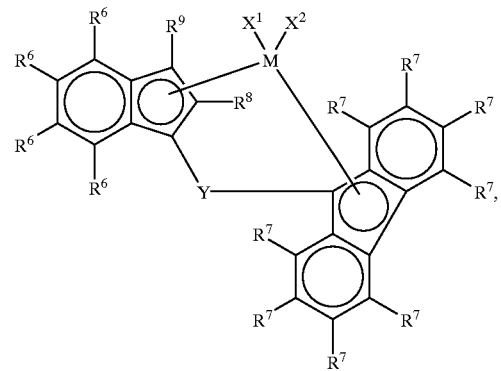

(25)

in which M denotes a transition metal element of Group 4 of the periodic table and may concretely stand for titanium, zirconium or hafnium, preferably zirconium.

$R^6$s in the formula (25) may be identical with or different from each other and may stand for hydrogen atom, a halogen atom, an alkyl having 1–10 carbon atom, an aryl having 6–10 carbon atom, an alkenyl having 2–10 carbon atoms, a silicium-containing group, an oxygen-containing group, sulfur-containing group, nitrogen-containing group or a phosphorus-containing group, wherein they may concretely stand, when they are a halogen atom or an alkyl of $C_1$ to $C_{10}$, for those which are given for $R^1$ of the formula (23) and, as the silicium-containing group, oxygen-containing group, sulfur-containing group, nitrogen-containing group and phosphorus-containing group, there may be exemplified the same ones as those given for $R^2$ of the formula (23).

As the aryl having 6–10 carbon atoms, there may be exemplified phenyl and α- and β-naphthyl. As the alkenyl having 2–10 carbon atoms, there may be exemplified vinyl, propenyl and cyclohexenyl. These alkyls and alkenyls may be substituted by halogen.

Among them, $R^6$ may preferably be an alkyl, aryl or hydrogen atom, wherein particular preference is given to hydrocarbon groups having 1–3 carbon atoms, such as methyl, ethyl, n-propyl and i-propyl, and such aryl groups as phenyl, α-naphthyl and β-naphthyl, as well as hydrogen atom.

$R^7$s in the formula (25) may be identical with or different from each other and may each be hydrogen atom, a halogen atom, an alkyl having 1–10 carbon atoms, an aryl having 6–20 carbon atoms, an alkenyl having 2–10 carbon atoms, an aralkyl having 7–40 carbon atoms, an arylalkenyl group having 8–40 carbon atoms, an alkaryl group having 7–40 carbon atoms, a silicium-containing group, an oxygen-containing group, a sulfur-containing group, a nitrogen-containing group or a phosphorus-containing group. Concretely, they may be those which are given for $R^2$ in the formula (23).

These alkyls, aryls, alkenyls, aralkyls, aralkenyls and alkaryls may be substituted by halogen.

Among them, $R^7$s may each preferably be hydrogen atom or an alkyl, wherein special preference is given to hydrogen atom and hydrocarbyls having 1–4 carbon atoms, such as methyl, ethyl, n-propyl, i-propyl, n-butyl and tert-butyl.

$R^6$ and $R^7$ may be identical with or different from each other.

Either one of $R^8$ and $R^9$ in the formula (25) is an alkyl having 1–5 carbon atoms and the other is hydrogen atom, a halogen atom, an alkyl having 1–10 carbon atoms, an alkenyl having 2–10 carbon atoms, a silicium-containing group, an oxygen-containing group, a sulfur-containing group a nitrogen-containing group or a phosphorus-containing group, as those given for $R^2$ in the formula (23).

As the alkyl having 1–5 carbon atoms, there may be exemplified methyl, ethyl, propyl, butyl and pentyl.

Among them, preference is given to those in which either one of $R^8$ and $R^9$ is an alkyl having 1–3 carbon atoms, such as methyl, ethyl or propyl, and the other is hydrogen atom.

$X^1$ and $X^2$ in the formula (25) may be identical with or different from each other and each may be hydrogen atom, a halogen atom, a hydrocarbyl having 1–20 carbon atoms, a halogenated hydrocarbyl having 1–20 carbon atoms, an oxygen-containing group, a sulfur-containing group or a nitrogen-containing group, as in the $X^1$ and $X^2$ in the formula (23), or they may build up together a conjugated diene radical.

Among them, halogen atoms and hydrocarbyls having 1–20 carbon atoms are preferred.

In the formula (25), Y denotes, as in the formula (23), a divalent hydrocarbon group having 1–20 carbon atoms, a divalent halogenated hydrocarbon group having 1–20 carbon atoms, a divalent silicium-containing group, a divalent germanium-containing group, a divalent tin-containing group, the group —O—, —CO—, —S—, —SO—, —SO$_2$—, —NR$^5$—, —P(R$^5$)—, —P(O)(R$^5$)—, —BR$^5$— or —AlR$^5$—, with R$^5$ being hydrogen atom, a halogen atom, a hydrocarbyl having 1–20 carbon atoms or a halogenated hydrocarbyl having 1–20 carbon atoms.

Among them, Y may preferably be a divalent hydrocarbyl having 1–5 carbon atoms, a silicium-containing divalent group or a germanium-containing divalent group, with special preference to silicium-containing divalent group, concrete examples of which are alkylsilylenes, alkylarylsilylenes and arylsilylenes.

The metallocenes (g-3) may be employed alone or in combination of two or more of them. It is possible to use the metallocenes (g-3) under dilution in a solvent such as a hydrocarbon or a halogenated hydrocarbon. It is also possible to use the metallocene (g-3) in a state held in contact with a granular carrier compound.

For the carrier compound supporting the metallocene (g-3), inorganic compounds, such as, $SiO_2$, $Al_2O_3$, $B_2O_3$, MgO, $ZrO_2$, CaO, $TiO_2$, ZnO, $SnO_2$, BaO and ThO, and resins of, for example, polyethylene, polypropylene, poly-1-butene, poly-4-methyl-1-pentene and styrene/divinylbenzene copolymer, may be employed. These carrier compounds may be used alone or in combination of two or more of them.

Now, the description is directed to the organoaluminum oxy-compound (h-2) and the ionizing ionic compound (j-1) to be used for preparing the catalyst based on metallocene.

The organoaluminum oxy-compound (h-2) to be employed according to the present invention may be aluminoxanes known per se or may be those which are insoluble in benzene.

The known aluminoxanes mentioned above may concretely be represented by the following formula (26) or (27):

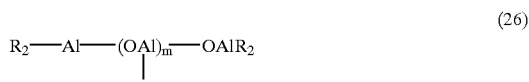

(26)

(27)

in which R represents a hydrocarbon group, such as, methyl, ethyl, propyl or butyl, preferably methyl or ethyl, with a particular preference to methyl, m is an integer of 2 or higher, preferably 5–40.

In the formula (26) or (27), the aluminoxane may be composed of mixed alkyloxyaluminum units constituted of an alkyloxyaluminum unit represented by the formula OAl ($R^1$) and an alkyloxyaluminum unit represented by the formula OAl($R^1$), wherein $R^1$ and $R^2$ may each stand for those defined for R and $R^1$ is different from $R^2$.

The organoaluminum oxy-compound (h-2) employed according to the present invention may contain a small amount of other organometallic component(s) than organoaluminum.

As the ionizing ionic compound (j-1), which may sometimes be called "ionic ionizing compound" or simply "ionic compound", there may be exemplified Lewis acids, ionic compounds, boranes and carboranes.

As the Lewis acids, those which are represented by $BR_3$, wherein R stands for fluorine or a phenyl group which may have substituent group(s), such as, fluorine, methyl or trifluoromethyl, may be employed. Concrete examples of such a Lewis acid include trifluoroboron, triphenylboron, tris(4-fluorophenyl)boron, tris(3,5-difluorophenyl)boron, tris(4-fluoromethylphenyl)boron, tris(pentafluorophenyl) boron, tris(p-tolyl)boron, tris(o-tolyl)boron and tris(3,5-dimethylphenyl)boron.

As the ionic compounds memtioned above, there may be enumerated for example, trialkyl-substituted ammonium salts, N,N-dialkylanilinium salts, dialkylammonium salts and triarylphosphonium salts. As the trialkyl-substituted ammonium salt for the ionic compound, there may be exemplified triethylammonium tetra(phenyl)boron, tripropylammonium tetra(phenyl)boron and tri(n-butyl) ammonium tetra(phenyl)boron. As the dialkylammonium salt for the ionic compound, there may be exemplified di(1-propyl)ammonium tetra(pentafluorophenyl)boron and dicyclohexylammonium tetra(phenyl)boron.

As the ionic compounds mentioned above, there may be exemplified triphenylcarbenium tetrakis(pentafluorophenyl) borate, N,N-dimethylanilinium tetrakis(pentafluorophenyl) borate and ferrocenium tetra(pentafluorophenyl) borate.

As the boranes mentioned above, there may be exemplified salts of metal borane anions, such as, decaborane(9); bis[tri(n-butyl)ammonium] nonaborate, bis[tri(n-butyl) ammonium] decaborate and bis[tri(n-butyl)ammonium] bis (dodecahydride-dodecaborate) nickelate(III).

As the carboranes mentioned above, there may be exemplified salts of metal carborane anions, such as, 4-carbanonaborane(9), 1,3-dicarbanonaborane(8), bis[tri(n-butyl)ammonium] bis(undecahydride-7-carbaundecaborate] nickelate(IV).

The ionizing ionic compound (j-1) may be used alone or in combination of two or more of them. The organoaluminum oxy-compound (h-2) and the ionizing ionic compound (j-1) may be used in a form held on the carrier compound mentioned previously.

On preparing the catalyst based on metallocene, the organoaluminum compounds (h-1) described above can be used together with the organoaluminum oxy-compound (h-2) or the ionizing ionic compound (j-1).

For producing the second copolymer (I-2) according to the present invention, i.e. the ethylene/α-olefin/triene random copolymer, ethylene (A-1), the α-olefin (A-2), the linear triene compound (B-2) and, if necessary, another copolymerizable comonomer(s) are co-polymerized, usually in a liquid phase, in the presence of the catalyst based on titanium, based on vanadium or based on metallocene as described above. Here, a hydrocarbon solvent is used usually, while it is permissible to use the α-olefin as the solvent.

The copolymerization of ethylene (A-1), the α-olefin (A-2) and the linear triene compound (B-2) may be effected either in a batch-wise or continuous way. On carrying out the copolymerization in a batch-wise way, the catalyst may be used at a concentration as given below:

For the catalyst based on titanium composed of the solid titaniferous component (g-1) and the organoaluminum compound (h-1), the solid titaniferous component (g-1) may be used usually in an amount of, as calculated based on titanium atom, about 0.001 to about 1.0 mmol, preferably about 0.005 to 0.5 mmol, per liter of the copolymerization volume. The organoaluminum compound (h-1) may be used usually in an amount of, as calculated based on the metal atom in the organoaluminum compound (h-1), about 10–500 moles, preferably 20–200 moles, per mole of the titanium in the solid titaniferous component (g-1). In case an electron donor is used, it may be used usually in an amount of about 0.001 to 10 moles, preferably 0.01 to 2 moles, especially preferably 0.05 to 1 mole, per mole of the metal atom in the organoaluminum compound (h-1).

In case the catalyst based on vanadium composed of the soluble vanadium compound (g-2) and the organoaluminum compound (h-1) is employed, the concentration of the soluble vanadium compound (g-2) within the copolymerization system may usually be in the range from 0.01 to 5 mmol, preferably from 0.05 to 3 mmol, per liter of the polymerization volume. The soluble vanadium compound (g-2) may preferably be supplied to the copolymerization system at a concentration of 10 times or less, preferably 1–7 times, more preferably 1–5 times the existing concentration of the soluble vanadium compound in the copolymerization system. The organoaluminum compound (h-1) may be supplied to the copolymerization system in a mole ratio of aluminum to vanadium (Al/V) in the copolymerization system of 2 or higher, preferably in the range of 2–50, more preferably in the range of 3–20.

The soluble vanadium compound (g-2) and the organoaluminum compound (h-1) may be supplied to the copolymerization system usually under dilution in the hydrocarbon solvent and/or a liquid mixture of ethylene and the linear triene compound (B-2). Here, it is favorable to supply the organoaluminum compound (h-1) to the copolymerization system at a concentration adjusted to any voluntary concentration below, for example, 50 times the existing concentration thereof in the copolymerization system, while the soluble vanadium compound (g-2) is supplied thereto preferably under dilution at a concentration as given previously.

In using the catalyst based on metallocene composed of the metallocene (g-3) and the organoaluminum oxy-compound (h-2) or the ionizing ionic compound (j-1), the concentration of the metallocene (g-3) in the copolymerization system may usually be in the range of 0.00005–0.1 mmol, preferably in the range of 0.0001–0.05 mmol, per liter of the polymerization volume. The organoaluminum oxy-compound (h-2) may be supplied to the copolymerization system in a mole ratio of aluminum to the transition metal in the metallocene (Al/transition metal) of 1–10,000, preferably 10–5,000.

For the ionizing ionic compound (j-1), it is supplied to the copolymerization system in a mole ratio of the ionizing ionic compound to the metallocene (g-3) {ionic compound (j-1)/ metallocene (g-3)} in the range of 0.5–20, preferably 1–10.

In case of incorporation of the organoaluminum compound (h-1), it is used usually in such an amount that its concentration will be at about 0–5 mmol per liter of the polymerization volume, preferably about 0–2 mmol per liter of the polymerization volume.

The copolymerization of the comonomers, i.e. ethylene (A-1), the α-olefin (A-2) and the linear triene compound (B-2) represented by the formula (2) in the presence of the catalyst based on titanium mentioned above according to the present invention may be realized usually under the condition of a temperature in the range from –20° C. to +150° C., preferably from 0 to 120° C., more preferably from 0 to 100° C., and a pressure in the range over 0 up to 7.8 MPa (80 kgf/cm$^2$ gauge), preferably over 0 up to 4.9 MPa (50 kgf/cm$^2$ gauge).

For copolymerizing the comonomers, i.e. ethylene (A-1), the α-olefin (A-2) and the linear triene compound (B-2) represented by the formula (2), in the presence of the catalyst based on vanadium mentioned above according to the present invention, the copolymerization may be effected under the condition of a temperature in the range from –50° C. to +100° C. preferably from –30° C. to +80° C., more preferably from –20° C. to +60° C., and a pressure in the range over 0 up to 4.9 MPa (50 kgf/cm$^2$ gauge), preferably over 0 up to 2.0 MPa (20 kgf/cm$^2$ gauge).

For copolymerizing the comonomers, i.e. ethylene (A-1), the α-olefin (A-2) and the linear triene compound (B-2) represented by the formula (2), in the presence of the catalyst based on metallocene mentioned above according to the present invention, the copolymerization may be effected under the condition of a temperature in the range from –20° C. to +150° C. preferably from 0 to 120° C., more preferably from 0 to 100° C., and a pressure in the range over 0 up to 7.8 MPa (80 kgf/cm$^2$ guage), preferably in the range over 0 up to 4.9 MPa (50 kgf/cm$^2$ gauge).

According to the present invention, ethylene (A-1), the α-olefin (A-2), the linear triene compound (B-2) represented by the formula (2) and other comonomer(s) to be added optionally may be supplied to the copolymerization system each in such an amount that the second copolymer (I-2) having the above-mentioned definite compostion will be obtained. On the copolymerization, a molecular weight regulator, such as hydrogen, can be employed.

By copolymerizing ethylene (A-1), the α-olefin (A-2), and the linear triene compound (B-2) represented by the formula (2), the second copolymer (I-2), i.e. the ethylene/α-olefin/triene random copolymer, is obtained usually as a liquid polymerization mixture containing the copolymer. This liquid copolymerization product is subjected to an after-treatment in a usual way to obtain the second copolymer (I-2), i.e. the ethylene/α-olefin/triene random copolymer.

The second copolymer (I-2) according to the present invention, i.e. the ethylene/α-olefin/triene random copolymer, obtained in this way is capable of being vulcanized at higher velocity and superior in the scorch stability together with superiorities in the weatherability, heat resistance and fastness to ozone, so that it can be utilized for applications, such as the starting material for various rubber products and as modifier for resins. Vulcanized rubber products obtained by vulcanization of the second copolymer (I-2) according to the present invention, i.e. the ethylene/α-olefin/triene random copolymer, are superior not only in the weatherability, heat resistance and fastness to ozone but also in the rubbery elasticity. On producing vulcanized rubber products using the second copolymer (I-2) according to the present invention, i.e. the ethylene/α-olefin/triene random copolymer, it can be subjected to a high velocity vulcanization and, therefore, a high productivity can be attained.

The second composition according to the present invention comprises the second copolymer (I-2) according to the present invention, i.e. the ethylene/α-olefin/triene random copolymer, a vulcanizing agent (II) and/or a filler (III). The second composition according to the present invention consists of a vulcanizable rubber composition, which can be brought into practical use in the unvulcanized state as such, though it can develop more advantageous features when used in a vulcanized form. Vulcanization can be realized in various ways, for example, by heating under employment of a vulcanizing agent (II) or by irradiation of electron beam without using any vulcanizing agent (II). As the filler (III), there may be exemplified reinforcing agents and softening agents.

The vulcanized rubber products obtained by vulcanization of the second composition according to the present invention are superior not only in the weatherability, heat resistance, fastness to ozone and fastness to dynamic fatigue but also in the rubbery elasticity and low temperature flexibility. On producing vulcanized rubber products using the second composition according to the present invention, a high productivity can be attained, since the second copolymer (I-2) according to the present invention, i.e. the ethylene/α-olefin/triene random copolymer, can be vulcanized at high velocity. It is also possible to reduce the amount of the vulcanizing agent (II) and that of vulcanization accelerator to be incorporated, so that vulcanized rubber product exhibiting superior appearance with lower degree of blooming can be obtained.

For vulcanizing the second composition according to the present invention by heating, compounds constituting the vulcanizing system, such as, vulcanizing agent (II), vulcanization accelerator and vulcanization assistant, can be admixed to the second composition.

In the second composition according to the present invention, there may be incorporated as the vulcanizing agent (II) sulfur, compounds based on sulfur and organic peroxides.

The form of sulfur is not specifically limited and, for example, powdery sulfur, precipitated sulfur, colloidal sulfur, surface-treated sulfur and insoluble sulfur may be employed.

As the compound based on sulfur mentioned above, there may be exemplified concretely sulfur chloride, sulfur dichloride, high-polymeric polysulfides, morpholine disulfide, alkylphenol disulfide, tetramethylthiuram disulfide and selenium dimethyldithiocarbamate.

As the organic peroxide mentioned above, there may be exemplified concretely alkyl peroxides, such as, dicumyl peroxide, di-t-butyl peroxide, di-t-butyl peroxy-3,3,5-trimethylcyclohexane, t-butylcumyl peroxide, di-t-amyl peroxide, 2,5-dimethyl-2,5-di(t-butylperoxy)hexine-3,2,5-dimethyl-2,5-di(benzoylperoxy)hexane, 2,5-dimethyl-2,5-di(t-butylperoxy)hexane, α, α'-bis(t-butylperoxy-m-isopropyl)benzene and t-butyl hydroperoxide; peroxyesters, such as, t-butylperoxy acetate, t-butylperoxy isobutyrate, t-butylperoxy pivalate, t-butylperoxy maleate, t-butylperoxy neodecanoate, t-butylperoxy benzoate and di-t-butylperoxy phthalate; and ketone peroxides, such as, dicyclohexanone peroxide etc. They can be used in a combination of two or more of them.

Among them, organic peroxides having a 1 minute half life temperature of 130–200° C. are preferred, for example, dicumyl peroxide, di-t-butyl peroxide, di-t-butylperoxy-3,3,5-trimethylcyclohexane, t-butylcumyl peroxide, di-t-amyl peroxide and t-butyl hydroperoxide.

According to the present invention, among the above vulcanizing agents (II), preference is given to sulfur and sulfur compounds, especially to sulfur, since a rubber composition exhibiting superior characteristic can be obtained therewith.

When the vulcanizing agent (II) is sulfur or a sulfur compound, it can be used in an amount of 0.1–10 parts by weight, preferably 0.5–5 parts by weight, per 100 parts by weight of the second copolymer (I-2) according to the present invention, i.e. the ethylene/α-olefin/triene random copolymer.

When the vulcanizing agent (II) is an organic peroxide, it can be used in an amount of 0.05–15 parts by weight, preferably 0.15–5 parts by weight, per 100 parts by weight of the second copolymer (I-2) according to the present invention, i.e. the ethylene/α-olefin/triene random copolymer.

When sulfur or a sulfur compound is used as the vulcanizing agent, it is preferable to use a vulcanization accelerator concurrently.

As the vulcanization accelerator, there may be exemplified concretely compounds based on sulfenamide, such as, N-cyclohexyl-2-benzothiazole sulfenamide (CBS), N-oxydiethylene-2-benzothiazole sulfenamide and N,N-diisopropyl-2-benzothiazole sulfenamide; compounds based on thiazole, such as, 2-mercaptobenzothiazole (MBT), 2-(2,4-dinitrophenyl)mercaptobenzothiazole, 2-(2,6-diethyl-4-morpholinothio)benzothiazole, 2-(4'-morpholinodithio) benzothiazole and dibenzothiazyl disulfide; guanidine compounds, such as, diphenylguanidine, triphenylguanidine, diorthonitrileguanidine, orthonitrile biguanide and diphenylguanidine phthalate; compounds based on aldehydeamine or aldehyde-ammonia, such as, reaction products of acetaldehyde with aniline, condensation products of butyl aldehyde with aniline, hexamethylenetetramine and acetaldehydeammonia; compounds based on imidazoline, such as, 2-mercaptoimidazoline and the like; compounds based on thiourea, such as, thiocarbanilide, diethylthiourea, dibutylthiourea trimethylthiourea and diorthotolylthiourea; compounds based on thiuram, such as, tetramethylthiuram monosulfide, tetramethylthiuram disulfide (TMTD), tetraethylthiuram disulfide, tetrabutylthiuram disulfide, pentamethylenethiuram tetrasulfide and dipentamethylenethiuram tetrasulfide (DPTT); compounds based on dithio acid salts, such as, zinc dimethyldithiocarbamate, zinc diethyldithiocarbamate, zinc di-n-butyldithiocarbamate, zinc ethylphenylthiocarbamate, zinc butylphenyldithiocarbamate, sodium dimethyldithiocarbamate, selenium dimethyldithiocarbamate and tellurium dimethyldithiocarbamate; compounds based on xanthate, such as zinc dibutylxantogenate; and zinc white.

The vulcanization accelerator may preferably be used in an amount of 0.1–20 parts by weight, preferably 0.2–10 parts by weight, per 100 parts by weight of the second copolymer (I-2) according to the present invention, i.e. the ethylene/α-olefin/triene random copolymer.

When using as the vulcanizing agent (II) an organic peroxide, it is preferable to use concurrently a vulcanization assistant in an amount of 0.5–2 moles per mole of the organic peroxide, preferably in a nearly equimolar amount therewith.

As the vulcanization assistant, there may be exemplified concretely sulfur, compounds based on quinone dioxime, such as, p-quinone dioxime etc., in addition to polyfunctional monomers, for example, compounds based on (meth) acrylate, such as, trimethylol propane triacrylate, polyethyleneglycol dimethacrylate etc.; compounds based on allyl, such as diallyl phthalate and triallyl cyanurate; compounds based on maleimide, such as m-phenylene bismaleimide etc.; and divinyl benzene.

As the reinforcing agent to be used as the filler (III) in the second composition according to the present invention, there may be used carbon black products, such as SRF, GPF, FEF, MAF, HAF, ISAF, SAF, FT and MT; surface treated carbon black products in which the above-mentioned carbon black product is subjected to a surface treatment using a silane coupling agent; inorganic fillers, such as, silica, activated calcium carbonate, light calcium carbonate, heavy calcium carbonate, fine powdery talc, talc, fine powdery silicic acid and clays.

The reinforcing agent may be used in an amount of 300 parts by weight or less, preferably 10–300 parts by weight, more preferably 10–200 parts by weight, per 100 parts by weight of the second copolymer (I-2) according to the present invention, i.e. the ethylene/α-olefin/triene random copolymer.

Using the composition containing the reinforcing agent in such an amount, a vulcanized rubber product in which the mechanical properties, such as, tensile strength, tear strength and wear resistance, are improved can be obtained. It is also possible to increase the hardness without deteriorating other material properties of the vulcanized rubber, together with attainment of reduction of the production cost.

As the softening agent to be used as filler (III) in the second composition according to the present invention, conventional softening agent to be compounded to rubber products may widely be utilized. Concrete examples therefor include softening agents based on petroleum oil, such as, processoils, lubricating oils, paraffin, liquid paraffin, petroleum asphalt and vaseline; softening agents based on coal tar, such as, coal tar and coal tar pitch; softening agents based on fatty oils, such as, castor oil, linseed oil, rape-seed oil, palm oil; waxes, such as, tall oil, factice, bees wax, carnauba wax and lanolin; fatty acids and fatty acid salts, such as, ricinoleic acid, palmitic acid, barium stearate, calcium stearate and zinc laurate; plasticizers based on esters, such as dioctyl phthalate, dioctyl adipate and dioctyl sebacate; and synthetic highpolymeric substances, such as, petroleum resin, atactic polypropylene and cumarone-indene resin. Among them, softening agents based on petroleum oil are preferred, with particular preference to process oils.

The softening agent may be used in an amount of 200 parts by weight or less, preferably 10–200 parts by weight, more preferably 10–150 parts by weight, per 100 parts by weight of the second copolymer (I-2) according to the present invention, i.e. the ethylene/α-olefin/triene random copolymer.

The second composition according to the present invention may contain other component(s) than those described above. For example, compounds constituting the foaming system, such as, foaming agent and foaming assistants, antioxydant (stabilizer), processing assistant, plasticizer, coloring agents, other rubber additives and various chemicals may be incorporated. The kinds and amounts of such other components may voluntarily be selected according to each specific application.

The second composition according to the present invention may be molded under foaming, if it contains compounds constituting a foaming system, such as, foaming agent and foaming assistant.

As the foaming agent, those which have found applications generally for foaming rubbers can be used widely. Concrete examples therefor include inorganic foaming agents, such as, sodium bicarbonate, sodium carbonate, ammonium bicarbonate, ammonium carbonate and ammonium nitrite; nitroso compounds, such as, N,N'-dimethyl-N,N'-dinitrosoterephthalamide and N,N'-dinitrosopentamethylenetetramine; azo compounds, such as, azodicarbonamide, azobisisobutyronitrile, azocyclohexylnitrile, azoaminobenzene and barium azodicarboxylate; sulfonylhydrazide compounds, such as, benzenesulfonylhydrazide, toluenesulfonylhydrazide, p,p'-oxybis(benzenesulfonylhydrazide) and diphenylsulfon-3,3'-disulfonylhydrazide; and azide compounds, such as, calcium azide, 4,4-diphenyldisulfonyl azide and p-toluenesulfonyl azide. Among them, nitoso compounds, azo compounds and azide compounds are preferred.

The foaming agent may be used in an amount of 0.5–30 parts by weight, preferably 1–20 parts by weight, per 100 parts by weight of the second copolymer (I-2) according to the present invention, i.e. the ethylene/α-olefin/triene random copolymer. From a composition having a content of the foaming agent in the above-mentioned range, a foamed product having an apparent density of 0.03–0.8 g/cm$^3$ can be produced.

A foaming assistant may also be used together with the foaming agent. By a concurrent use of a foaming assistant may bring about advantageous effects of decreasing the decomposition temperature of the foaming agent, acceleration of decomposition of the foaming agent and homogenization of the foam sizes. As the foaming assistant, for example, organic acids, such as, salicilic acid, phthalic acid, stearic acid and oxalic acid, as well as urea and its derivatives may be enumerated.

The foaming assistant may be used in an amount of 0.01–10 parts by weight, preferably 0.1–5 parts by weight, per 100 parts by weight of the second copolymer (I-2) according to the present invention, i.e. the ethylene/α-olefin/triene random copolymer.

By incorporating an antioxydant in the second composition according to the present invention, the life of the product can favorably be extended. Concrete examples of the antioxydant include stabilizers based on aromatic secondary amine, such as, phenylnaphthylamine, 4,4'-(α,α-dimethylbenzyl)diphenylamine and N,N'-di-2-naphthyl-p-phenylenediamine; stabilizers based on phenol, such as, 2,6-di-t-butyl-4-methylphenole and tetrakis-{methylene-3-(3',5'-di-t-butyl-4'-hydroxyphenyl)propionate}methane; stabilizers based on thioether, such as, bis{2-methyl-4-(3-n-alkylthiopropionyloxy)-5-t-butylphenyl}sulfide and the like; stabilizers based on benzimidazole, such as 2-mercaptobenzimidazole etc.; stabilizers based on dithiocarbamate, such as, nickel dibutyldithiocarbamate etc.; and stabilizers based on quinoline, such as a polymer of 2,2,4-trimethyl-1,2-dihydroquinoline. They can also be used in a combination of two or more of them.

The antioxydant may be used in an amount of 5 parts by weight or less, preferably 3 parts by weight or less, per 100 parts by weight of the second copolymer (I-2) according to the present invention, i.e. the ethylene/α-olefin/triene random copolymer.

For the processing assistant, those which have found applications generally as processing assistant in rubbers can be used widely. Concrete examples include acids, such as, ricinoleic acid, stearic acid, palmitic acid and lauric acid; salts of these higher fatty acids, such as, barium stearate, zinc stearate and calcium stearate; and esters.

The processing assistant may be used in an amount of 10 parts by weight or less, preferably 5 parts by weight or less, per 100 parts by weight of the second copolymer (I-2), i.e. the ethylene/α-olefin/triene random copolymer.

The second composition according to the present invention may contain other rubber component(s) known per se, within the range not obstructing the purpose of the invention.

For such other rubber component(s), there may be enumerated, for example, natural rubber (NR), rubbers based on isoprene, such as isoprene rubber (IR) etc.; rubbers based on conjugated diene, such as, butadiene rubber (BR), styrene-butadiene rubber (SBR), acrilonitrile-butadiene rubber (NBR) and chloroprene rubber (CR); and hydrogenated NBR.

It is also possible to incorporate other known copolymer rubber based on ethylene/α-olefin. For example, an ethylene/propylene random copolymer (EPR) and an ethylene/α-olefin/polyene copolymer, such as EPDM, may be employed.

The amount of blend of such other rubber may preferably such that the content of the second copolymer (I-2) according to the present invention may desirably be at least 10% by weight, preferably at least 20% by weight, based on the total amount of such other rubber and the second copolymer (I-2), i.e. the ethylene/α-olefin/triene random copolymer. When the content of the second copolymer (I-2) i.e. the ethylene/α-olefin/triene random copolymer, is in this range, better material properties as a rubber composition will be revealed.

The second composition according to the present invention may favorably contain the second copolymer (I-2), i.e. the ethylene/α-olefin/triene random copolymer in an amount of at least 20% by weight, preferably at least 25% by weight, based on the total amount of the composition. When the content of the second copolymer (I-2) i.e. the ethylene/α-olefin/triene random copolymer, is in this range, better material properties as a rubber composition will be revealed.

The second composition according to the present invention can be utilized widely as the raw material for rubber products, such as automobile parts, automobile shock-damping rubber, industrial rubber products, electric insulator, articles for constructional uses and rubber-lined cloth, in particular, as the starting rubber material for extrusion-molded articles, such as sealants, glass run channel, wiper blade and sponge rubber weather strip; and injection-molded and transfer-molded articles, such as in-mold foamed sponge rubber article and sponge rubber seals for automobile doors;

Concrete examples of the sealant rubber include cup for the brake master cylinder in hydraulic brake, cup for brake wheel cylinder, sealing element and O-ring for hydraulic controller of brake, cup for clutch cylinder, sealing elements for sealing between the window glass and sash, sealing element for automobile window sash and packing for home jar.

When the second composition according to the present invention is used for producing the above-mentioned articles, such as the sealing rubber, rubber element for glass run channel, wiper blade, sponge rubber weather strip, sponge rubber in-mold foamed molded article, they can be produced at a high productivity with superior material properties, such as rubbery elasticity, weatherability, heat resistance, fastness to ozone and low-temperature flexibility, by a high velocity vulcanization. For example, a sponge rubber weather strip can be produced at a high productivity by subjecting the extruded formed article by attaining vulcanization within a short period of time. Here, the vulcanization can proceed sufficiently within such a short time satisfactory and the resulting product has a superior rubbery elasticity.

The second composition according to the present invention can be prepared from the second copolymer according to the present invention (I-2), i.e. the ethylene/α-olefin/triene random copolymer and other components mentioned above by a commonly employed method for preparing rubber compounds. For example, the second copolymer (I-2), i.e. the ethylene/α-olefin/triene random copolymer and other components to be compounded are kneaded on an internal mixer, such as Bumbury mixer, kneader and intermix, at a temperature of 80–170° C. for 3–10 minutes, and, after admixing thereto, if necessary, a vulcanizing agent (II), a vulcanization accelerator, a vulcanization assistant and a foaming agent, the resulting compound is further kneaded on a roller, such as an open roll, or on a kneader at a roller temperature of 40–80° C. for 5–30 minutes, before it is subdividedly discharged out. In this manner, a rubber composition (compounded rubber) in a form of usually of a ribbon or sheet can be obtained. If the kneading temperature in the internal mixer is lower, it is possible to knead the composition together with the vulcanizing agent (II), vulcanization accelerator and foaming agent simultaneously.

Vulcanized product (vulcanized rubber product) of the second composition can be produced by preforming the unvulcanized composition into a desired shape by means of various forming techniques usually using a forming apparatus, such as extrusion molding machine, calendering rolls, press, injection molding machine or transfer molding machine. Vulcanization of the so-preformed areen product is realized by heating it, either during the preforming or after having been transfered to a vulcanizing vessel, or by irradiating it by an electron beam.

Foamed articles can be obtained using an unvulcanized starting rubber blend containing a foaming agent and vulcanizing it by procedures as given above, wherein the rubber blend is subjected to foaming during the vulcanization simultaneously, whereby formed and vulcanized article can be obtained.

The heating for the vulcanization may preferably be effected in a heating vessel by hot air, glass beads fluidizing bed, UHF (ultra high frequency radio wave), steam or LCM (hot molten salt vessel) at a temperature of 150–270° C. for 1–30 minutes.

The electron beam irradiation for vulcanization without using vulcanizing agent (II) may preferably be effected with an electron beam having an energy of 0.1–10 MeV, preferably 0.3–2 MeV so as to provide an absorbed dose of 0.5–35 Mrad, preferably 0.5–10 Mrad.

The molding with vulcanization may be realized with or without using a metal mold. In case of without using metal mold, the rubber composition is usually molded with vulcanization in continuous mode.

The rubber products, molded and vulcanized as above, can serve for various applications, including parts for automobile industry, such as weather strips, door glass run channel, window sash, radiator hose, brake parts, wiper blade, brake cap, ceiling member, air bag cover, instrument panel, trims, controller knob and seat belt cover; shock damping rubber products for automobile, such as tire tread, tire side wall and engine mount; industrial rubber products, such as rubber rollers, belts, packings and hoses; electric insulators for anode cap, grommet and cables; materials for architectural and constructional uses, such as gaskets for buildings, land cover sheet and roofing sheet; and others including rubber coated cloth, electroconductive rubber, high hardness rubber and skin sheet.

The foamed vulcanization products obtained by heat-foaming a rubber composition containing a foaming agent can be used for forming, such as weather strip, and for heat insulation, cushioning and sealing.

In case the formed product made of the second composition according to the present invention is sheet or film, it may be a laminate made by laminating on a layer consisting of the second composition according to the present invention with one or more layers of other rubber or resin to form a composite sheet or film. For such other material, there may be employed, for example, conjugated diene rubbers mentioned above, ethylene/α-olefin copolymer rubbers, polyethylene, polypropylene and polybutene.

The second copolymer (I-2) according to the present invention, i.e. the ethylene/α-olefin/triene random copolymer, may be used as a resin composition by blending it with resins, for example, polyolefin resin, such as polyethylene, polypropylene, polybutene; AES and ABS. Here, the blending proportion may preferably such that the content of the second copolymer (I-2), namely, the ethylene/α-olefin/triene random copolymer, will amount to 10% by weight or greater, preferably 20% by weight or more, based on the total weight of the resin and the second copolymer (I-2). For performing the blending, additives, such as a softening component based on butyl rubber or based on polypropylene, oils, styrene/ethylene/butene/styrene blockcopolymer (SEBS) and styrene/ethylene/propylene/styrene blockcopolymer (SEPS), may be admixed in addition to the second copolymer (I-2), i.e. ethylene/α-olefin/triene random copolymer, and the blending resins, such as polyethylene, polypropylene and polybutene.

In the resin composition mentioned above composed of the second copolymer (I-2) according to the present invention, i.e. the ethylene/α-olefin/triene random copolymer, blended with polyolefin resin and so on, better rubbery characteristic features as a rubber composition can be developed by subjecting the second copolymer (I-2), i.e. ethylene/α-olefin/triene random copolymer, to a cross linking. As the cross linking agent, there may be employed, for example, peroxides, sulfur compounds, phenol resins and quinoid compounds. As the cross linking technique, a dynamic cross linking may faborably be employed, in order to attain cross linking simultaneously with the kneading, by using an extruder or the like.

<<The Third Copolymer {α-Olefin/Triene Random Copolymer (I-3)}>>

Now, the description is directed to the third copolymer (I-3) according to the present invention, i.e. an α-olefin/triene random copolymer.

The structural units derived from the α-olefins constituting the third copolymer (I-3) of the present invention, i.e. an α-olefin/triene random copolymer, are composed of a structural unit ($U_{A-2}$) derived from an α-olefin (A-2) having at least 3, preferably 3–20 carbon atoms, and a structural unit ($U_{A-3}$) derived from another α-olefin (A-3) having at least 2, preferably 2–20 carbon atoms, which is different from the first said structural unit ($U_{A-2}$).

As the α-olefins, from which the structural units ($U_{A-2}$) and ($U_{A-3}$) are derived, there may be enumerated concretely, for example, ethylene, propylene, 1-butene, 1-pentene, 1-hexene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 1-octene, 1-decene, 1-dodecene, 1-tetradecene, 1-hexadecene, 1-octadecene and 1-eicosene. Of course the structural unit ($U_{A-2}$) is not derived from ethylene.

As preferable combinations of the structural units ($U_{A-2}$) and ($U_{A-3}$), the following (U-I) and (U-II) may be given:

(U-I): a combination in which the structural unit ($U_{A-2}$) is derived from propylene or from 4-methyl-1-pentene and the structural unit ($U_{A-3}$) is derived from ethylene, 1-butene, 1-pentene, 1-hexene or an α-olefin having 7–20 carbon atoms. Here, the α-olefin favorable for the structural unit ($U_{A-3}$) is ethylene, 1-butene, 1-hexene and 1-octene, wherein preferred structural unit ($U_{A-3}$) is those of linear ones.

(U-II): a combination in which the structural unit ($U_{A-2}$) is derived from an α-olefin having 6–20 carbon atoms and the structural unit ($U_{A-3}$) is derived from ethylene, propylene or 4-methyl-1-pentene. Here, the α-olefin favorable for the structural unit ($U_{A-2}$) is 1-hexene, 1-octene and 1-decene, wherein preferred structural unit ($U_{A-2}$) is those of linear ones.

When the combination of the structural units ($U_{A-2}$) and ($U_{A-3}$) belongs to (U-I), a copolymer having a high hardness and capable of being vulcanized at higher velocity can be obtained.

When the combination of the structural units ($U_{A-2}$) and ($U_{A-3}$) belongs to (U-II), a copolymer having a low hardness and capable of being vulcanized at higher velocity can be obtained.

The third copolymer (I-3) according to the present invention, i.e. the α-olefin/triene random copolymer, is further constituted of the structural unit ($U_{B-2}$) derived from the linear triene compound (B-2) represente by the formula (2).

Among the linear triene compounds (B-2) represented by the formula (2), those in which both $R^3$ and $R^4$ represent methyl are preferred. The third copolymer (I-3) according to the present invention, i.e. the α-olefin/triene random copolymer, obtained using, as the starting comonomer, such linear triene compound (B-2), is particularly superior in the balance between the vulcanization velocity and the scorching profile.

As the linear triene compound (B-2) represented by the formula (2), 4,8-dimethyl-1,4,8-decatriene (DMDT) is preferred.

The linear triene compound (B-2) represented by the formula (2) has usually a stereoisomerism (trans- and cis-isomers). The linear triene compound (B-2) to be used as a comonomer may be either a mixture of trans- and cis-isomers or each sole isomer of trans- or cis-structure.

In the third copolymer (I-3) according to the present invention, i.e. an α-olefin/triene random copolymer, the structural units ($U_{A-2}$), ($U_{A-3}$) and ($U_{B-2}$) are bound with each other in a random distribution and the structural unit ($U_{B-2}$) has unsaturation bonds derived from the linear triene compound (B-2) represented by the formula (2).

The main chain of the third copolymer (I-3), i.e. the α-olefin/triene random copolymer, according to the present invention has substantially a linear structure. The assumption that the third copolymer (I-3), i.e. the α-olefin/triene random copolymer, has substantially a linear structure and does not substantially contain a cross-linked gelled molecular structure can be ascertained by the fact that this copolymer dissolves in an organic solvent while exhibiting substantially no insoluble residue. For example, this can be ascertained by the fact that the copolymer (I-3) dissolves completely in decalin at 135° C. upon the determination of its intrinsic viscosity [θ].

The third copolymer(I-3) according to the present invention, i.e. an α-olefin/triene random copolymer, has a content of the structural unit ($U_{A-2}$) in a range from 70 to 99.9 mole %, preferably from 75 to 95 mole %, a content of the structural unit ($U_{A-3}$) in a range from 0 to 29.9 mole %, preferably from 1 to 25 mole %, and a content of the structural unit ($U_{B-2}$) in a range from 0.1 to 30 mole %, preferably from 0.2 to 10 mole %, provided that the total sum of the contents of these structural units ($U_{A-2}$), ($U_{A-3}$) and ($U_{A-2}$) amounts to 100 mole %.

When the contents of these structural units are in the above ranges, such third copolymer (I-3) according to the present invention, i.e. the α-olefin/triene random copolymer, exhibits favorable rubbery material properties.

The third copolymer (I-3) can be utilized for various applications including the starting material of various rubber products and as a modifier for various resins and, concretely, can be utilized favorably as the starting material for extrusion-molded articles, such as glass run channel, wiper blade and sponge rubber weather strip, for injection molded articles and for transfer-molded articles, such as in-mold foaming-molded spongy articles.

In the third copolymer (I-3) according to the present invention, i.e. the α-olefin/triene random copolymer, the structural unit ($U_{B-2}$) derived from the linear triene compound (B-2) has a molecular structure substantially represented by the formula (2-a). The fact that the structural unit derived from the linear triene compound (B-2) has the structure represented by the formula (2-a) can be confirmed by inspecting the third copolymer (I-3), i.e. the α-olefin/triene random copolymer, by $^{13}$C-NMR spectrometry.

The third copolymer (I-3) according to the present invention, i.e. the α-olefin/triene random copolymer, may have, copolymerized therein, further structural unit(s) of other copolymerizable comonomer(s) than those of the α-olefin and the linear triene compound (B-2) represented by the formula (2). For such other comonomer(s), non-conjugate dienes and cycloolefins may be enumerated. The content of the structural unit derived from such other comonomer should favorably be 30 mole % or less, preferably 0.5–10 mole %, based on the total moles of all the structural units. For such other monomer(s), the same ones as those exemplified for the second copolymers may be employed.

The third copolymer (I-3) according to the present invention, i.e. the α-olefin/triene random copolymer, can be vulcanized at high velocty and is superior in the scorch stability, together with superiority in weatherability, heat resistance and fastness to ozone.

The third copolymer (I-3) according to the present invention, i.e. the α-olefin/triene random copolymer, may be brought into practical use not only in the unvulcanized state as such but also in the vulcanized form by subjecting it to vulcanization by the procedures described afterwards, wherein development of the advantageous characteristic features thereof is facilitated by vulcanization. On vulcanization, a high vulcanization velocity is attained, though the term till scorching is not reduced.

The third copolymer (I-3) according to the present invention, i.e. the α-olefin/triene random copolymer, can be used especially favorably for the starting material for various rubber products and as a resin modifier.

As the rubber products, there may be exemplified automobile parts, industrial rubber products, electric insulator, articles for constructional uses and rubber-lined cloth. Concrete examples include glass run channel, wiper blade, weather strip, sponge, hoses, grommet, side wall of tire, sheath for electric cable and gaskets.

When the third copolymer (I-3) according to the present invention, i.e. the α-olefin/triene random copolymer, is added as a resin modifier to resins, such as polypropylene, polyethylene, polybutene and polystyrene, the shock resistance and the resistance to stress cracking of the resin can be increased greatly.

When the combination of the structural units ($U_{A-2}$) and ($U_{A-3}$) belongs to (U-I), such a copolymer has a high hardness and is capable of being vulcanized at higher velocity.

When the combination of the structural units ($U_{A-2}$) and ($U_{A-3}$) belongs to (U-II), such a copolymer has a low hardness and is capable of being vulcanized at higher velocity.

The third copolymer (I-3) according to the present invention, i.e. the α-olefin/triene random copolymer, may be vulcanized solely or co-vulcanized together with other rubber material.

The third copolymer (I-3) according to the present invention, i.e. the α-olefin/triene random copolymer, can, due to the high vulcanization velocity, be vulcanized within a shorter vulcanization time or at a lower vulcanization temperature without using a large amount of vulcanizing agent, as compared with conventional unsaturated copolymers based on olefin. The third copolymer (I-3) according to the present invention, i.e. the α-olefin/triene random copolymer, has a superior scorch stability, so that it can be processed by foaming molding with a stable expansion ratio and, thus, an increased productivity of foamed article can be attained. Thus, the foaming expansion ratio is determined by a delicate balance between the initial viscosity of the raw resin material, the rate of elevation of the viscosity during the molding and the rate of decomposition of the foaming agent, so that control of the expansion ratio is difficult, since the higher the viscosity elevation rate, the greater will be the variation in the viscosity change rate. However, the scorch stability is superior and, thus, the viscosity elevation is lower in the third copolymer (I-3) according to the present invention, i.e. the α-olefin/triene random copolymer, so that it permits to produce a foamed molded article at a stable expansion ratio efficiently. The third copolymer (I-3) according to the present invention, i.e. the α-olefin/triene random copolymer, is superior also in the processing stability during working due to its superior scorch stability and, therefore, any troublesome phenomenon caused from viscosity increase upon working, for example, on an extruder, such as reduction in the extrusion output, increase in the motor load and stuffing or clogging of the cylinder and/or the die due to elevation of the viscosity by the progress of vulcanization within the extruder, can be prevented.

It is a further advantageous feature of the third copolymer (I-3), i.e. the α-olefin/triene random copolymer, according to the present invention, that it excells in the fastness to thermal debasement while maintaining the superior characteristic features mentioned above.

<<Production of the Third Copolymer (I-3), i.e. the α-Olefin/Triene Random Copolymer>>

The third copolymer (I-3) according to the present invention, i.e. the α-olefin/triene random copolymer, can be produced by the same procedures as in the production of the second copolymer according to the present invention as described previously. Thus, it can be produced by co-polymerizing the α-olefin having 2–20 carbon atoms, the linear triene compound (B-2) represented by the formula (2) and, if necessary, other comonomer(s) to be incorporated optionally in the presence of the same catalyst as that exemplified in the production of the second copolymer described above under the same condition.

The third copolymer (I-3) according to the present invention, i.e. the α-olefin/triene random copolymer, obtained in this way is capable of being vulcanized at higher velocity and superior in the scorch stability together with superiorities in the weatherability, heat resistance and fastness to ozone, so that it can be utilized for applications, such as the starting material for various rubber products and as modifier for resins. Vulcanized rubber products obtained by vulcanization of the third copolymer (I-3) according to the present invention, i.e. the α-olefin/triene random copolymer, are superior not only in the weatherability, heat resistance and fastness to ozone, but also in the rubbery elasticity. On producing vulcanized rubber products using the third copolymer (I-3) according to the present invention, i.e. the α-olefin/triene random copolymer, it can be worked by a high velocity vulcanization and, therefore, a high productivity can be attained.

The third composition according to the present invention comprises the third copolymer (I-3) according to the present invention, i.e. the α-olefin/triene random copolymer, the vulcanizing agent (II) and/or the filler (III). The third composition according to the present invention consists of a vulcanizable rubber composition, which can be brought into practical use in the unvulcanized state as such, though it can develop more advantageous features when used in a vulcanized form.

The vulcanized rubber products obtained by vulcanization of the third composition according to the present invention are superior not only in the weatherability, heat resistance, fastness to ozone and fastness to dynamic fatigue but also in the rubbery elasticity and low temperature flexibility. On producing vulcanized rubber products using the third composition according to the present invention, a high productivity can be attained, since the third copolymer (I-3) according to the present invention, i.e. the α-olefin/triene random copolymer, can be vulcanized at higher velocity. It is also possible to reduce the amount of the vulcanizing agent (II) and that of vulcanization accelerator to be incorporated, so that vulcanized rubber product exhibiting superior appearance with lower degree of blooming can be obtained.

The third composition according to the present invention can be vulcanized in the same way as in the case of the second composition as described previously. Thus, it can be vulcanized by blending it with the compounds constituting the vulcanization system, such as the vulcanizing agent (II), a vulcanization accelerator, a vulcanization assistant and so on, and effecting the vulcanization of the blend under the same condition as in the case of the second composition described above.

As the filler (III) to be incorporated in the third composition according to the present invention, the same reinforcing agent and softener as in the case of the second composition described previously may be enumerated. The amount of these reinforcing agent and softener to be incorporated in the composition may also be the same as in the second composition described above.

There may be blended with the third composition according to the present invention, in addition to the abovementioned components, other ingredients and chemicals, including compounds constituting a foaming system, such as foaming agent and foaming assistant, antioxidant (stabilizer), processing assistant, plasticizer, colorant and other rubber components. The kinds and amounts of these other ingredients may be selected so as to cope with each requirement.

The third composition according to the present invention may be processed by foaming molding when it contains compounds constituting a foaming system, such as foaming agent and foaming assistant. The foaming molding can also be carried out in the same manner as in the case of the second composition described above. Thus, the foaming agent and foaming assistant identical with those in the case of the second composition described above are used in also the same amounts.

As the antioxidant (stabilizer) and processing assistant permitted to be incorporated as other ingredients in the third composition according to the present invention, the same ones as in the case of the second composition may be employed, also in the same amount as that case.

The third composition according to the present invention may contain other known rubber component(s) than the third copolymer (I-3), i.e. the α-olefin/triene random copolymer, within an extent not obstructing the purpose of the present invention. Such other rubber component(s) may be the same as that given in the case of the second composition described above and the amount thereof is also the same, whereby better material properties as a composite rubber can be developed.

The third composition according to the present invention may preferably contain the third copolymer (I-3), i.e. the α-olefin/triene random copolymer, in an amount of at least 20%, preferably at least 25%, based on the total weight of the composition. When the content of the third copolymer (I-3), i.e. the α-olefin/triene random copolymer, is in the above range, better material properties as a composite rubber can be developed.

The third composition according to the present invention can be utilized as the raw material for rubber products, such as automobile parts, automobile shock-damping rubber, industrial rubber products, electric insulator, articles for constructional uses and rubber-lined cloth, in particular, as the starting rubber material for extrusion molded articles, such as sealants, glass run channel, wiper blade and sponge rubber weather strip; injection-molded and transfer-molded articles, such as in-mold foamed sponge rubber articles and sponge rubber seals for automobile doors. Concrete examples of the sealant rubber include those which are enumerated in the case of the second composition described above.

When the third composition according to the present invention is used for starting material for sealants, glass run channel, wiper blade, sponge rubber weather strip and in-mold foamed articles as mentioned above, they can be produced at a high productivity by high velocity vulcanization and are superior in the rubbery elasticity, weatherability, heat resistance, fastness to ozone and low-temperature flexibility. For example, sponge rubber weather strip can be produced at a high productivity by vulcanization of the extruded green product within a short period of time. Here, the vulcanization proceeds sufficiently within a short time to provide the end product having superior rubbery elasticity.

The third composition according to the present invention can be prepared in the same manner as in the case of the second composition according to the present invention described above except that the third copolymer (I-3), i.e. the α-olefin/triene random copolymer, is incorporated.

The vulcanized product (vulcanized rubber product) of the third composition according to the present invention can be obtained by preforming the unvulcanized composition into a desired shape by means of various forming techniques usually using a forming apparatus, such as extrusion molding machine, calendering rolls, press, injection molding machine or transfer-molding machine and heating the preformed green product at the same time with the preforming or after the green product has been guided into a vulcanization vessel or irradiating the preformed green product with electron beam to attain vulcanization. For foamed article, the unvulcanized composition which contains a foaming agent is subjected to vulcanization in the same manner as above, whereby foaming is caused simultaneously with the vulcanization and, thus, foamed product is obtained. The process herein is also the same as in the case of the second composition described above.

The vulcanized rubber products and vulcanized foamed articles formed and vulcanized in this manner can be used for the same applications as in the case of the second composition described above.

In case the formed product made from the third composition according to the present invention is a sheet or a film, it may be a laminate in which another layer made of other rubber or resin is laminated on a layer made of the third composition according to the present invention to build up a composite sheet or film. As the material for such another layer, there may be employed, for example, a rubber based on conjugated diene, a rubber based on ethylene/α-olefin copolymer, polyethylene, polypropylene or polybutene.

The third copolymer (I-3) according to the present invention, i.e. the α-olefin/triene random copolymer, can be used in a form of a resin composition by blending it with resin(s), for example, polyolefin resins, such as polyethylene, polypropylene and polybutene; and resins, such as AES and ABS. Here, the conditions of blending proportion, other additives, such as softening ingredients and so on, to be employed may be the same as in the case of the second composition according to the present invention described above. Also, the cross linking agent and the cross linking method to be employed may be the same as in the case of the second composition described above.

As detailed above, the present invention provides a novel and useful linear triene compound as well as a process for the production thereof. The linear triene compound according to the present invention can build up, when co-polymerized with an α-olefin, an ethylenically unsaturated copolymer superior in the weatherability, heat resistance and fastness to ozone and also in the scorch stability and is capable of being vulcanized at higher velocity. By the process according to the present invention, the linear triene compound mentioned above can be produced in a simple manner at a very high yield.

According to the present invention, it is also possible to obtain a novel and useful α-olefin/triene random copolymer which can be vulcanized at higher velocity and is superior in the scorch stability. The vulcanize rubber obtained by vulcanizing the α-olefin/triene random copolymer according to the present invention is superior not only in the weatherability, heat resistance and fastness to ozone, but also in the rubbery elasticity.

The composition according to the present invention comprises the above-mentioned copolymer and a cross linking agent and/or a filler and can be vulcanized at higher velocity and is superior in the scorch stability. The vulcanized rubber obtained by vulcanizing the composition according to the present invention is superior not only in the weatherability, heat resistance and fastness to ozone, but also in the rubbery elasticity.

The formed articles according to the present invention are made of the above-mentioned composition, so that they are superior in the scorch stability and can be produced by a high velocity vulcanization. The vulcanized formed articles are superior not only in the weatherability, heat resistance and fastness to ozone, but also in the rubbery elasticity.

THE BEST MODE FOR EMBODYING THE INVENTION

Below, the present invention is described in more detail by way of Examples, wherein it is to be noted that the present invention should never be restricted by such Examples. In Examples, the conversion rate of the starting triene compound having a conjugated diene structure is calculated from the following equation in which $c_o$ represents the starting charged amount in moles of the triene compound having the conjugated diene structure and c represent the final amount thereof after the reaction in moles.

$$\text{Conversion rate } (\%) = \{(c_o - c)/C_o\} \times 100$$

The yield of the objective product is calculated from the following equation in which p represents the amount of the objective prodct in moles.

$$\text{Yield } (\%) = (p/c_o) \times 100$$

EXAMPLE 1-1

In an autoclave of stainless steel (SUS 316) of a capacity of 50 ml, there were charged under a nitrogen atmosphere 0.257 g (1.47 mmol) of cobalt(II) thiocyanate, 0.893 g (2.93 mmol) of tri-o-tolylphosphine, 5 ml of toluene and 7.56 g (55.5 mmol) of 2,6-dimethy-1,3,6-octatriene and the mixture was agitated at room temperature for 30 minutes. Then, thereto were added 15.5 ml (14.4 mmol) of a toluene solution of triethylaluminum (0.95 mole per liter) and the autoclave was closed. Ethylene was then introduced into the autoclave by connecting an ethylene bomb directly to the autoclave until an internal pressure of 1 MPa (10 kgf/cm$^2$, gauge) was reached, whereupon the autoclave was heated at 80° C. While supplementing the consumed amount of ethylene intermittently to maintain the ethylene pressure at a value within the range of 0.9 to 1 MPa (9–10 kgf/cm$^2$, gauge), the reaction was conducted at 80° C. for 5 hours.

After the reaction, the autoclave was cooled and opened, whereupon the reaction mixture was poured into 50 ml of water and the mixture was subjected to a phase separation into an organic layer and an aqueous layer. The organic layer was filtered to remove solids and was inspected by a gas chromatography. It was found that the yield of the objective product, 4,8-dimethyl-1,4,8-decatriene, was 53% (conversion rate of 2,6-dimethyl-1,3,6-octatriene was 79%).

The organic layer containing 4,8-dimethyl-1,4,8-decatriene was then subjected to a rectification under reduced pressure on a distillation column of 30 stages. There were obtained 3.3 grams of the objective compound 4,8-dimethyl-1,4-8-decatriene.

Analytical results of the so-obtained 4,8-dimethyl-1,4,8-decatriene are recited below:
(1) Boiling point: 91° C./20 mm Hg
(2) Mass spectrum: m/z 164 ($M^+$ molecular ion peak), 149, 135, 123, 108, 95, 79, 67, 55, 41
(3) $^1$H-NMR spectrum (solvent: $CDCl_3$) absorption peaks: ppm ($\delta$)
  1.55 (3H, doublet)
  1.65 (6H, doublet)
  2.05 (4H, multiplet)
  2.75 (2H, doublet)
  4.95 (2H, multiplet)
  5.2 (2H, multiplet)
  5.7 (1H, multiplet)
The molecular structure of the obtained product 4,8-dimethyl-1,4,8-decatriene is recited below:

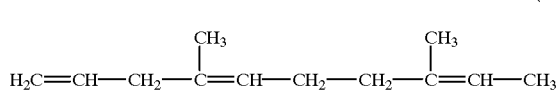

(28)

EXAMPLE 1-2

In an autoclave of stainless steel (SUS 316) of a capacity of 50 ml, there were charged under a nitrogen atmosphere 0.128 g (0.44 mmol) of cobalt(II) nitrate hexahydrate, 0.082 g (0.84 mmol) of potassium thiocyanate, 10 ml of toluene and 3.0 g (22 mmol) of 2,6-dimethy-1,3,6-octatriene and the mixture was agitated at room temperature for 30 minutes. Then, thereto were added 2.2 ml (2.1 mmol) of a toluene solution of triethylaluminum (0.95 mole per liter) and the autoclave was closed. Ethylene was then introduced into the autoclave by connecting an ethylene bomb directly to the autoclave until an internal pressure of 2 MPa (20 kgf/cm$^2$, gauge) was reached, whereupon the autoclave was heated at 80° C. While supplementing the consumed amount of ethylene intermittently to maintain the ethylene pressure at a value within the range of 1.9 to 2 MPa (19–20 kgf/cm$^2$, gauge), the reaction was conducted at 80° C. for 5 hours.

After the reaction, the analysis was carried out in the same manner as in Example 1-1 by a gas chromatography. It was found that the yield of the objective product, 4,8-dimethyl-1,4,8-decatriene, was 72% (conversion rate of 2,6-dimethyl-1,3,6-octatriene was 97%).

EXAMPLE 1-3

In an autoclave of stainless steel (SUS 316) of a capacity of 50 ml, there were charged under a nitrogen atmosphere 0.123 g (0.42 mmol) of cobalt(II) acetylacetonate dehydrate, 0.082 g (0.84 mmol) of potassium thiocyanate, 10 ml of toluene and 3.0 g (22 mmol) of 2,6-dimethy-1,3,6-octatriene and the mixture was agitated at room temperature for 30 minutes. Then, thereto were added 2.2 ml (2.1 mmol) of a toluene solution of triethylaluminum (0.95 mole per liter) and the autoclave was closed. Ethylene was then introduced into the autoclave by connecting an ethylene bomb directly to the autoclave until an inner pressure of 1 MPa (10 kgf/cm$^2$, gauge) was reached, whereupon the autoclave was heated at 100° C. While supplementing the consumed amount of ethylene intermittently to maintain the ethylene pressure at a value within the range of 0.9 to 1 MPa (9–10 kgf/cm$^2$, gauge), the reaction was conducted at 100° C. for 5 hours.

After the reaction, the reaction product was analysed on a gas chromatography in the same manner as in Example 1-1. It was found that the yield of the objective product, 4,8-dimethyl-1,4,8-decatriene, was 66% (conversion rate of 2,6-dimethyl-1,3,6-octatriene was 79%).

EXAMPLE 1-4

In an autoclave of stainless steel (SUS 316) of a capacity of 50 ml, there were charged under a nitrogen atmosphere 0.109 g (0.42 mmol) of cobalt(II) acetylacetonate, 0.059 g (0.81 mmol) of methyl thiocyanate, 10 ml of toluene and 3.0 g (22 mmol) of 2,6-dimethy-1,3,6-octatriene and the mixture was agitated at room temperature for 30 minutes. Then, thereto were added 4.5 ml (4.2 mmol) of a toluene solution of triethylaluminum (0.95 mole per liter) and the autoclave was closed. Ethylene was then introduced into the autoclave by connecting an ethylene bomb directly to the autoclave until an inner pressure of 1 MPa (10 kgf/cm$^2$, gauge) was reached, whereupon the autoclave was heated at 100° C. While supplementing the consumed amount of ethylene intermittently to maintain the ethylene pressure at a value within the range of 0.9 to 1 MPa (9–10 kgf/cm$^2$, gauge), the reaction was conducted at 100° C. for 1 hour.

After the reaction, the reaction product was analysed on a gas chromatography in the same manner as in Example 1-1. It was found that the yield of the objective product, 4,8-dimethyl-1,4,8-decatriene, was 61% (conversion rate of 2,6-dimethyl-1,3,6-octatriene was 97%).

EXAMPLE 1-5

In an autoclave of stainless steel (SUS 316) of a capacity of 50 ml, there were charged under a nitrogen atmosphere 0.0041 g (0.016 mmol) of cobalt(II) acetate tetrahydrate, 0.322 g (7.84 mmol) of acetonitrile, 10 ml of toluene and 3.0 g (22 mmol) of 2,6-dimethy-1,3,6-octatriene and the mixture was agitated at room temperature for 30 minutes. Then, thereto were added 1.38 ml (1.31 mmol) of a toluene solution of triethylaluminum (0.95 mole per liter) and the autoclave was closed. Ethylene was then introduced into the autoclave by connecting an ethylene bomb directly to the autoclave until an internal pressure of 2 MPa (20 kgf/cm$^2$, gauge) was reached, whereupon the autoclave was heated at 110° C. While supplementing the consumed amount of ethylene intermittently to maintain the ethylene pressure at a value within the range of 1.9 to 2 MPa (19–20 kgf/cm$^2$, gauge), the reaction was conducted at 110° C. for 6 hours.

After the reaction, the analysis was carried out in the same manner as in Example 1-1 by a gas chromatography. It was found that the yield of the objective product, 4,8-dimethyl-1,4,8-decatriene, was 68% (conversion rate of 2,6-dimethyl-1,3,6-octatriene was 99%).

EXAMPLE 1-6

In an autoclave of stainless steel (SUS 316) of a capacity of 50 ml, there were charged under a nitrogen atmosphere 0.0124 g (0.052 mmol) of cobalt(II) chloride hexahydrate, 0.064 g (1.56 mmol) of acetonitrile, 10 ml of toluene and 3.0 g (22 mmol) of 2,6-dimethy-1,3,6-octatriene and the mixture was agitated at room temperature for 30 minutes. Then, thereto were added 1.69 ml (1.61 mmol) of a toluene solution of triethylaluminum (0.95 mole per liter) and the autoclave was closed. Ethylene was then introduced into the autoclave by connecting an ethylene bomb directly to the autoclave until an internal pressure of 2 MPa (20 kgf/cm$^2$, gauge) was reached, whereupon the autoclave was heated at 100° C. While supplementing the consumed amount of ethylene intermittently to maintain the ethylene pressure at a value within the range of 1.9 to 2 MPa (19–20 kgf/cm$^2$, gauge), the reaction was conducted at 100° C. for 17 hours.

After the reaction, the analysis was carried out in the same manner as in Example 1-1 by a gas chromatography. It was found that the yield of the objective product, 4,8-dimethyl-1,4,8-decatriene, was 64% (conversion rate of 2,6-dimethyl-1,3,6-octatriene was 85%).

EXAMPLE 1-7

In an autoclave of stainless steel (SUS 316) of a capacity of 50 ml, there were charged under a nitrogen atmosphere 0.109 g (0.42 mmol) of cobalt(II) acetylacetonate, 0.218 g (2.11 mmol) of benzonitrile, 10 ml of toluene and 3.0 g (22 mmol) of 2,6-dimethy-1,3,6-octatriene and the mixture was agitated at room temperature for 30 minutes. Then, thereto were added 4.5 ml (4.2 mmol) of a toluene solution of triethylaluminum (0.95 mole per liter) and the autoclave was closed. Ethylene was then introduced into the autoclave by connecting an ethylene bomb directly to the autoclave until an inner pressure of 1 MPa (10 kgf/cm$^2$, gauge) was reached, whereupon the autoclave was heated at 80° C. While supplementing the consumed amount of ethylene intermittently to maintain the ethylene pressure at a value within the range of 0.9 to 1 MPa (9–10 kgf/cm$^2$, gauge), the reaction was conducted at 80° C. for 1 hour.

After the reaction, the reaction product was analysed on a gas chromatography in the same manner as in Example 1-1. It was found that the yield of the objective product, 4,8-dimethyl-1,4,8-decatriene, was 34% (conversion rate of 2,6-dimethyl-1,3,6-octatriene was 71%).

EXAMPLE 1-8

A catalyst solution for the polymerization was prepared by dissolving in toluene 0.75 mM, calculated as aluminum atom, of methyl aluminoxane and 0.0025 mM of rac-dimethylsilylene-bis{1-(2-methyl-4-phenylindenyl)} zirconium dichloride.

Separately therefrom, an autoclave having a capacity of 2 liters made of SUS steel equipped with a stirrer blade and internally replaced by nitrogen gas sufficiently was charged with 17 ml of 4,8-dimethyl-1,4,8-decatriene (DMDT) obtained in Example 1-1 and 883 ml of heptane at 23° C. To this autoclave, then, 16 N liters of propylene were introduced under ice cooling while rotating the stirrer, whereupon the autoclave was heated up to 50° C. and ethylene was pressed thereinto until the total pressure had reached 0.8 MPa (8 kgf/cm$^2$, gauge). Upon reaching the autoclave internal pressure of 0.8 MPa (8 kgf/cm$^2$, gauge), 1.0 ml of a 1.0 mM/ml hexane solution of triisobutylaluminum (TIBA) was introduced thereinto by boosting with compressed nitrogen gas. Subsequently, 3 ml of the polymerization catalyst prepared as above was introduced into the autoclave by boosting with compressed nitrogen gas to start the polymerization. The polymerization was conducted for 30 minutes while adjusting the autoclave internal temperature at 50° C. and while replenishing the autovlave with ethylene directly so as to maintain the internal pressure at 0.8 MPa (8 kgf/cm$^2$, gauge). After 30 minutes had elapsed from the start of the polymerization, 5 ml of ethanol were introduced into the autoclave using a pump to terminate the polymerization, whereupon the autoclave pressure was relieved down to atmospheric pressure. To the autoclave were then added 2 liters of methanol with agitation. The resulting polymer product containing the reaction solvent and appearing in a form similar to a rubber ball was then dried at 130° C. for 13 hours under a pressure of 80 kPa (600 Torr), whereby an ethylene/propylene/DMDT copolymer (denoted hereinafter as Copolymer A) was obtained. The characteristic features thereof are recited in Table 1-1.

This copolymer A had a mole ratio of ethylene/propylene of 69/31, an intrinsic viscosity [η] determined in decalin at 135° C. of 2.2 dl/g and a content of 4,8-dimethyl-1,4,8-decatriene (DMDT) of 1.5 mole %.

EXAMPLES 1-9 AND 1-10

In the same manner as in Example 1-8 except that the α-olefin, the amount and the kind of the polymerization catalyst used were changed as given in Table 1-1, an ethylene/propylene/DMDT copolymer (denoted hereinafter as Copolymer B) and an ethylene/1-octene/DMDT copolymer (denoted hereinafter as Copolymer C) were obtained. The characteristic features of these copolymers were as given in Table 1-1.

COMPARATIVE EXAMPLES 1-1 AND 1-2

In the same manner as in Example 1-8 except that EMND or ENB (both do not fall under the triene compound of the formula (1)) was used in the place of DMDT and the amount and the kind of the polymerization catalyst were changed as given in Table 1-2, Copolymer D and Copolymer E were produced. The characteristic features of these copolymers were as given in Table 1-2.

TABLE 1-1

|  | Example 1-8 Copolymer A | Example 1-9 Copolymer B | Example 1-10 Copolymer C |
|---|---|---|---|
| Catalyst used | *1 | *1 | *3 |
| Promoter used | *2 | *2 | *4 |
| α-olefin comonom. | Propylene | 1-octene | Propylene |
| Mole ratio of ethylene/α-olef. | 69/31 | 57/43 | 69/31 |
| Triene comonom. *5 | DMDT | DMDT | DMDT |
| Content in mole % | 1.5 | 2.8 | 1.6 |
| Intrinsic viscos. [ η ] (dl/g) | 2.2 | 1.8 | 3.4 |

TABLE 1-2

|  | Comp. Example 1-1 Copolymer D | Comp. Example 1-2 Copolymer E |
|---|---|---|
| Catalyst used | *1 | *3 |
| Promoter used | *2 | *4 |
| α-olefin comonom. | Propylene | Propylene |
| Mole ratio of ethylene/α-olef. | 69/31 | 69/31 |

TABLE 1-2-continued

|  | Comp. Example 1-1 Copolymer D | Comp. Example 1-2 Copolymer E |
|---|---|---|
| Triene comonom. *5 | EMND | ENB |
| Content in mole % | 1.5 | 2.6 |
| Intrinsic viscos. [ η ] (dl/g) | 2.3 | 3.3 |

Notes for Tables 1-1 and 1-2:
*1 rac-dimethylsilylene-bis{1-(2-methyl-4-phenyl-indenyl)}zirconium dichloride
*2 Methyl aluminoxane
*3 {dimethyl(t-butylamido)(tetramethyl-$\eta^5$-cyclo-pentadienyl) silane}titanium dichloride
*4 Triphenylcarbenium(tetrakispentafluorophenyl)borate
*5 DMDT = 4,8-dimethyl-1,4,8-decatriene
EMND = 4-ethylidene-8-methyl-1,7-nonadiene
ENB = 5-ethylidenenorbornene

EXAMPLE 1-11

On a 6 inch-roller (F/B=50/50° C.), 100 part by weight of Copolymer A obtained in Example 1-8, 5 parts by weight of zinc oxide of Grade 2, 1 parts by weight of stearic acid, 80 parts by weight of N330 carbon black (SHEEST 3, trademark, a product of Tokai Carbon K.K.), 50 parts by weight of a paraffinic process oil (SUNPAR 2280, trademark, a product of Nippon Sun Sekiyu K.K.), 1.5 part by weight of sulfur, 0.5 parts by weight of a vulcanization accelerator MBT and 1.0 part by weight of a vulcanization accelerator TMTD were kneaded to obtain an unvulcanized rubber sheet.

For the so-obtained unvulcanized rubber sheet, the parameters tc(90) and t10 at 160° C. were determined. The parameter tc(90) indicates the vulcanization velocity of rubber and the parameter t10 indicates the scorch stability of rubber and they were determined in the manner as follows: Thus, a JSR Type 3 Curelastmeter (supplied from Japan Synthetic Rubber Co., Ltd.) was employed to prepare a graph for the vulcanization curve at 160° C., on which the difference ME between the maximum torque value MH and the minimum torque value ML (ME=MH−ML) was estimated, wherein the time period till arrival at 90% ME expressed in minute refers to tc(90). This time period tc(90) is a parameter indicating the vulcanization velocity. The smaller the value of this parameter, the higher is the vulcanization velocity of the rubber. The time period till arrival at 10% ME expressed in minute refers to t10 which is a parameter indicating the scorch stability. The greater the value of this parameter, the higher is the scorch stability of the rubber.

On the other hand, a press vulcanization test was performed at 160° C. using the unvulcanized rubber sheet. The press vulcanization time was settled to be the time period of tc(90) plus 5 minutes. The results of observation of the material properties of the unvulcanized as well as the vulcanized rubber sheet are recited in Table 1-3.

COMPARATIVE EXAMPLES 1-3 AND 1-4

The procedures of Example 1-11 were repeated except that Copolymer A in Example 1-11 was replaced by Copolymer D or Copolymer E obtained in Comparative Example 1-1 or 1-2, respectively. The results are recited in Table 1-3.

TABLE 1-3

|  | Example 1-11 | Comp. Example 1-3 | Comp. Example 1-4 |
|---|---|---|---|
| Copolymer | Copolym. A | Copolym. D | Copolym. E |
| Property of unvulcanized rubber |  |  |  |
| tc(90) (min.) | 4.6 | 4.8 | 10.8 |
| t10 (min.) | 2.4 | 1.9 | 2.9 |
| Property of vulcanized rubber |  |  |  |
| Tensile strength at break (MPa) *1 | 14.5 | 15.2 | 15.8 |
| Elongation at break (%) *2 | 480 | 450 | 470 |
| Hardness JIS A *3 | 66 | 67 | 67 |

Notes:
*1 Determined according to JIS K6301
*2 Determined according to JIS K6301
*3 Determined according to JIS K6301

From Table 1-3, it is seen that the unvulcanized rubber of Example 1-11 exhibits lower tc(90) and longer t10 despite of shorter tc(90). This indicates that the vulcanization velocity is higher and the scorch stability is superior.

In contrast thereto, the unvulcanized rubber of Comparative Example 1-3 exhibits longer tc(90) and shorter t10, indicating inferior vulcanization velocity and scorch stability than that of Example 1-11. The unvulcanized rubber of Comparative Example 1-4 exhibits very long tc(90) and indicates an inferior balance between the vulcanization velocity and the scorch stability.

While the difference in t10 between the rubbers of Example 1-11 and Comparative Example 1-3 given in Table 1-3 is 0.5 minute, the corresponding practical difference in the time is significantly large. Namely, the set temperature of a practical extruder for processing rubber is usually at around 100° C. and, therefore, the difference in t10 value determined at 160° C. should appear as a more prolonged time in a practical vulcanization effected at around 100° C. Thus, troublesome phenomena caused from viscosity increase upon working, for example, on an extruder, such as decrease in the extrusion output, increase in the motor load and stuffing or clogging of the cylinder and/or the die due to increase in the viscosity by the progress of vulcanization within the extruder, can be prevented, so that the stability in handling the rubber is improved.

EXAMPLE 1-1-1

<<Synthesis of 4,8-Dimethyl-1,4,8-decatriene (DMDT)>>

An autoclave of a capacity of 1,500 ml made of a stainless steel was charged under a nitrogen gas atmosphere with 257 g (1.89 moles) of 2,6-dimethyl-1,3,6-octatriene, 500 ml of toluene, 6.18 g (35.2 mmol) of cobalt thiocyanate, 21.4 g (70.4 mmol) of tri-o-tolylphosphine and 200 ml of a toluene solution of triethylaluminum of a concentration of 1 mole per liter (triethylaluminum 200 mmol) and the autoclave was closed. Ethylene was then introduced into the autoclave by connecting an ethylene bomb directly to the autoclave until an internal pressure of 1 MPa (10 kgf/cm², gauge) was reached, whereupon the autoclavewas heated at 120° C. to effect the polymerization for 5 hours while replenishing the consumed amount of ethylene intermittently.

After the reaction, the autoclave was cooled and opened, whereupon the reaction mixture was poured into 500 ml of water and the mixture was subjected to a phase separation into an organic layer and an aqueous layer. The separated organic layer was subjected to a rectification under reduced pressure on a distillation column of 80 stages, whereby 108 grams of the objective compound 4,8-dimethyl-1,4-8-decatriene as shown by the formula (28) were obtained (yield=36%).

Analytical results of the so-obtained 4,8-dimethyl-1,4,8-decatriene are recited below:
(1) Boiling point: 91° C./20 mm Hg
(2) Mass spectrum: m/z 164 ($M^+$ molecular ion peak), 149, 135, 123, 108, 95, 79, 67, 55, 41
(3) $^1$H-NMR spectrum (solvent: $CDCl_3$) absorption peaks: ppm (δ)
  1.55 (3H, doublet)
  1.65 (6H, doublet)
  2.05 (4H, multiplet)
  2.75 (2H, doublet)
  4.95 (2H, multiplet)
  5.2 (2H, multiplet)
  5.7 (1H, multiplet)

EXAMPLE 2-1

A catalyst solution for the polymerization was prepared by dissolving in toluene 0.75 mM, calculated as aluminum atom, of methyl aluminoxane and 0.0025 mM of rac-dimethylsilylene-bis{1-(2-methyl-4-phenylindenyl)} zirconium dichloride.

Separately therefrom, an autoclave having a capacity of 2 liters made of SUS steel equipped with a stirrer blade and internally replaced by nitrogen gas sufficiently was charged with 17 ml of 4,8-dimethyl-1,4,8-decatriene (DMDT) synthesized in Example 1-1-1 and with 883 ml of heptane at 23 oc. Then, to this autoclave, 16 N liters of propylene were introduced under ice cooling while rotating the stirrer, whereupon the autoclave was heated up to 50° C. and ethylene was pressed thereinto until the total pressure had reached 0.8 MPa (8 kgf/cm$^2$, gauge). Upon reaching the autoclave internal pressure of 0.8 MPa, 1.0 ml of a 1.0 mM/ml hexane solution of triisobutylaluminum (TIBA) was introduced thereinto by boosting with compressed nitrogen gas. Subsequently, 3 ml of the polymerization catalyst prepared preliminalily as above was introduced into the autoclave by boosting with compressed nitrogen gas to start the polymerization. The polymerization was conducted for 30 minutes while adjusting the autoclave internal temperature at 50° C. and while replenishing the autovlave with ethylene directly so as to maintain the internal pressure at 0.8 MPa (8 kgf/cm$^2$, gauge). After 30 minutes had elapsed from the start of the polymerization, 5 ml of ethanol were introduced into the autoclave to terminate the polymerization, whereupon the autoclave pressure was relieved down to atmospheric pressure. To the autoclave were then added 2 liters of methanol with agitation. The resulting polymer product containing the reaction solvent and appearing in a form similar to a rubber ball was then dried at 130° C. for 13 hours under a pressure of 80 kPa (600 Torr), whereby an ethylene/propylene/DMDT copolymer (denoted hereinafter as Copolymer 2A) was obtained. The characteristic features thereof are recited in Table 2-1.

This copolymer 2A had a mole ratio of ethylene/propylene of 69/31, an intrinsic viscosity [η] determined in decalin at 135° C. of 2.2 dl/g and a content of 4,8-dimethyl-1,4,8-decatriene (DMDT) of 1.5 mole %. By inspecting this Copolymer A by $^1$H-NMR and $^{13}$C-NMR, it was ascertained that the molecular structure thereof is as represented by the formula (1-a).

EXAMPLES 2-2 AND 2-3

In the same manner as in Example 2-1 except that the α-olefin, the amount and the kind of the polymerization catalyst used were changed as given in Table 2-1, an ethylene/propylene/DMDT copolymer (denoted hereinafter as Copolymer 2B) and an ethylene/1-octene/DMDT copolymer(denoted hereinafter as Copolymer 2C) were obtained. The characteristic features of these copolymers were as given in Table 2-1.

COMARATIVE EXAMPLES 2-1 AND 2-2

In the same manner as in Example 2-1 except that EMND or ENB {these compounds do not fall under the triene compound of the formula (1)} as given in Table 2-2 was employed in the place of DMDT and that the amount and the kind of the polymerization catalyst were changed as given in Table 2-2, Copolymer 2D and Copolymer 2E were produced. The characteristic features of these copolymers were as given in Table 2-2.

TABLE 2-1

|  | Example 2-1 Copolymer 2A | Example 2-2 Copolymer 2B | Example 2-3 Copolymer 2C |
|---|---|---|---|
| Catalyst used | *1 | *1 | *3 |
| Promoter used | *2 | *2 | *4 |
| α-olefin comonom. | Propylene | 1-octene | Propylene |
| Mole ratio of ethylene/α-olef. | 69/31 | 57/43 | 69/31 |
| Triene comonom. *5 | DMDT | DMDT | DMDT |
| Content in mole % | 1.5 | 2.8 | 1.6 |
| Intrinsic viscos. [η] (dl/g) | 2.2 | 1.8 | 3.4 |

TABLE 2-2

|  | Comp. Example 2-1 Copolymer 2D | Comp. Example 2-2 Copolymer 2E |
|---|---|---|
| Catalyst used | *1 | *3 |
| Promoter used | *2 | *4 |
| α-olefin comonom. | Propylene | Propylene |
| Mole ratio of ethylene/α-olef. | 69/31 | 69/31 |
| Triene comonom. *5 | EMND | ENB |
| Content in mole % | 1.5 | 2.6 |
| Intrinsic viscos. [η] (dl/g) | 2.3 | 3.3 |

Notes for Tables 2-1 and 2-2:
*1 rac-dimethylsilylene-bis{1-(2-methyl-4-phenyl-indenyl)}zirconium dichloride
*2 Methyl aluminoxane
*3 {dimethyl(t-butylamido)(tetramethyl-$\eta^5$-cyclo-pentadienyl) silane}titanium dichloride
*4 Triphenylcarbenium(tetrakispentafluorophenyl)borate
*5 DMDT = 4,8-dimethyl-1,4,8-decatriene
EMND = 4-ethylidene-8-methyl-1,7-nonadiene
ENB = 5-ethylidenenorbornene

EXAMPLE 2-4

On a 6 inch-roller (F/B=50/50° C.), 100 parts by weight of Copolymer 2A obtained in Example 2-1, 5 parts by weight of Grade 2 zinc oxide, 1 part by weight of stearic acid, 80 parts by weight of carbon black N330 (SHEEST 3, trademark, a product of Tokai Carbon K.K.), 50 parts by weight of a paraffinic process oil (SUNPAR 2280, trademark, product of Nippon Sun Sekiyu K.K.), 1.5 part by weight of sulfur, 0.5 parts by weight of a vulcanization accelerator MBT and 1.0 part by weight of a vulcanization accelerator TMTD were kneaded to obtain an unvulcanized rubber sheet.

For the so-obtained unvulcanized rubber sheet, the parameters tc(90) and t10 were determined in the manner as given below and the press vulcanization was performed at 160° C. The press vulcanization time was settled to be the time interval of tc(90) plus 5 minutes. For the vulcanized as well as unvulcanized rubber sheets, tests were carried out for the material properties of rubber sheet. The results are recited in Table 2-3.

<<Tests for the Material Properties of Unvulcanized Rubber (Estimation of Vulcanization Velocity and Scorch Stability>>

The vulcanization velocity was estimated using a JSR Type 3 Curelastmeter (supplied from Japan Synthetic Rubber Co., Ltd.). Thus, a graph for the vulcanization curve at 160° C. was prepared, on which the difference ME between the maximum torque value MH and the minimum torque value ML (ME=MH−ML) was estimated, wherein the time period till arrival at 90% ME expressed in minute was taken as a measure of the vulcanization velocity and is referred to as tc(90). The smaller the value of tc(90), the higher is the vulcanization velocity of the rubber. On the other hand, the time period till arrival at 10% of ME expressed in minute was taken as a measure of the scorch stability and is referred to as t10. The greaterthe value of t10, the higher is the scorch stability of the rubber.

<<Properties of Vulcanized Rubber>>

For the vulcanized rubber sheet, tensile strength at break ($T_B$), elongation at break ($E_B$) and hardness were determined according to JIS K6301.

COMPARATIVE EXAMPLES 2-3 AND 2-4

The procedures of Example 2-4 were repeated except that Copolymer 2A in Example 2-4 was replaced by Copolymer 2D or Copolymer 2E obtained in Comparative Example 2-1 or 2-2, respectively. The results are recited in Table 2-3.

TABLE 2-3

|  | Example 2-4 | Comp. Example 2-3 | Comp. Example 2-4 |
|---|---|---|---|
| Copolymer | Copolymer 2A | Copolymer 2D | Copolymer 2E |
| Property of un-vulcanized rubber |  |  |  |
| tc(90) (min.) | 4.6 | 4.8 | 10.8 |
| t10 (min.) | 2.4 | 1.9 | 2.9 |
| Property of vulcanized rubber |  |  |  |
| Tensile strength at break (MPa) | 14.5 | 15.2 | 15.8 |
| Elongation at break (%) | 480 | 450 | 470 |
| Hardness JIS A | 66 | 67 | 67 |

From Table 2-3, it is seen that the unvulcanized rubber of Example 2-4 exhibits shorter tc(90) and longer t10 despite of the short tc(90). This indicates that the vulcanization velocity is higher and the scorch stability is superior.

In contrast thereto, the unvulcanized rubber of Comparative Example 2-3 exhibits longer tc(90) and shorter tlo, indicating subordinate vulcanization velocity and scorch stability than those of Example 2-4. The unvulcanized rubber of Comparative Example 2-4 exhibits very long tc(90) and indicates an inferior balance between the vulcanization velocity and the scorch stability.

While the difference in t10 between the rubbers of Example 2-4 and Comparative Example 2-3 given in Table 2-3 is 0.5 minute, the corresponding practical difference in the time is significantly large. Namely, the set temperature of a practical extruder for processing rubber is usually at around 100° C. and, therefore, the difference in t10 value determined at 160° C. should appear as a more prolonged time in a practical vulcanization effected at around 100° C. Thus, troublesome phenomena caused from viscosity increase upon working, for example, on an extruder, such as decrease in the extrusion output, increase in the motor load and stuffing or clogging of the cylinder and/or the die due to increase in the viscosity by the progress of vulcanization within the extruder, can be prevented, so that the stability in handling the rubber is improved.

EXAMPLE 2-5

In the same manner as in Example 2-1, except that the amount and the kind of the comonomers used as well as the reaction conditions were changed, Copolymer 2F as given in Table 2-4 was obtained.

On a Bumbury's mixer of a capacity of 1.7 liters (supplied from Kobe Steel, Ltd.), 100 parts by weight of Copolymer 2F obtained as above, 5 parts by weight of Grade 2 zinc oxide, 90 parts by weight of SRF carbon black (ASAHI #50, trademark, a product of ASAHI Carbon K.K.), 60 parts by weight of a paraffinic process oil and 1 part by weight of a polyethylene glycol were kneaded for 6 minutes. To the resulting kneaded mass, there were added 1.5 parts by weight of sulfur (vulcanizing agent), 0.8 part by weight of 2-mercapto-benzothiazole (vulcanization accelerator), 1.2 parts by weight of 2-(4'-morpholinodithio)benzothiazole (vulcanization accelerator), 2.0 parts by weight of zinc di-n-butyldithiocarbamate (vulcanization accelerator), 1.0 part by weight of 2-mercaptoimidazoline (vulcanization accelerator), 3.5 parts by weight of p,p'-oxybis (benzenesulfonylhydrazide) (foaming agent) and 5.0 parts by weight of a defoaming agent and the mixture was kneaded on an 8 inch-roller (F/B=40/40° C.) for 15 minutes to prepare a rubber composition (rubber blend) for sponge rubber extrusion-molded articles. This rubber composition was extruded into a tube using a 50 mm extruder equipped with a tubular die (10 mm inner diameter and 1 mm wall thickness) under a condition of die temperature of 80° C. and cylinder temperature of 60° C. The resulting molded product was subjected to a vulcanization in a hot air-heated vulcanization vessel of 220° C. for 6 minutes to obtain a vulcanized sponge rubber tubular article. For the resulting vulcanized sponge rubber and for the unvulcanized starting rubber blend before the vulcanization, the tests for their properties were carried out as given below. The results are recited in Table 2-5.

<<Tests for the Material Properties of Unvulcanized Rubber (Estimation of Vulcanization Velocity and Scorch Stability>>

The test for the material properties of the unvulcanized rubber was carried out in accordance with the prescription of JIS K 6300 and the vulcanization velocity was estimated using a JSR Type 3 Curelastmeter (supplied from Japan Synthetic Rubber Co., Ltd.). Thus, a graph for the vulcanization curve at 180° C. was prepared, on which the difference ME between the maximum torque value MH and the minimum torque value ML (ME=MH−ML) was estimated, wherein the time period till arrival at 90% ME expressed in minute was taken as a measure of the vulcanization velocity {which is referred to hereafter as tc(90)}. The smaller the value of tc(90), the higher is the vulcanization velocity of the rubber. On the other hand, the time period till arrival at 10% of ME expressed in minute was taken as a measure of the scorch stability (which is referred to hereafter as t10). The greater the value of t10, the higher is the scorch stability of the rubber.

<<Vulcanization Characteristic>>

According to JIS K6301, tensile strength at break ($T_B$), elongation at break ($E_B$) and hardness ($H_S$) were determined.

<<Permanent Compression Strain Test>>

From a vulcanized tubular sponge rubber (extrusion-molded sponge rubber article), an annular test specimen of 30 mm length was cut out, which was placed in a sponge rubber permanent compression strain testing vessel and was pressed down up to 50% of the specimen height, namely, the sponge tube diameter, whereupon the specimen was transferred into a gear oven together with the testing vessel to subject the specimen to a heat treatment at 70° C. for 100 hours under the compressed state and, then, was tested for its permanent compressive strain (CS) in accordance with the prescription of "physical test method for swollen rubber" (SRIS-0101).

<<Surface Roughness>>

Using a needle contact surface roughness detector, the surface irregularities of the sponge rubber was estimated by conversion of the observed data for the protrusions and indentations of the upper surface of the sponge rubber into digital values. In practice, the vulcanized tubular sponge rubber was cut into annular specimens of each 50 mm length, from which some are taken out to inspect the surface irregularity, in which the total sum of surface protrusion values of the ten specimens having top ranking surface protrusions ranging from the greatest to the following tenth ranking magnitude was expressed by h1 and the total sum of surface indentation values of the ten specimens having tail ranking indentations ranging from the lowest to the following tenth lower ranking magnitude was expressed by h2 and the quotient of the difference thereof (h1−h2) by numeral 10, namely (h1−−h2)/10, was assumed as the surface roughness of the sponge rubber.

EXAMPLES 2-6 TO 2-8

In the same manner as in Example 2-1 except that the monomers used, amount thereof and the reaction conditions were changed, Copolymer 2G to Copolymer 2I as given in Table 2-4 were obtained.

Then, the procedures of Example 2-5 were repeated, except that Copolymers 2G to 2I were employed instead of Copolymer 2F, in order to produce sponge rubber articles. Results are recited in Table 2-5.

COMPARATIV EXAMPLES 2-5 TO 2-8

The procedures of Example 2-5 were repeated, except that Copolymer 2J to Copolymer 2M of Table 2-4 were employed instead of Copolymer 2F, in order to produce sponge rubber articles. Results are recited in Table 2-6.

TABLE 2-4

| Co-polymer | Olefin *1) | Ethylene/olefin mole ratio | Polyene/mole % *2) | Iodine value | Intrins. viscos. (dl/g) |
|---|---|---|---|---|---|
| 2F | Propyl. | 70/30 | DMD/1.5 | 23 | 2.2 |
| 2G | Propyl. | 71/29 | DMD/1.4 | 22 | 2.3 |
| 2H | 1-butene | 75/25 | DMD/1.6 | 25 | 2.8 |
| 2I | 1-octene | 74/26 | DMD/1.4 | 22 | 3.0 |
| 2J | Propyl. | 70/30 | EMN/1.4 | 22 | 2.2 |
| 2K | Propyl. | 68/32 | EMN/0.8 | 12 | 2.2 |
| 2L | Propyl. | 71/29 | ENB/3.1 | 23 | 2.1 |
| 2M | Propyl. | 70/30 | ENB/1.5 | 12 | 2.2 |

Notes:
*1): Prop. polypropylene
*2): DMD = 4,8-dimethyl-1,4,8-decatriene
EMN = 4-ethylidene-8-methyl-1,7-nonadiene
ENB = 5-ethylidene-2-norbornene

TABLE 2-5

| | Example | | | |
|---|---|---|---|---|
| | 2-5 | 2-6 | 2-7 | 2-8 |
| Copolymer | 2F | 2G | 2H | 2I |
| Property of un-vulcanized rubber | | | | |
| tc(90) (min.) | 6.4 | 6.5 | 6.8 | 7.0 |
| t10 (min.) | 2.7 | 2.8 | 2.9 | 3.1 |
| Property of vulca-nized rubber | | | | |
| Specific weight | 0.51 | 0.50 | 0.56 | 0.49 |
| Surface roughness (μm) | 8 | 7 | 8 | 7 |
| $T_B$ (MPa) | 2.6 | 2.7 | 2.4 | 2.6 |
| $E_B$ (%) | 260 | 270 | 280 | 320 |
| CS (%) *1) | 18 | 19 | 16 | 17 |

Notes:
*1): Permanent compressive strain after standing for 100 hours at 70° C.

TABLE 2-6

| | Comparative Example | | | |
|---|---|---|---|---|
| | 2-5 | 2-6 | 2-7 | 2-8 |
| Copolymer | 2J | 2K | 2L | 2M |
| Property of un-vulcanized rubber | | | | |
| tc(90) (min.) | 6.5 | 9.5 | 12 | 17 |
| t10 (min.) | 1.9 | 2.6 | 2.8 | 3.7 |
| Property of vulca-nized rubber | | | | |
| Specific weight | 0.55 | 0.48 | 0.45 | 0.47 |
| Surface roughness (μm) | 7 | 8 | 9 | 11 |
| $T_B$ (MPa) | 2.7 | 2.3 | 2.0 | 2.1 |
| $E_B$ (%) | 280 | 340 | 290 | 300 |
| CS (%) *1) | 18 | 19 | 25 | 29 |

Notes:
*1): Permanent compressive strain after standing for 100 hours at 70° C.

EXAMPLE 2-9

In the same manner as in Example 2-1, except that the monomer used, its amount and the reaction condition were changed, Copolymer 2N as shown in Table 2-7 was obtained.

On a Bumbury's mixer of a capacity of 1.7 liters (supplied from Kobe Steel, Ltd.), 100 parts by weight of Copolymer 2N obtained as above, 5 parts by weight of Grade 2 zinc oxide, 2 parts by weight of stearic acid, 60 parts by weight of SRF carbon black (ASAHI #50, trademark, a product of ASAHI Carbon K.K.), 30 parts by weight of FEF carbon black (ASAHI #60, trademark, a product of ASAHI Carbon K.K.), 60 parts by weight of a paraffinic process oil and 2 parts by weight of calcium oxide were kneaded for 5 minutes. To the resulting kneaded mass, there were added 1.5 parts by weight of sulfur (vulcanizing agent), 2.5 parts by weight of 2-(4'-morpholinodithio)benzothiazole (vulcanization accelerator), 1.0 part by weight of zinc di-n-butyldi-thiocarbamate (vulcanization accelerator), 0.5 part by weight of tetraethylthiuram disulfide (vulcanization accelerator), 0.5 part by weight of ethylenethiourea (vulcanization accelerator), 7.0 parts by weight of diazocarbonamide (foaming agent) and 2.0 parts by weight of a foaming assistant based on urea and the mixture was kneaded on an 8 inch-roller (F/B=40/40° C.) for 15 minutes to prepare a rubber composition (rubber blend) for sponge rubber in-mold foaming-molded articles. This rubber composition was molded using an injection-molding vulcanizer into a tubular vulcanized sponge rubber having an inner diameter of 11 mm, an outer diameter of 15 mm and a length of 25 cm, at a molding temperature of 180° C. under vulcanization for 4 minutes. The results are recited in Table 2-8.

<<Tests for the Material Properties of Unvulcanized Rubber (Estimation of Vulcanization Velocity and Scorch Stability>>

The tests were the same as those given in Example 2-5.

<<(Water Absorptibility>>

A test specimen of 20 mm×20 mm is punched out from the tubular sponge rubber (the in-mold foaming-molded sponge rubber) at its upper portion and is weighed. Then, this specimen is immersed in a layer of water stored in a height of at least 100 mm above the bottom in a desiccator pot provided with a gas sucking-out nipple. Then, the desiccator is evacuated down to a reduced pressure of 635 mm Hg and the pot is held at this reduced pressure for three minutes, whereupon the reduced pressure is relieved to atmospheric pressure and is held under this condition for further three minutes. The specimen is then taken out of the desiccator and the surface water attached thereon is wiped off and the specimen is weighed again, wherein the rate of water absorption is calculated by the following arithmetic equation:

Rate of water absorption wt. %={(W2−W1)/W1}×100

In this equation, W1 represents the weight of the specimen, expressed in gram, before immersion in water and W2 represents the weight of the specimen, expressed in gram, after the immersion in water.

<<Permanent Compression Strain Test>>

The permanent compression strain test of the tubular vulcanized sponge rubber (the in-mold foaming-molded vulcanized sponge rubber) was carried out according to the prescription of JIS K6301. A permanent compressive strain after 70° C.×100 hours (CS) was determined thereby.

EXAMPLE 2-10

In the same manner as in Example 2-1, except that the monomer used, its amount and the reaction condition were changed, Copolymer 2O as shown in Table 2-7 was obtained.

Then, the procedures of Example 2-9 were repeated, except that Copolymer 2O was employed instead of Copolymer 2N, in order to produce sponge rubber articles. Results are recited in Table 2-8.

COMPARATIVE EXAMPLES 2-9 AND 2-10

The procedures of Example 2-9 were repeated, except that Copolymer 2P and Copolymer 2Q of Table 2-7 were employed instead of Copolymer 2N, in order to produce sponge rubber articles. Results are recited in Table 2-7.

TABLE 2-7

| Co-polymer | Olefin *1) | Ethylene/olefin mole ratio | Polyene/mole % *2) | Iodine value | Intrins. viscos. (dl/g) |
|---|---|---|---|---|---|
| 2N | Propyl. | 72/28 | DMD/1.2 | 19 | 1.0 |
| 2O | 1-octene | 76/24 | DMD/1.3 | 21 | 1.1 |
| 2P | Propyl. | 70/30 | EMN/1.1 | 17 | 1.0 |
| 2Q | Propyl. | 72/28 | ENB/2.9 | 22 | 1.0 |

Notes:
*1): Prop. = polypropylene
*2): DMD = 4,8-dimethyl-1,4,8-decatriene
EMN = 4-ethylidene-8-methyl-1,7-nonadiene
ENB = 5-ethylidene-2-norbornene

TABLE 2-8

| | Example | | Comp. Example | |
|---|---|---|---|---|
| | 2-9 | 2-10 | 2-9 | 2-10 |
| Copolymer | 2N | 2O | 2P | 2Q |
| Property of un-vulcanized rubber | | | | |
| tc(90) (min.) | 1.9 | 2.0 | 1.9 | 2.7 |
| t10 (min.) | 1.1 | 1.0 | 0.6 | 1.1 |
| Property of vulca-nized rubber | | | | |
| Specific weight | 0.59 | 0.55 | 0.64 | 0.60 |
| Rate of water ab-sorption (wt. %) | 10 | 8 | 12 | 22 |
| CS (%) *1) | 21 | 20 | 23 | 37 |

Notes: *1) Permanent compressive strain after standing for 100 hours at 70° C.

EXAMPLE 3-1

<<Preparation of Catalyst>>

A glass flask of which internal space had been sufficiently replaced with nitrogen gas was charged with 4.8 mg of rac-dimethylsilylene-bis{1-(2-methyl-4-phenylindenyl)}zirconium dichloride and thereto were further added 2.8 ml of a toluene solution of methylaluminoxane (prepared by evaporating a commercial product of methylaluminoxane of the firm Witco to dryness and re-dissolving the dried solid in toluene; Al concentration=1.1 mole/liter) and 4.8 ml of toluene, whereby a catalyst solution was prepared.

<<Polymerization>>

A stainless steel autoclave having an internal volume of 2 liters, of which internal space had been sufficiently replaced with nitrogen gas, was charged with 900 ml of hexane, 1 mmol of triisobutylaluminum, 70 grams of 1-butene and 15 ml of DMDT obtained in Example 1-1-1 and the temperature of the polymerization system was elevated to 70° C. By pressing into the autoclave 2 ml of the catalyst solution prepared as above (0.002 mmol of Zr) by boosting by compressed propylene, the copolymerization was initiated. The polymerization was conducted at 70° C. over a period of 30 minutes while maintaining the total pressure at 1.4 MPa (14 kgf/cm², gauge) by continuous supply of only propylene thereto. The polymerization was terminated by introducing a small amount of ethanol into the polymerization system, whereupon the unreacted comonomers were purged off. The resulting polymer solution was poured into a large excess amount of methanol to precipitate the polymer. This polymer was separated by filtration. To the so-obtained polymer, stabilizers, i.e. 25 mg of IRGANOX 1010 (trademark, a product of the firm Ciba-Geigy) and 25 mg of MARK 329K (trademark, a product of Asahi Denka Kogyo K.K.) were added and the blend was dried at 80° C. overnight under a reduced pressure.

In this way, 23.6 g of a propylene/1-butene/DMDT random copolymer (Copolymer 3A) were obtained, which had an intrinsic viscosity [η] of 2.3 dl/g, a content of the structural unit of propylene of 87.6 mole %, a content of the structural unit of 1-butene of 10.9 mole %, a content of the structural unit of DMDT of 1.5 mole % and an iodine value of 17.

EXAMPLE 3-2

<<Preparation of the Solid Titanium Catalyst Component>>

A mixture of 95.2 g of anhydrous magnesium chloride, 442 ml of decane and 390.6 g of 2-ethylhexyl alcohol was heated at 130° C. for 2 hours to react them to thereby obtain a homogeneous solution, whereto 21.3 g of phthalic anhydride were added and were dissolved therein by heating the mixture at 130° C. for 1 hour while agitation. The so-obtained homogeneous solution was cooled down to room temperature, whereupon 75 ml of the solution were dropped into 200 ml of titanium tetrachloride maintained at minus 20° C. over a period of one hour. After the dropping had been over, the temperature of the resulting mixture was elevated to 110° C. over a period of four hours. Upon reaching at 110° C., 5.22 g of diisobutyl phthalate were added thereto, whereupon the mixture was held at this temperature under agitation for two hours. After the reaction, the reaction mixture was hot-filtered to separate and collect the solid product, which was then re-slurried in 275 ml of titanium tetrachloride and was heated again at 110° C. for 2 hours to cause the reaction. After the reaction, the solid product was collected by hot-filtration again and the resulting solid product was washed sufficiently with decane and hexane of 110° C., until no free titanium compound became to be detected. The solid titanium catalyst component obtained as above was stored in a form of decane slurry. A part of this solid titanium catalyst component was dried for examining the chemical composition. It was found that this solid titanium catalyst component had a composition of 2.5% by weight of titanium, 65% by weight of chlorine, 19% by weight of magnesium and 13.5% by weight of diisobutyl phthalate.

<<Polymerization>>

A glass autoclave having an internal volume of 2 liters, of which internal space had sufficiently been replaced with nitrogen gas, was charged with 560 ml of decane, 400 ml of 1-octene and 40 ml of DMDT obtained in Example 1-1-1, whereupon the temperature of the polymerization system was elevated to 50° C. Then, hydrogen gas and nitrogen gas were passed to the autoclave each at a rate of 3 liters per hour and 50 liters per hour, respectively. The copolymerization was then initiated by intoducing 3 mmol of triisobutylaluminum, 1 mmol of trimethylethoxysilane and 0.06 mmol, calculated as titanium atom, of the catalyst prepared as above. The polymerization was conducted over a period of 30 minutes while maintaining the temperature of the polymerization system at 50° C., whereupon the polymerization was terminated by introducing a small amount of ethanol into the polymerization system. The resulting polymer solution was poured into a large excess amount of methanol to precipitate the polymer. This polymer was collected by filtration. To the so-obtained polymer, stabilizers, i.e. 50 mg of IRGANOX 1010(trademark, a product of the firm Ciba-Geigy) and 50 mg of MARK 329K (trademark, a product of Asahi Denka Kogyo K.K.) were added and the blend was dried overnight at 120° C. under a reduced pressure.

In this way, 41.6 g of a 1-octene/DMDT random copolymer (Copolymer 3B) were obtained, which had an intrinsic viscosity [η] of 5.0 dl/g, a content of the structural unit of 1-octene of 95.7 mole %, a content of the structural unit of DMDT of 4.3 mole % and an iodine value of 21.

EXAMPLE 3-3

<<Polymerization>>

A stainless steel autoclave having an internal volume of 2 liters, of which internal space had been sufficiently replaced with nitrogen gas, was charged with 900 ml of hexane, 20 ml of DMDT and 1 ml of triisobutylaluminum and the temperature of the polymerization system was elevated to 60° C. Then, by supplying ethylene to the autoclave up to an internal pressure of 0.25 MPa (2.5 kgf/cm², gauge) and pressing 1.5 ml of the catalyst solution prepared in Example 3-1 (0.0015 mmol of Zr) by boosting by compressed propylene, the copolymerization was initiated. The polymerization was conducted at 60° C. over a period of 15 minutes while maintaining the total pressure at 0.8 MPa (8 kgf/cm², gauge) by supplying continuously only propylene thereto. The procedures thereafter were the same as in Example 3-1.

In this way, 28.0 g of a propylene/ethylene/DMDT random copolymer (Copolymer 3C) were obtained, which had an intrinsic viscosity [η] of 2.0 dl/g, a content of the structural unit of propylene of 90.1 mole %, a content of the structural unit of ethylene of 8.0 mole %, a content of the structural unit of DMDT of 1.9 mole % and an iodine value of 22.

EXAMPLE 3-4

<<Preparation of the Solid Titanium Catalyst Component>>

A mixture of 95.2 g of anhydrous magnesium chloride, 442 ml of decane and 390.6 g of 2-ethylhexyl alcohol was heated at 130° C. for 2 hours to react them to thereby obtain a homogeneous solution, whereto 21.3 g of phthalic anhydride were added and were dissolved therein by heating the mixture at 130° C. for 1 hour while agitation. The so-obtained homogeneous solution was cooled down to room temperature, whereupon 75 ml of the solution were dropped into 200 ml of titanium tetrachloride maintained at minus 20° C. over a period of one hour. After the dropping had been over, the temperature of the resulting mixture was elevated to 110° C. over a period of four hours. Upon reaching at 110° C., 5.22 g of diisobutyl phthalate were added thereto, whereupon the mixture was held at this temperature under agitation for two hours. After the reaction of two hours, the reaction mixture was hot-filtered to separate and collect the solid product, which was then re-slurried in 275 ml of titanium tetrachloride and was heated again at 110° C. for 2 hours to cause the reaction. After the reaction, the solid product was collected by hot-filtration again and the resulting solid product was washed sufficiently with decane and hexane of 110° C., until no free titanium compound became to be detected. The solid titanium catalyst component obtained as above was stored in a form of decane slurry. A part of this solid titanium catalyst component was dried for examining the chemical composition. It was found that this solid titanium catalyst component had a composition of 2.5% by weight of titanium, 65% by weight of chlorine, 19% by weight of magnesium and 13.5% by weight of diisobutyl phthalate.

<<Polymerization>>

A glass autoclave having an internal volume of 1 liter, of which internal space had sufficiently been replaced with nitrogen gas, was charged with 500 ml of 4-methyl-1-pentene, 10 ml of 1-decene, 10 ml of DMDT and 1 N liter of hydrogen gas, whereupon the temperature in the polymerization system was elevated to 50° C. The copolymerization was then initiated by intoducing 1 mmol of triethylaluminum, 1 mmol of trimethylmethoxysilane and 0.005 mmol, calculated as titanium atom, of the catalyst prepared as above. The polymerization was conducted over a period of 15 minutes while maintaining the temperature of the polymerization system at 50° C., whereupon the polymerization was terminated by introducing a small amount of ethanol into the polymerization system. The resulting polymer solution was poured into a large excess amount of methanol to precipitate the polymer. This polymer was collected by filtration. To the so-obtained polymer, stabilizers, i.e. 30 mg of IRGANOX 1010 (trademark, a product of the firm Ciba-Geigy) and 30 mg of MARK 329K (trademark, a product of Asahi Denka Kogyo K.K.) were added and the blend was dried overnight at 80° C. under a reduced pressure.

There were obtained thereby 40.8 g of a 4-methyl-1-pentene/1-decene/DMDT random copolymer (Copolymer 3D) were obtained, which had an intrinsic viscosity [η] of 2.5 dl/g, a content of the structural unit of 4-methyl-1-pentene of 94.7 mole %, a content of the structural unit of 1-decene of 3.0 mole %, a content of the structural unit of DMDT of 2.3 mole % and an iodine value of 13.

The chemical composition of the Copolymer 3A to Copolymer 3D and so on are recited in Table 3-1.

TABLE 3-1

| Example | 3-1 | 3-2 | 3-3 | 3-4 |
|---|---|---|---|---|
| Copolymer | 3A | 3B | 3C | 3D |
| Cont. of ethylene unit (mole %) | — | — | 8.0 | — |
| Cont. of propylene unit (mole %) | 87.6 | — | 90.1 | — |
| Cont. of 1-butene unit (mole %) | 10.9 | — | — | — |
| Cont. of 1-octene unit (mole %) | — | 95.7 | — | — |
| Cont. of 4MP-1 unit (mole %) | — | — | — | 94.7 |
| Cont. of 1-decene unit (mole %) | — | — | — | 3.0 |
| Cont. of DMDT unit (mole %) | 1.5 | 4.3 | 1.9 | 2.3 |
| Iodine value | 17 | 21 | 22 | 13 |
| Intrinsic viscosity [η] (dl/g) | 2.3 | 5.0 | 2.0 | 2.5 |

Notes: DMDT = 4,8-dimethyl-1,4,8-decatriene
4MP-1 = 4-methyl-1-pentene

EXAMPLE 3-5

On a 6 inch-roller (F/B=50/50° C.), 100 parts by weight of Copolymer 3B obtained in Example 3-2, 5 parts by weight of Grade 2 zinc oxide, 1 part by weight of stearic acid, 80 parts by weight of N330 carbon black (SHEEST 3, trademark, a product of Tokai Carbon K.K.), 50 parts by weight of a paraffinic process oil (SUNPAR 2280, trademark, product of Nippon Sun Sekiyu K.K.), 0.5 part by weight of sulfur, 1.5 parts by weight of a vulcanization accelerator MBT and 1.0 part by weight of a vulcanization accelerator TMDT were kneaded to obtain an unvulcanized rubber sheet.

For the so-obtained unvulcanized rubber sheet, the parameters tc(90) and t10 were determined in the manner as given below and the press vulcanization was performed at 160° C. The press vulcanization time was settled to be the time interval of tc(90) plus 5 minutes. For the vulcanized as well as unvulcanized rubber sheets, tests were carried out for the material properties of rubber sheet. The results are recited in Table 3-2.

<<Tests for the Material Properties of Unvulcanized Rubber (Estimation of Vulcanization Velocity and Scorch Stability>>

The vulcanization velocity was estimated using a JSR Type 3 Curelastmeter (supplied from Japan Synthetic Rubber Co., Ltd.). Thus, a graph for the vulcanization curve at 160° C. was prepared, on which the difference ME between the maximum torque value MH and the minimum torque value ML (ME=MH−ML) was determined, whereupon the vulcanization velocity was estimated from the time period till arrival at 90% ME expressed in minute, namely tc(90). On the other hand, the scorch stability was estimated from the time period till arrival at 10% of ME expressed in minute, namely, t10.

<<Properties of Vulcanized Rubber>>

For the vulcanized rubber sheet, tensile strength at break (TB), elongation at break (EB) and hardness were determined according to JIS K6301.

EXAMPLE 3-6

The procedures of Example 3-5 were repeated, except that Copolymer 3C obtained in Example 3-3 was used in the place of Copolymer 3B. Results are recited in Table 3-2.

COMPARATIVE EXAMPLE 3-1

The procedures of Example 3-5 were repeated except that Copolymer 3B in Example 3-5 was replaced by an ethylene/propylene/ethylidenenorbornene copolymer (Copolymer 3E) having an ethylene content of 65 mole %, a propylene content of 32 mole %, an ethylidenenorbornene content of 3 mole %, an intrinsic viscosity [η] of 2.2 dl/g and an iodine value of 23. The results are recited in Table 3-2.

TABLE 3-2

|  | Example 3-5 | Example 3-6 | Comp. Example 3-1 |
|---|---|---|---|
| Copolymer | Copolymer 3B | Copolymer 3C | Copolymer 3E |
| Property of unvulcanized rubber | | | |
| tc(90) (min.) | 5.2 | 5.5 | 10.9 |
| t10 (min.) | 3.0 | 2.9 | 3.0 |

TABLE 3-2-continued

|  | Example 3-5 | Example 3-6 | Comp. Example 3-1 |
|---|---|---|---|
| Property of vulcanized rubber |  |  |  |
| Tensile strength at break (MPa) | 12.3 | 22.1 | 14.6 |
| Elongation at break (%) | 250 | 210 | 430 |
| Hardness JIS A | 38 | 85 | 67 |

From Table 3-2, it is seen that the unvulcanized rubbers of Examples 3-5 and 3-6 exhibit longer t10 despite of shorter tc(90). This indicates that the vulcanization velocity is higher and the scorch stability is superior.

What is claimed is:

1. An α-olefin/triene random copolymer comprising a structural unit ($U_A$) derived from an α-olefin (A) having 2–20 carbon atoms and a structural unit ($U_{B-1}$) derived from a linear triene compound (B-1) represented by the following formula (1), (1)

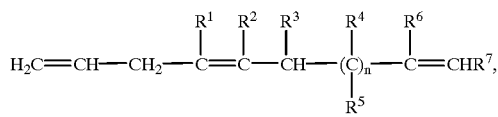

in which $R^1$, $R^2$, $R^3$, $R^4$, $R^5$ and $R^6$ stand each, independently of each other, for hydrogen atom or an alkyl having 1–3 carbon atoms, $R^7$ represents an alkyl having 1–3 carbon atoms and n is an integer of 0–5, with the proviso that each of $R^4$s or of $R^5$s may be identical with or different from each other, respectively, when n is 2 or greater, wherein the proportion of the structural unit ($U_{B-1}$) in the total of the structural unit ($U_A$) plus the structural unit ($U_{B-1}$) is in the range of 0.1–30 mole % and the intrinsic viscosity [η] determined in decalin at 135° C. is in the range of 0.1–10 dl/g.

2. The α-olefin/triene random copolymer according to claim 1, wherein the structural unit ($U_{B-1}$) derived from the linear triene compound (B-1) represented by the formula (1) is represented by the following formula (1-a), (1-a)

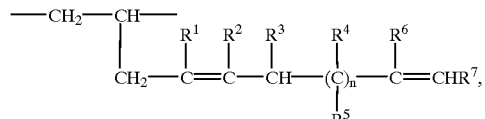

in which $R^1$, $R^2$, $R^3$, $R^4$, $R^5$ and $R^6$ stand each, independently of each other, for hydrogen atom or an alkyl having 1–3 carbon atoms, $R^7$ represents an alkyl having 1–3 carbon atoms and n is an integer of 0–5, with the proviso that each of $R^4$s or of $R^5$s may be identical with or different from each other, respectively, when n is 2 or greater.

3. The α-olefin/triene random copolymer according to claim 1, wherein, in the formula (1), n is 1 and $R^4$ and $R^5$ represent each a hydrogen atom.

4. The α-olefin/triene random copolymer according to claim 3, wherein, in the formula (1), $R^6$ and $R^7$ represent each, independently of each other, methyl group or ethyl group.

5. The α-olefin/triene random copolymer according to claim 1, wherein the α-olefin (A) comprises of two or more α-olefins.

6. The α-olefin/triene random copolymer according to claim 1, wherein the α-olefin (A) comprises of ethylene (A-1) and an α-olefin (A-2) having 3–20 carbon atoms and wherein the mole ratio of the structural unit ($U_{A-1}$) derived from ethylene (A-1) to the structural unit ($U_{A-2}$) derived from the α-olefin (A-2), namely, ($U_{A-1}$)/($U_{A-2}$) is in the range of 99/1 to 30/70.

7. The α-olefin/triene random copolymer according to claim 1, wherein the α-olefin (A) comprises of an α-olefin (A-2) having 3–20 carbon atoms and another α-olefin (A-3) having 2–20 carbon atoms and wherein the copolymer comprises 70–99.9 mole % of the structural unit ($U_{A-2}$) derived from the α-olefin (A-2) having 3–20 carbon atoms, 0–29.9 mole % of the structural unit ($U_{A-3}$) derived from the α-olefin (A-3) having 2–20 carbon atoms and 0–0.1–30 mole % of the structural unit ($U_{B-1}$) derived from the linear triene compound (B-1), assuming that the total sum of ($U_{A-2}$)+($U_{A-3}$)+($U_{B-1}$) amounts to 100 mole %.

8. The α-olefin/triene random copolymer according to claim 1, wherein, the structural unit ($U_{B-1}$) is derived from a linear triene compound (B-1) selected from the group consisting of:

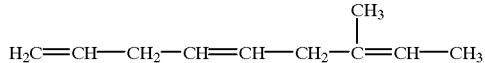

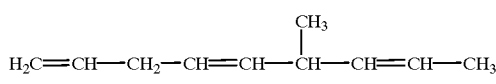

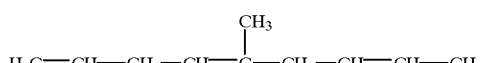

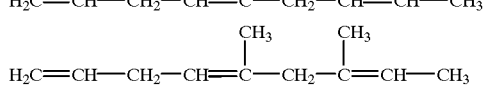

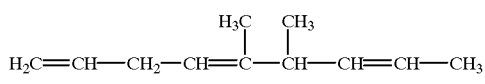

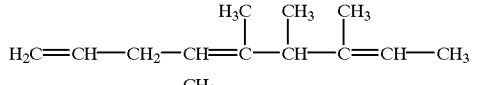

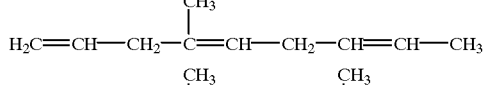

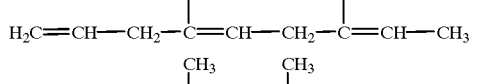

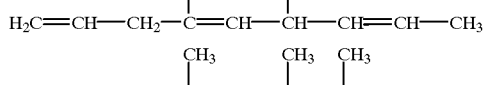

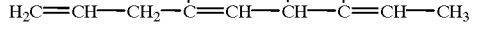

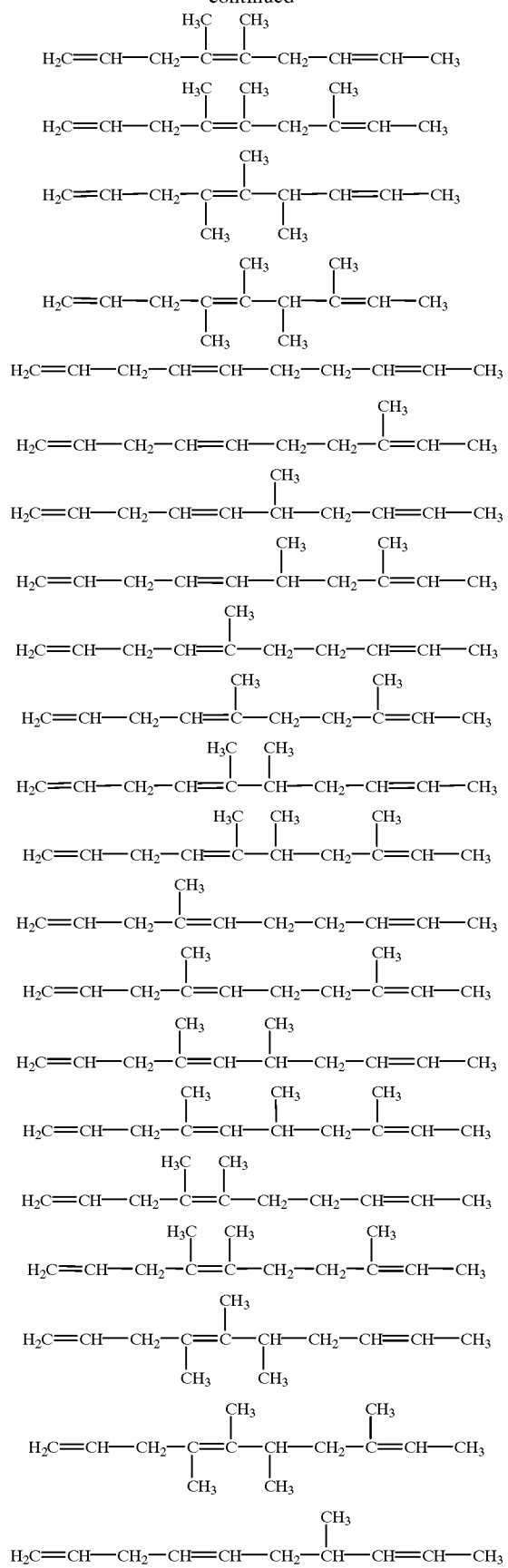
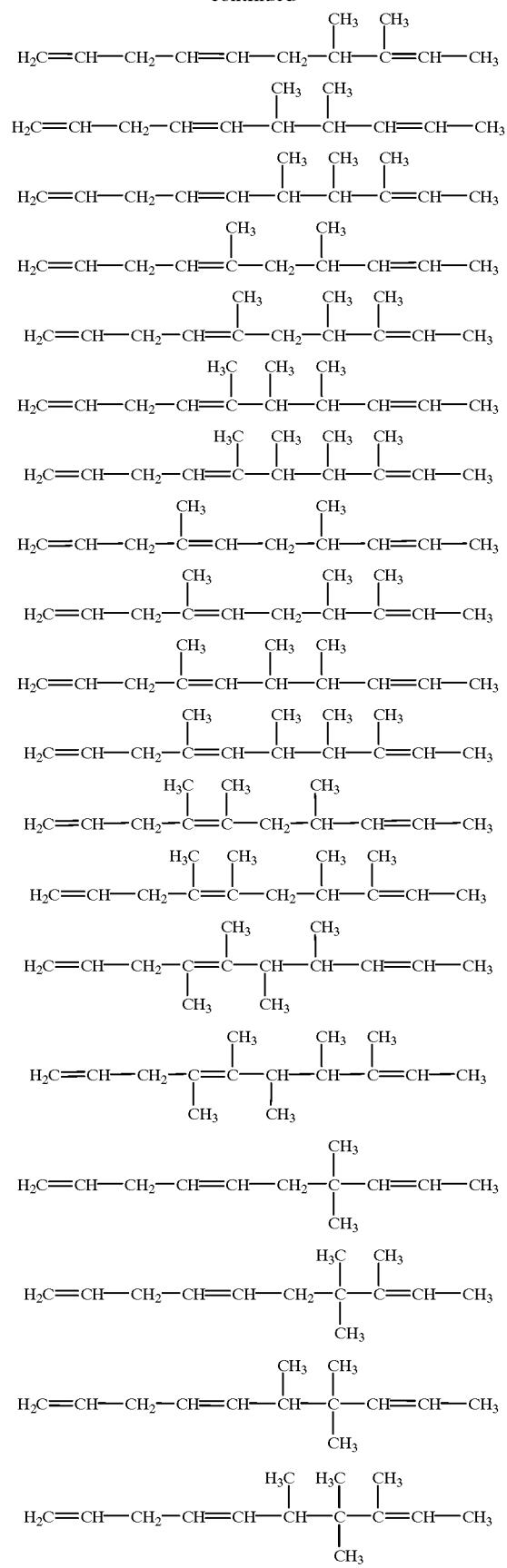

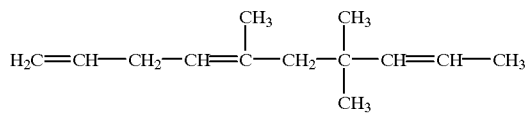
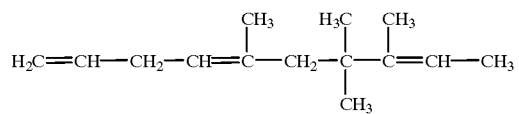
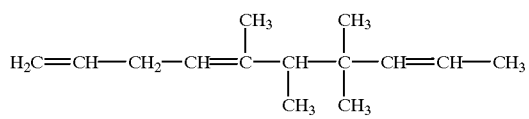
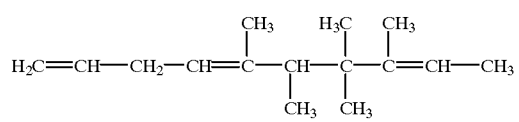
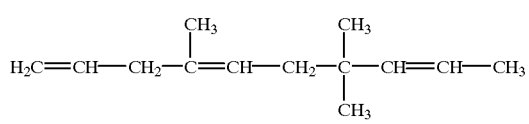
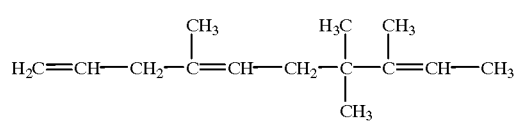
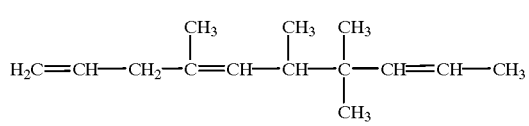
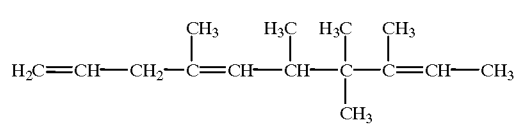
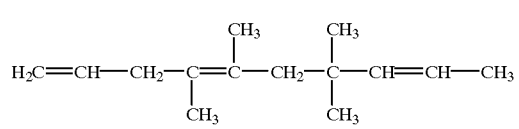
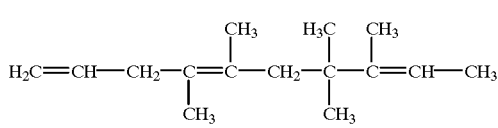
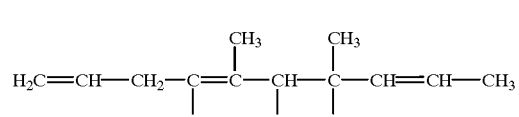
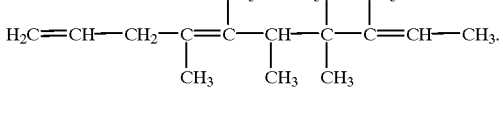
9. The α-olefin/triene random copolymer according to claim 1, wherein the structural unit ($U_{B-1}$) is derived from a linear triene compound (B1) selected from the group consisting of:
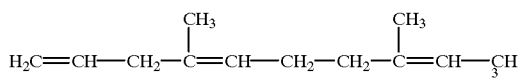
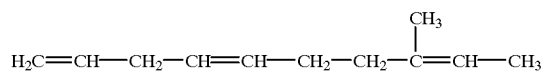
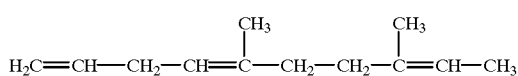
and
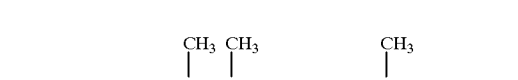
* * * * *

UNITED STATES PATENT AND TRADEMARK OFFICE
CERTIFICATE OF CORRECTION

PATENT NO.   : 6,303,727 B1
DATED        : October 16, 2001
INVENTOR(S)  : Ken Maeda et al.

It is certified that error appears in the above-identified patent and that said Letters Patent is hereby corrected as shown below:

<u>Column 84, claim 7,</u>
Line 24, change "0-0.1-30 mole% to -- 0.1-30 mole% --.

Signed and Sealed this

Second Day of April, 2002

Attest:

JAMES E. ROGAN
*Attesting Officer*   *Director of the United States Patent and Trademark Office*